(12) United States Patent
Gregory et al.

(10) Patent No.: US 11,596,642 B2
(45) Date of Patent: Mar. 7, 2023

(54) THERAPEUTIC TREATMENT OF BREAST CANCER BASED ON C-MAF STATUS

(71) Applicant: INBIOMOTION S.L., Barcelona (ES)

(72) Inventors: Walter Martin Gregory, West Yorkshire (GB); Juan Carlos Tercero, Madrid (ES); Roger Gomis, Barcelona (ES); Robert E. Coleman, Sheffield (GB)

(73) Assignee: INBIOMOTION S.L., Barcelona (ES)

( * ) Notice: Subject to any disclaimer, the term of this patent is extended or adjusted under 35 U.S.C. 154(b) by 97 days.

(21) Appl. No.: 16/303,945

(22) PCT Filed: May 25, 2017

(86) PCT No.: PCT/IB2017/053094
§ 371 (c)(1),
(2) Date: Nov. 21, 2018

(87) PCT Pub. No.: WO2017/203468
PCT Pub. Date: Nov. 30, 2017

(65) Prior Publication Data
US 2019/0269707 A1    Sep. 5, 2019

Related U.S. Application Data

(60) Provisional application No. 62/344,836, filed on Jun. 2, 2016, provisional application No. 62/341,333, filed on May 25, 2016.

(51) Int. Cl.
| | |
|---|---|
| *A61K 31/663* | (2006.01) |
| *A61K 31/47* | (2006.01) |
| *C12Q 1/686* | (2018.01) |
| *C12Q 1/6874* | (2018.01) |
| *C12Q 1/6841* | (2018.01) |
| *C12Q 1/6886* | (2018.01) |
| *A61P 35/04* | (2006.01) |
| *A61K 9/00* | (2006.01) |
| *C07K 16/28* | (2006.01) |

(52) U.S. Cl.
CPC .......... *A61K 31/663* (2013.01); *A61K 9/0019* (2013.01); *A61K 9/0053* (2013.01); *A61K 31/47* (2013.01); *A61P 35/04* (2018.01); *C07K 16/2878* (2013.01); *C12Q 1/686* (2013.01); *C12Q 1/6841* (2013.01); *C12Q 1/6874* (2013.01); *C12Q 1/6886* (2013.01); *C12Q 2563/107* (2013.01); *C12Q 2600/106* (2013.01); *C12Q 2600/118* (2013.01); *C12Q 2600/158* (2013.01)

(58) Field of Classification Search
CPC .... A61K 31/663; A61P 35/04; G01N 2800/52
See application file for complete search history.

(56) References Cited

U.S. PATENT DOCUMENTS

| | | |
|---|---|---|
| 6,274,338 B1 | 8/2001 | Glimcher et al. |
| 6,740,522 B2 | 5/2004 | Anderson et al. |
| 7,019,028 B2 | 3/2006 | Eder et al. |
| 7,097,834 B1 | 8/2006 | Boyle |
| 7,364,736 B2 | 4/2008 | Boyle et al. |
| 7,411,050 B2 | 8/2008 | Anderson |
| 8,642,270 B2 | 2/2014 | Leyland-Jones et al. |
| 9,127,302 B2 | 9/2015 | Verrant et al. |
| 9,134,237 B2 | 9/2015 | Connelly et al. |
| 9,702,878 B2 | 7/2017 | Gomis et al. |
| 10,006,091 B2 | 6/2018 | Gomis et al. |
| 10,047,398 B2 | 8/2018 | Gomis et al. |
| 10,114,022 B2 | 10/2018 | Gomis et al. |
| 10,119,171 B2 | 11/2018 | Gomis et al. |
| 10,793,642 B2 | 10/2020 | Gomis et al. |
| 10,866,241 B2 | 12/2020 | Gomis et al. |
| 11,041,213 B2 | 6/2021 | Gomis et al. |
| 11,041,861 B2 | 6/2021 | Gomis et al. |
| 11,072,831 B2 | 7/2021 | Gomis et al. |
| 2004/0138313 A1 | 7/2004 | Eder et al. |
| 2005/0181375 A1 | 8/2005 | Aziz et al. |
| 2008/0219996 A1 | 9/2008 | Kalebic et al. |
| 2009/0029378 A1 | 1/2009 | Connelly et al. |
| 2009/0048117 A1 | 2/2009 | Glimcher et al. |
| 2009/0220955 A1 | 9/2009 | Verrant |
| 2010/0113297 A1 | 5/2010 | Lidereau et al. |
| 2010/0210738 A1 | 8/2010 | Leyland-Jones et al. |
| 2011/0130296 A1 | 6/2011 | Benz et al. |
| 2011/0150979 A1 | 6/2011 | Ray et al. |
| 2011/0152113 A1 | 6/2011 | Escudero et al. |
| 2014/0057796 A1 | 2/2014 | Gomis et al. |
| 2014/0105918 A1* | 4/2014 | Gomis .................... A61P 19/00 424/174.1 |
| 2014/0162887 A1 | 6/2014 | Martin et al. |
| 2014/0303133 A1 | 10/2014 | Pietenpol et al. |
| 2014/0314792 A1 | 10/2014 | Gomis et al. |

(Continued)

FOREIGN PATENT DOCUMENTS

| | | |
|---|---|---|
| EP | 0120694 A2 | 10/1984 |
| EP | 0125023 A1 | 11/1984 |
| EP | 1961825 A1 | 8/2008 |
| EP | 2626431 A2 | 8/2013 |
| EP | 2650682 A1 | 10/2013 |

(Continued)

OTHER PUBLICATIONS

Coleman et al., BreastCancer Adj uvant Therapy with Zoledronic Acid, N Eng J Med., 2011, 365: 1396-1405.*

(Continued)

*Primary Examiner* — Hong Sang
(74) *Attorney, Agent, or Firm* — Sterne, Kessler, Goldstein & Fox P.L.L.C.

(57) ABSTRACT

The present invention relates to the design of a customized therapy for a subject with breast cancer based on the c-MAF expression level and the menopausal status of the subject. In some embodiments, the customized therapy comprises an agent for avoiding or preventing bone degradation. In some embodiments, the agent for avoiding or preventing bone degradation is zoledronic acid.

19 Claims, 33 Drawing Sheets
Specification includes a Sequence Listing.

(56) References Cited

U.S. PATENT DOCUMENTS

| | | |
|---|---|---|
| 2015/0152506 A1 | 6/2015 | Gomis et al. |
| 2015/0293100 A1 | 10/2015 | Gomis et al. |
| 2015/0362495 A1 | 12/2015 | Gomis et al. |
| 2016/0032399 A1 | 2/2016 | Gomis et al. |
| 2016/0032400 A1 | 2/2016 | Gomis et al. |
| 2016/0040247 A1 | 2/2016 | Gomis et al. |
| 2017/0002357 A1 | 1/2017 | Gomis et al. |
| 2017/0088900 A1 | 3/2017 | Anjamshoaa et al. |
| 2017/0101683 A1 | 4/2017 | Gomis et al. |
| 2017/0121777 A1 | 5/2017 | Gomis et al. |
| 2017/0369589 A1 | 12/2017 | Gomis et al. |
| 2017/0370935 A1 | 12/2017 | Gomis et al. |
| 2019/0119757 A1 | 4/2019 | Gomis et al. |
| 2019/0169693 A1 | 6/2019 | Gomis et al. |
| 2019/0242898 A1 | 8/2019 | Gomis et al. |
| 2019/0256922 A1 | 8/2019 | Gomis et al. |
| 2019/0256992 A1 | 8/2019 | Gomis et al. |
| 2019/0269707 A1 | 9/2019 | Gregory et al. |
| 2019/0309299 A1 | 10/2019 | Gomis et al. |
| 2021/0137952 A1 | 5/2021 | Gregory et al. |
| 2021/0190784 A1 | 6/2021 | Gomis et al. |
| 2021/0317534 A1 | 10/2021 | Gomis et al. |
| 2021/0388452 A1 | 12/2021 | Gomis et al. |
| 2022/0042997 A1 | 2/2022 | Gomis et al. |
| 2022/0049316 A1 | 2/2022 | Gomis et al. |

FOREIGN PATENT DOCUMENTS

| | | |
|---|---|---|
| WO | WO-9116880 A1 | 11/1991 |
| WO | WO-0055126 A2 | 9/2000 |
| WO | WO-0149288 A1 | 7/2001 |
| WO | WO-03020278 A1 | 3/2003 |
| WO | WO-03020721 A1 | 3/2003 |
| WO | WO-03059249 A2 | 7/2003 |
| WO | WO-2004000843 A1 | 12/2003 |
| WO | WO-2004014888 A1 | 2/2004 |
| WO | WO-2005029067 A2 | 3/2005 |
| WO | WO-2005046731 A1 | 5/2005 |
| WO | WO-2005063252 A1 | 7/2005 |
| WO | WO-2005086891 A2 | 9/2005 |
| WO | WO-2006012221 A2 | 2/2006 |
| WO | WO-2006135436 A2 | 12/2006 |
| WO | WO-2008098351 A1 | 8/2008 |
| WO | WO-2008104543 A2 | 9/2008 |
| WO | WO-2008142164 A2 | 11/2008 |
| WO | WO-2008145125 A1 | 12/2008 |
| WO | WO-2009045115 A1 | 4/2009 |
| WO | WO-2009049410 A1 | 4/2009 |
| WO | WO-2009146546 A1 | 12/2009 |
| WO | WO-2010000907 A1 | 1/2010 |
| WO | WO-2010136569 A1 | 12/2010 |
| WO | WO-2012045905 A2 | 4/2012 |
| WO | WO-2012125828 A2 | 9/2012 |
| WO | WO-2013153458 A2 | 10/2013 |
| WO | WO-2013182912 A2 | 12/2013 |
| WO | WO-2014057357 A2 | 4/2014 |
| WO | WO-2014140896 A2 | 9/2014 |
| WO | WO-2014140933 A2 | 9/2014 |
| WO | WO-2014184679 A2 | 11/2014 |
| WO | WO-2015052583 A2 | 4/2015 |
| WO | WO-2016092524 A1 | 6/2016 |
| WO | WO-2017203468 A1 | 5/2017 |
| WO | WO-2019102380 A1 | 5/2019 |

OTHER PUBLICATIONS

Abbott Molecular, "Vysis LSI IGH/MAF Dual Color Dual Fusion Probe," accessed at http://abbottmolecular.com/us/products/analyte-specific-reagent/fish/vysis-lsi-igh-maf-dual-color-dual-fusion-probe.html, accessed on Oct. 16, 2014, 2 pages.

Abnova, "MAF FISH Probe," accessed at http://abnova.com/products/products_detail.asp?Catalog_id=FA0375, accessed on Oct. 16, 2014, 2 pages.

Afinitor.Com, "Afinitor (everolimus) Tablets," accessed at http://afinitor.com/sega-tuberous-sclerosis/patient/sega-information.jsp, accessed on Oct. 16, 2014, 5 pages.

Agilent Technologies, "Probes for Chromosome 16," accessed at http://genomics.agilent.com/productSearch.jsp?chr=16&start=79483700&end=79754340&_requestid=78075, accessed on Oct. 16, 2014, 3 pages.

Al-Mulla, F., et al., "Expressive Genomic Hybridisation: Gene Expression Profiling at the Cytogenetic Level," Journal of Clinical Pathology: Molecular Pathology 56(4):210-217, BMJ Publishing Group, England (2003).

Amit, A.G., et al., "Three-Dimensional Structure of an Antigen-Antibody Complex at 2.8 A Resolution," Science 233(4765):747-753, American Association for the Advancement of Science, United States (1986).

Andrews, N.C., et al., "The Ubiquitous Subunit of Erythroid Transcription Factor NF-E2 is a Small Basic-leucine Zipper Protein Related to the v-maf Oncogene," Proceedings of the National Academy of Sciences of USA 90(24):11488-11492, National Academy of Sciences, United States (1993).

Annunziata, C.M., et al., "A Mechanistic Rationale for MEK Inhibitor Therapy in Myeloma Based on Blockade of MAF Oncogene Expression," Blood, 117(8):2396-2404, American Society of Hematology, United States (Feb. 2011).

ARUP Laboratories, "Multiple Myeloma (MM) by FISH: Detection of Prognostically Significant Genomic Aberrations in Multiple Myeloma (MM) by Fluorescence in situ Hybridization (FISH)," accessed at http://aruplab.com, accessed on Oct. 16, 2014, 2 pages.

AZURE Trial Protocol for: Coleman, R.E., et al., "Breast-Cancer Adjuvant Therapy with Zoledronic Acid," The New England Journal of Medicine 365(15):1396-1405, Massachusetts Medical Society, United States (2011), 144 pages.

Badve, S., et al. "Basal-like and Triple-negative Breast Cancers: A Critical Review with an Emphasis on the Implications for Pathologists and Oncologists," Modern Pathology 24(2):157-167, USCAP, Inc., United States (2011).

Baker, S.G., "The Central Role of Receiver Operating Characteristic (ROC) Curves in Evaluating Tests for the Early Detection of Cancer," Journal of the National Cancer Institute 95(7):511-515, Oxford University Press, England (2003).

Barrett, T., et al., "NCBI GEO: Mining Tens of Millions of Expression Profiles—Database and Tools Update," Nucleic Acids Research 35(Database Issue):D760-D765, Oxford University Press, England (2007).

Baselga, J., et al., "Everolimus in Postmenopausal Hormone-Receptor-Positive Advanced Breast Cancer," The New England Journal of Medicine 366(6):520-529, Massachusetts Medical Society, United States (Feb. 2012).

Bertucci, F., et al., "How Basal are Triple-Negative Breast Cancers?," International Journal of Cancer 123(1):236-240, Wiley-Liss, United States (2008).

Bogado, C.E., et al., "Denosumab: An Update," Drugs of Today 47(8):605-613, Prous Science, United States (2011).

Bohn, O.L., et al., "Biomarker Profile in Breast Carcinomas Presenting with Bone Metastasis," International Journal of Clinical and Experimental Pathology 3(2):139-146, E-Century Publishing Corporation, United States (2010).

Bos, P.D., et al., "Genes that Mediate Breast Cancer Metastasis to the Brain," Nature 459(7249):1005-1009, Nature Publishing Group, England (2009).

Bowles, D.W., et al., "Multi-targeted Tyrosine Kinase Inhibitors in Clinical Development: Focus on XI-184 (Cabozantinib)," Drugs of today (Barcelona, Spain) 47(11):857-868, Clarivate Analytics, Spain (Nov. 2011).

Brufsky, A.M., et al., "The Evolving Role of Bone-Conserving Therapy in Patients with Breast Cancer," Seminars in Oncology 37(Suppl 1):S12-S19, W.B. Saunders, United States (Jun. 2010).

Bruland Ø.S., et al., "High-Linear Energy Transfer Irradiation Targeted to Skeletal Metastases by the Alpha-emitter 223Ra: Adjuvant or Alternative to Conventional Modalities?," Clinical Cancer Research 12 (20 Pt 2):6250s-6257s, American Association for Cancer Research, Denville, NJ (Oct. 2006).

(56) References Cited

OTHER PUBLICATIONS

Cancer Genome Atlas Network, "Comprehensive Molecular Portraits of Human Breast Tumors," Nature 490(7418):61-70, Nature Publishing Group, England (2012).
Carey, L.A., "Triple-Negative (basal-like) Breast Cancer: A New Entity," Breast Cancer Research 9(Suppl1):p. S11, BioMed Central Ltd., England (2007).
Caton, A.J., et al., "Identical D Region Sequences Expressed by Murine Monoclonal Antibodies Specific for a Human Tumor-associated Antigen," Journal of Immunology 144(5):1965-1968, American Association of Immunologists, United States (Mar. 1990).
CGI Italia, "IGH/MAF Two Color, Two Fusion Translocation Probe," accessed at http://cancergeneticsitalia.com/dna-fish-probe/ighmaf/, accessed on Oct. 16, 2014, 1 page.
Choi, M., et al., "Genetic Diagnosis by Whole Exome Capture and Massively Parallel DNA Sequencing," Proceedings of the National Academy of Sciences of USA 106(45):19096-19101, National Academy of Sciences, United States (2009).
Chothia, C. and Lesk, A.M., "Canonical Structures for the Hypervariable Regions of Immunoglobulins," Journal of Molecular Biology 196(4):901-917, Elsevier Science, United States (Aug. 1987).
Chothia, C., et al., "Conformations of Immunoglobulin Hypervariable Regions," Nature 342(6252):877-883, Nature Publishing Group, England (Dec. 1989).
Clinicaltrials.Gov, "Study of Denosumab as Adjuvant Treatment for Women With High Risk Early Breast Cancer Receiving Neoadjuvant or Adjuvant Therapy (D-CARE)," Identifier NCT01077154, accessed at https://clinicaltrials.gov/ct2/show/NCT01077154, last accessed on Aug. 25, 2017, 6 pages.
Coleman, R., et al., "Effect of MAF Amplification on Treatment Outcomes with Adjuvant Zoledronic Acid in Early Breast Cancer: A Secondary Analysis of the International, Open-Label, Randomised, Controlled, Phase 3 Azure (BIG 01/04) Trial," The Lancet Oncology 18(11):1543-1552, Lancet Publication, England (Nov. 2017).
Coleman, R.E., et al., "Breast-Cancer Adjuvant Therapy with Zoledronic Acid," The New England Journal of Medicine 365(15):1396-1405, Massachusetts Medical Society, United States (Oct. 2011), with Supplementary Appendix, 18 pages.
Co-pending U.S. Appl. No. 15/944,499, inventors Gomis, R., et al., filed Apr. 3, 2018 (Not Published).
Co-pending U.S. Appl. No. 15/944,510, inventors Gomis R., et al., filed Apr. 3, 2018 (Not Published).
Co-pending U.S. Appl. No. 15/955,790, Inventors Gomis, R., et al., filed Apr. 18, 2018 (Not Published).
Creative Bioarray, "Products," accessed at http://creative-bioarray.com/Products.htm, accessed on Oct. 16, 2014, 2 pages.
Curtis, C., et al., "The Genomic and Transcriptomic Architecture of 2,000 Breast Tumours Reveals Novel Subgroups," Nature 486(7403):346-352, Nature Publishing Group, England (2012).
Cytocell, "Oncology and Constitutional FISH Probe Catalogue 2012/2013," accessed at http://zentech.be/uploads/docs/products_info/prenatalogy/cytocell%202012-2013%20catalogue%5B3%5D.pdf, accessed on Oct. 16, 2014, 134 pages.
Dako, "SureFISH Probes," accessed at http://dako.com/us/ar42/psg42806000/baseproducts_surefish.htm?setCountry=true&purl=ar42/psg42806000/baseproducts_surefish.htm?undefined&submit=Accept%20country, accessed on Oct. 16, 2014, 2 pages.
Dannhardt, G. and Kiefer, W., "Cyclooxygenase Inhibitors—Current Status and Future Prospects," European Journal of Medicinal Chemistry 36(2):109-126,Editions Scientifiques et Medicales Elsevier SAS, France (2001).
Dean-Colomb, W., et al., "Elevated Serum P1NP Predicts Development of Bone Metastasis and Survival in Early-Stage Breast Cancer," Breast Cancer Research and Treatment 137(2):631-636, Springer Science+Business Media,United States(2012).
Demarest, J.F., et al., "Update on Aplaviroc: An HIV Entry Inhibitor Targeting CCR5," Retrovirology 2(Suppl 1):S13, BioMed Central, England (2005).

Dhesy-Thind, S., et al., "Use of Adjuvant Bisphosphonates and Other Bone-Modifying Agents in Breast Cancer: A Cancer Care Ontario and American Society of Clinical Oncology Clinical Practice Guideline," J Clin Oncol 35, American Society of Clinical Oncology, United States, 22 pages (published online before print Mar. 6, 2017).
Early Breast Cancer Trialists' Collaborative Group (EBCTCG), "Adjuvant Bisphosphonate Treatment in Early Breast Cancer: Meta-analyses of Individual Patient Data From Randomised Trials," Lancet 386(10001):1353-1361, Elsevier, England (2015).
Ettenberg, S.A., et al., "BHQ880, A Novel Anti-DKK1 Neutralizing Antibody, Inhibits Tumor-Induced Osteolytic Bone Disease," Proceedings of the American Association for Cancer Research 49:947, Abstract 3987, American Association for Cancer Research, United States (2008).
Extended European Search Report for EP Application No. 12382139.9, European Patent Office, Munich, Germany, dated Sep. 20, 2012, 8 pages.
Extended European Search Report for EP Application No. 15180897.9, European Patent Office, Munich, Germany, dated Sep. 29, 2016, 9 pages.
Extended European Search Report for EP Application No. 19165007.6, The Hague, Netherlands, dated May 22, 2019.
Extended European Search Report for Application No. EP19159414.2, dated Jun. 13, 2019, 10 pages.
Eychene, A., et al., "A New MAFia in Cancer," Nature Reviews Cancer 8(9):683-693, Nature Publishing Group, England (2008).
Fili, S., et al., "Therapeutic Implications of Osteoprotegerin," Cancer Cell International 9:26:1-8, BioMed Central Ltd., England (2009).
Finn, R.S., et al., "Targeting the Cyclin-dependent Kinases (CDK) 4/6 in Estrogen Receptor-positive Breast Cancers," Breast Cancer Research 18(1):17, BioMed Central Ltd., England, 11 pages (2016).
Fornier, M.N., et al., "Phase I Dose-finding Study of Weekly Docetaxel Followed by Flavopiridol for Patients with Advanced Solid Tumors," Clinical Cancer Research 13(19):5841-5846, The Association, United States (Oct. 2007).
Fujiwara, K.T., et al., "Two New Members of the maf Oncogene Family, mafK and mafF, Encode Nuclear b-Zip Proteins Lacking Putative Trans-Activator Domain," Oncogene 8(9):2371-2380, Nature Publishing Group, England (1993).
GenBank Database, "*Homo sapiens* Chromosome 16 Genomic Contig, GRCh37.p10 Primary Assembly," NCBI Reference Sequence Accession No. NT_010498, accessed at https://www.ncbi.nlm.nih.gov/nuccore/NT_010498.15, accessed on Jun. 20, 2013, 5 pages.
GenBank Database, "*Homo sapiens* Chromosome 16 Genomic Contig, GRCh37.p10 Primary Assembly," NCBI Reference Sequence Accession No. NT_010542.15, accessed at http://www.ncbi.nlm.nih.gov/nuccore/NT_010542.15, accessed on Jun. 20, 2013, 2 pages.
GenBank Database, "*Homo sapiens* v-maf avian musculoaponeurotic fibrosarcoma oncogene homolog (MAF), RefSeqGene on chromosome 16," NCBI Reference Sequence Accession No. NG_016440, accessed at http://www.ncbi.nlm.nih.gov/nuccore/NG_016440, accessed on Apr. 3, 2015, 5 pages.
GenBank Database, "*Homo sapiens* v-maf avian musculoaponeurotic fibrosarcoma oncogene homolog (MAF), transcript variant 1, mRNA," NCBI Reference Sequence Accession No. NM_005360.4, accessed at http://www.ncbi.nlm.nih.gov/nuccore/NM_005360.4, accessed on Apr. 3, 2015, 5 pages.
GenBank Database, "*Homo sapiens* v-maf avian musculoaponeurotic fibrosarcoma oncogene homolog (MAF), transcript variant 2, mRNA," NCBI Reference Sequence Accession No. NM_001031804.2, accessed at http://www.ncbi.nlm.nih.gov/nuccore/NM_001031804.2, accessed on Apr. 3, 2015, 6 pages.
Gene Expression Omnibus Database, Accession No. GSE 12276, made public on Jun. 13, 2009, accessed at http://www.ncbi.nlm.nih.gov/geo/query/acc.cgi?acc=GSE12276, accessed on Jun. 20, 2013, 2 pages.
Gene Expression Omnibus Database, Accession No. GSE 14020, made public on May 1, 2009, accessed at http://www.ncbi.nlm.nih.gov/geo/query/acc.cgi?acc=GSE14020, accessed on Jun. 20, 2013, 2 pages.

(56) References Cited

OTHER PUBLICATIONS

Gene Expression Omnibus Database, Accession No. GSE 2034, made public on Feb. 23, 2005, accessed at http://www.ncbi.nlm.nih.gov/geo/query/acc/cgi?acc=GSE+2034, accessed on Jun. 20, 2013, 7 pages.
Gene Expression Omnibus Database, Accession No. GSE 2603, made public on Jul. 28, 2005, accessed at http://www.ncbi.nlm.nih.gov/geo/query/acc/cgi?acc=GSE+2603, accessed on Jun. 20, 2013, 2 pages.
GenPept Database, "RecName: Full=Transcription Factor Maf; AltName: Full=Proto-oncogene c-Maf; AltName: Full=V-maf Musculoaponeurotic Fibrosarcoma Oncogene Homolog [*Homo sapiens*]," UniProtKB/Swiss-Prot:Accession No. O75444.2, accessed at https://www.ncbi.nlm.nih.gov/protein/o75444, accessed on Apr. 3, 2015, 6 pages.
GenPept Database, "transcription factor Maf isoform a [*Homo sapiens*]" NCBI Reference Sequence Accession No. NP_005351.2, accessed at http://www.ncbi.nlm.nih.gov/protein/NP_005351.2, accessed on Apr. 3, 2015, 4 pages.
GenPept Database, "transcription factor Maf isoform b [*Homo sapiens*]" NCBI Reference Sequence Accession No. NP_001026974.1, accessed at http://www.ncbi.nlm.nih.gov/protein/NP_001026974, accessed on Apr. 3, 2015, 4 pages.
Gentleman, R.C., et al., "Bioconductor: Open Software Development for Computational Biology and Bioinformatics," Genome Biology 5(10):R80, 16 pages, BioMed Central Ltd, England (2004).
Genycell Biotech, "FISH Mieloma Multiple," accessed at http://google.com/url?sa=t&rct=j&q=&esrc=s&source=web&cd=1&ved=CCQQFjAA&url=http%3A%2F%2Fwww.genycell.es%2Fimages%2Fproductos%2Fbrochures%2Flphmie6_86.ppt&ei=MhFYUOi3GKWH0QGIt4DoDw&usg=AFQjCNEqQMbT8vQGjJbi9riEf3IVgoFTFQ&sig2=V5IS8juEMVHBI8Mv2Xx_Ww, accessed on Oct. 16, 2014, 1 page.
Giancotti, V., "Breast Cancer Markers," Cancer Letters, 243(2):145-159, Elsevier Ireland Ltd., Ireland (2006).
Gnant, M., et al., "Adjuvant Bisphosphonates in Endocrine-responsive Breast Cancer: What is their Place in Therapy?" Therapeutic Advances in Medical Oncology 1(3):123-136, Sage, England (2009).
Gnant, M., et al., "Adjuvant Denosumab in Breast Cancer (ABCSG-18): a Multicentre, Randomised, Double-Blind, Placebo-Controlled Trial," Lancet, 386(9992):433-443, Elsevier, England (Aug. 2015).
Goss, P.E., and Chambers, A.F., "Does Tumour Dormancy Offer a Therapeutic Target?," Nature Reviews. Cancer 10(12):871-877, Macmillan Publishers Ltd., England (2010).
Gur-Dedeoglu, B., et al., "A Resampling-Based Meta-Analysis for Detection of Differential Gene Expression in Breast Cancer," BMC Cancer 8:396, BioMed Central Ltd, England (2008).
Hadji, P., et al., "Adjuvant Bisphosphonates in Early Breast Cancer: Consensus Guidance for Clinical Practice From a European Panel," Annals of Oncology 27(3):379-390, Oxford University Press, England (2016).
Hammond, M.E.H., et al., "American Society of Clinical Oncology/College of American Pathologists Guideline Recommendations for Immunohistochemical Testing of Estrogen and Progesterone Receptors in Breast Cancer," Journal of Clinical Oncology 28(16):2784-2795, American Society of Clinical Oncology, United States (2010).
Henry, D.H., et al., "Randomized, Double-Blind Study of Denosumab Versus Zoledronic Acid in the Treatment of Bone Metastases in Patients with Advanced Cancer (Excluding Breast and Prostate Cancer) or Multiple Myeloma," Journal of Clinical Onocology 29(9):1125-1132, American Society of Clinical Oncology, United States (2011).
Hiraga, T., "Role of Cyclooxygenase-2 in the Bone Metastasis of the Breast Cancer [Nyugan No Honeteni Ni Okeru Shikurookishigenaze-2 No Yakuwari]," Bone 20(5):563-566, Japan (2006).
Holliger, P, and Hudson, P.J., "Engineered Antibody Fragments and the Rise of Single Domains," Nature Biotechnology 23(9):1126-1136, Nature America Publishing, United States (2005).
Hospira Healthcare Corporation, "Prescribing Information: Zoledronic Acid for Injection, 4 mg/5 mL (0.8 mg/mL), zoledronic acid (as zoledronic acid monohydrate)," Control No. 182128, prepared May 4, 2015, accessed at https://www.hospira.ca/en/images/2015.05.04%20Zoledronic%20Acid%204%20mg%20Eng%20PI_tcm87-97657.PDF, 32 pages.
Hu, G., et al., "MTDH Activation by 8q22 Genomic Gain Promotes Chemoresistance and Metastasis of Poor-Prognosis Breast Cancer," Cancer Cell 15(1):9-20, Cell Press, United States (2009).
Huang, Q. and Ouyang, X., "Biochemical-Markers for the Diagnosis of Bone Metastasis: A Clinical Review," Cancer Epidemiology 36(1):94-98, Elsevier Ltd., Netherlands (2012).
Huober J and Thurlimann B, "Bone Targeted Therapy in Breast Cancer: Present and Future," Critical Reviews in Oncology/Hematology 74 Suppl 1:S7-S10, Elsevier Scientific Publishers, Netherlands (Apr. 2010).
Hurt, E.M., et al., "Overexpression of c-maf is a Frequent Oncogenic Event in Multiple Myeloma that Promotes Proliferation and Pathological Interactions with Bone Marrow Stroma," Cancer Cell 5(2):191-199, Cell Press, United States (Feb. 2004).
Igarashi, K., et al., "Activity and Expression of Murine Small Maf Family Protein MafK," The Journal of Biological Chemistry 270(13):7615-7624, The American Society for Biochemistry and Molecular Biology, Inc., United States (1995).
International Preliminary Report on Patentability for Application No. PCT/ES2011/070693, International Bureau of WIPO, Sweden, dated Apr. 9, 2013, 8 pages.
International Preliminary Report on Patentability for Application No. PCT/IB2013/001204, European Patent Office, Rijswijk, Netherlands, dated Aug. 11, 2014, 35 pages.
International Preliminary Report on Patentability for International Application No. PCT/IB2014/002675, The International Bureau of WIPO, Geneva, Switzerland, dated Apr. 12, 2016, 12 pages.
International Search Report and Written Opinion for Application No. PCT/ES2011/070693, European Patent Office, Netherlands, dated Apr. 2, 2012, 12 pages.
International Search Report and Written Opinion for Application No. PCT/IB2013/001204, European Patent Office, Rijswijk, Netherlands, dated Dec. 17, 2013, 11 pages.
International Search Report and Written Opinion for Application No. PCT/IB2018/059189, dated May 7, 2019, 32 pages.
International Search Report and Written Opinion for International Application No. PCT/IB2014/002675, dated Jun. 3, 2015,17 pages.
International Search Report and Written Opinion for International Application No. PCT/IB2017/053094, European Patent Office, Rijswijk, dated Aug. 14, 2017, 19 pages.
Johnson, K., "Denosumab Boosts Survival, Not Just Bones, in Breast Cancer," Medscape, Retrieved on [Apr. 23, 2019], Dec. 10, 2015, Retrieved From the Internet: (URL: https://www.medscape.com/viewarticle/855803).
Kang, Y., et al., "A Multigenic Program Mediating Breast Cancer Metastasis to Bone," Cancer Cell 3(6):537-549, Cell Press, United States (2003).
Kataoka, K., et al., "Small Maf Proteins Heterodimerize with Fos and May Act as Competitive Repressors of the NF-E2 Transcription Factor," Molecular and Cellular Biology 15(4):2180-2190, American Society for Microbiology, United States (1995).
Kataoka, K., et al., "Transactivation Activity of Maf Nuclear Oncoprotein is Modulated by Jun, Fos and Small Maf Proteins," Oncogene 12:53-62, Stockton Press, England (1996).
Kharaishvili, G., et al., "Collagen Triple Helix Repeat Containing 1 Protein, Periostin and Versican in Primary and Metastatic Breast Cancer: An Immunohistochemical Study," Journal of Clinical Pathology 64(11):977-982, BMJ Publishing Group, England (2011).
Kim, H., et al., "Multi-cancer Computational Analysis Reveals Invasion-associated Variant of Desmoplastic Reaction Involving INHBA, THBS2 and col. 11A1," BMC Medical Genomics 3:11 pages, BioMed Central, England (Nov. 2010).
Klopocki, E. and Mundlos, S., "Copy-number Variations, Noncoding Sequences, and Human Phenotypes," Annual Review of Genomics and Human Genetics 12:53-72, Annual Reviews, United States (2011).

(56) References Cited

OTHER PUBLICATIONS

Knight III, W.A., et al., "Estrogen Receptor as an Independent Prognostic Factor for Early Recurrence in Breast Cancer," Cancer Research 37(12):4669-4671, American Association for Cancer Research, United States (1977).

Kohler, G. and Milstein, C., "Continuous Cultures of Fused Cells Secreting Antibody of Predefined Specificity," Nature 256(5517):495-497, Macmillan Journals Ltd., England (Aug. 1975).

Kuritzkes, D.R., "HIV-1 Entry Inhibitors: An Overview," Current Opinion in HIV and AIDS 4(2):82-87, Lippincott Williams & Wilkins, United States (2009).

Largo, C., et al., "Identification of Overexpressed Genes in Frequently Gained/Amplified Chromosome Regions in Multiple Myeloma," Haematologica 91(2):184-191, Ferrata Storti Foundation, Italy (2006).

Leica Biosystems, "Kreatech™ FISH Probes," accessed at http://leicabiosystems.com/ihc-ish/kreatech-fish-probes/, accessed on Oct. 16, 2014, 2 pages.

Liepe, K, "Alpharadin, a 223Ra-based Alpha-particle-emitting Pharmaceutical for the Treatment of Bone Metastases in Patients With Cancer," Current Opinion in Investigational Drugs 10(12):1346-1358, Thomson Reuters (Scientific) Ltd, England (Dec. 2009).

Lipton, A., et al., "The science and practice of bone health in oncology: managing bone loss and metastasis in patients with solid tumors," J Natl Compr Canc Netw 7(Suppl 7):S1-30, Jones and Bartlett Publishers, United States (2009).

Maisano, R., et al., "Novel Therapeutic Approaches to Cancer Patients with Bone Metastasis," Critical Reviews in Oncology/Hematology 40(3):239-250, Elsevier Science Ireland Ltd., Ireland (2001).

Metasystems, "24XCyte," acessed at http://metasystems-international.com/index.php?option=com_joodb&view=article&joobase=5*id=12%3Ad-5029-100-og&Itemid=272, accessed on Oct. 16, 2014, 2 pages.

Ministry of Health, Social Services and Equality, Data Sheet of "Zoledronic acid Kern Pharma 4 mg/100 mL Solution for Infusion EFG," Text Revised Jul. 2016, Machine-translated Jul. 6, 2017, 38 pages (Ministerio de Sanidad, Servicios Sociales e Igualdad, Ficha Tecnica de "Acido Zoledronico Kern Pharma 4 mg/100 ml Solucion Para Perfusion EFG").

Morito, N., et al., "Overexpression of c-Maf Contributes to T-Cell Lymphoma in Both Mice and Human," Cancer Research 66(2):812-819, American Association for Cancer Research, Japan (Jan. 2006).

Mystakidou, K., et al., "Randomized, Open Label, Prospective Study on the Effect of Zoledronic Acid on the Prevention of Bone Metastases in Patients with Recurrent Solid Tumors That Did Not Present with Bone Metastases at Baseline," Medical Oncology 22(2):195-201, Humana Press Inc., United States (2005).

Nakashima, T., et al., "New Molecular and Biological Mechanism of Antitumor Activities of KW-2478, a Novel Nonansamycin Heat Shock Protein 90 Inhibitor, in Multiple Myeloma Cells," Clinical Cancer Research 16(10):2792-2802, The Association, United States (May 2010).

Neville-Webbe H.L. and Coleman R.E., "Bisphosphonates and RANK Ligand Inhibitors for the Treatment and Prevention of Metastatic Bone Disease," European Journal of Cancer 46(7):1211-1222, Elsevier Science Ltd., England (2010).

Ng, P.C. and Kirkness, E.F., "Whole Genome Sequencing," Methods in Molecular Biology 628:215-226, Springer Science+Business Media, LLC, Netherlands (2010).

Nguyen, D.X. and Massague, J., "Genetic Determinants of Cancer Metastasis," Nature Reviews Genetics 8(5):341-352, Nature Publishing Group, England (May 2007).

Nguyen, D.X., et al., "Metastasis: From Dissemination to Organ-Specific Colonization," Nature Reviews Cancer 9(4):274-284, Macmillan Publishers Limited, England (Apr. 2009).

Pageau, S.C., "Denosumab," Monoclonal Antibodies 1(3):210-215, Landes Bioscience, United States (May-Jun. 2009).

Paik, S., et al., "A Multigene Assay to Predict Recurrence of Tamoxifen-Treated, Node-Negative Breast Cancer," The New England Journal of Medicine 351(27):2817-2826, Massachusetts Medical Society, United States (2004).

Paterson, A.H., et al., "Oral Clodronate for Adjuvant Treatment of Operable Breast Cancer (National Surgical Adjuvant Breast and Bowel Project protocol B-34): A Multicentre, Placebo-controlled, Randomised Trial," The Lancet Oncology 13(7):734-742, Lancet Pub. Group, England (Jul. 2012).

Paterson, A.H.G. and Shea-Budgell, M.A., "Bone Health in Patients with Breast Cancer: Recommendations from an Evidence-Based Canadian Guideline," Journal of Clinical Medicine 2(4):283-301, MDPI AG, Switzerland (2013).

Coleman, R.E., et al., "Benefits and risks of adjuvant treatment with zoledronic acid in stage II/III breast cancer. 10 years follow-up of the AZURE randomized clinical trial (BIG 01/04)," Journal of Bone Oncology, 13(1):123-135, Elsevier (Nov. 2018).

Costa, L and Ferreira, A.R., "Adjuvant zoledronic acid to treat breast cancer: not for all," The Lancet Oncology, 18(11):1437-1439, The Lancet Publishing Group, England (Nov. 2017).

Horlings, H.M., et al., "Integration of DNA Copy Number Alterations and Prognostic Gene Expression Signatures in Breast Cancer Patients," Clinical Cancer Research, 16(2):651-663, The Association, United States (Jan. 2010).

Liao, S., et al., "Identification of New Breast Cancer Candidate Genes Associated with Stromal Invasion," Cancer Research, Abstract #4036, 69(2 Suppl), (Jan. 2009), Retrieved from the Internet http://cancerres.aacrjournals.org/content/69/2_Supplement/4036, 4 pages.

Polascik, T.J., "Bisphosphonates in Oncology: Evidence for the Prevention of Skeletal Events in Patients with Bone Metastases," Drug Design, Development and Therapy 3:27-40, Dove Medical Press Ltd., New Zealand (2009).

Pollack, J.R., et al., "Microarray Analysis Reveals a Major Direct Role of DNA Copy Number Alteration in the Transcriptional Program of Human Breast Tumors," Proceedings of the National Academy of Sciences of USA 99(20):12963-12968, National Academy of Sciences, United States (2002).

Rocques, N., et al., "GSK-3-Mediated Phosphorylation Enhances Maf-Transforming Activity," Molecular Cell 28(4):584-597, Cell Press, United States (2007).

Rojo, F., et al., "Nuclear PARP-1 Protein Overexpression is Associated with Poor Overall Survival in Early Breast Cancer," Annals of Oncology 23(5):1156-1164, Oxford University Press, England (2012).

Rotstein, D.M., et al., "Spiropiperidine CCR5 Antagonists," Bioorganic and Medicinal Chemistry Letters 19(18):5401-5406, Elsevier Ltd., England (2009).

Santana-Codina, N., et al., "A Transcriptome-proteome Integrated Network Identifies Endoplasmic Reticulum Thiol Oxidoreductase (ERp57) as a Hub that Mediates Bone Metastasis," Molecular and Cellular Proteomics 12(8):2111-2125, The American Society for Biochemistry and Molecular Biology, Inc., United States (2013).

Segal, D.M., et al., "The Three-dimensional Structure of a Phosphorylcholine-binding Mouse Immunoglobulin Fab and the Nature of the Antigen Binding Site," Proceedings of the National Academy of Sciences of the United States of America 71(11):4298-4302, National Academy of Sciences, United States (Nov. 1974).

Sen, B. and Johnson, F.M., "Regulation of SRC Family Kinases in Human Cancers," Journal of Signal Transduction 2011(865819):1-14, Hindawi Publishing Corporation, United States (Apr. 2011).

Sharon, J., "Structural Characterization of Idiotopes by Using Antibody Variants Generated by Site-directed Mutagenesis," Journal of Immunology 144(12):4863-4869, American Association of Immunologists, United States (Jun. 1990).

Sharon, J., "Structural Correlates of High Antibody Affinity: Three Engineered Amino Acid Substitutions Can Increase the Affinity of an Anti-p-azophenylarsonate Antibody 200-fold," Proceedings of the National Academy of Sciences of the United States of America 87(12):4814-4817, National Academy of Sciences, United States (Jun. 1990).

(56) References Cited

OTHER PUBLICATIONS

Stein, C.A. and Cohen, J.S., "Oligodeoxynucleotides as Inhibitors of Gene Expression: a Review," Cancer Research 48(10):2659-2668, American Association for Cancer Research, United States (1988).
Stopeck, A.T., et al., "Denosumab Compared with Zoledronic Acid for the Treatment of Bone Metastases in Patients with Advanced Breast Cancer: A Randomized, Double-Blind Study," Journal of Clinical Oncology 28(35): 5132-5139, Alexandria, American Society of Clinical Oncology, United States (2010).
Supplementary Appendix for: Coleman, R.E., et al., "Breast-Cancer Adjuvant Therapy with Zoledronic Acid," The New England Journal of Medicine 365(15):1396-1405, Massachusetts Medical Society, United States (2011), 18 pages.
Sutherland, R.L., et al., "Expression and Regulation of Cyclin Genes in Breast Cancer," Acta Oncologica 34(5):651-656, Scandinavian University Press, England (1995).
Swennenhuis, J.F., et al., "Construction of Repeat-Free Fluorescence in situ Hybridization Probes," Nucleic Acids Research 40(3):e20:1-8, Oxford University Press, England (Feb. 2012).
Takahashi, S., "Anti-RANKL Antibody for Treatment of Patients with Bone Metastasis from Breast Cancer," Gan To Kagaku Ryoho 39(1):89-94, Gan To Kagaku Ryohosha, Tokyo, Japan (2012).
Thery, C., et al., "Isolation and Characterization of Exosomes from Cell Culture Supernatants and Biological Fluids," Current Protocols in Cell Biology Chapter 3:3.22.1-3.22.29, Oxford University Press, England (2006).
Van de Wetering de Rooij J., et al.,"Safety, Pharmacokinetics and Efficacy of Anti-Rankl Nanobody® Alx-0141 in Healthy Postmenopausal Women," :Annals of the Rheumatic Diseases 70(Suppl. 3):136, 2011 (Abstract).
Velasco-Velazquez, M., et al., "CCR5 Antagonist Blocks Metastasis of Basal Breast Cancer Cells," Cancer Research 72(15):3839-3850, American Association for Cancer Research, United States (Aug. 2012).
Viprey, V.F., et al., "Neuroblastoma mRNAs Predict Outcome in Children With Stage 4 Neuroblastoma: A European HR-NBL1/SIOPEN Study," Journal of Clinical Oncology, 32(10):1074-1083, American Society of Clinical Oncology, United States (Apr. 2014).
Washam, C.L., et al., "Identification of PTHrP(12-48) as a Plasma Biomarker Associated with Breast Cancer Bone Metastasis," Cancer Epidemiology, Biomarkers and Prevention 22(5):972-983, American Association for Cancer Research, United States (2013).
Weber-Mangal, S., et al., "Breast Cancer in Young Women (≤35 years): Genomic Aberrations Detected by Comparative Genomic Hybridization," International Journal of Cancer 107(4):583-592, Wiley-Liss, Inc., United States (2003).
Winer, E.P., et al., "Activity of Cabozantinib (XL184) in Metastatic Breast Cancer (MBC): Results From a Phase 2 Randomized Discontinuation Trial (RDT)," Annual Meeting of the American Society of Clinical Oncology, Chicago, United States (Jun. 1-5, 2012).
Yakes F.M., et al., "Cabozantinib (XL184), a Novel MET and VEGFR2 Inhibitor Simultaneously Suppresses Metastasis, Angiogenesis, and Tumor Growth," in: Molecular Cancer Therapeutics 10(12):2298-2308, American Association for Cancer Research, Inc., Philadelphia, PA (Dec. 2011).
Zeiss, "FISH Probes: XL Haematology," accessed at https://microshop.zeiss.com/?440675675dedc6&1=en&p=uk&f=r&i=5000&o=&h=25&n=1&sd=000000-528-231-uk, accessed on Oct. 16, 2014, 3 pages.
Zhang, X.H-F., et al., "Latent Bone Metastasis in Breast Cancer Tied to Src-Dependent Survival Signals," Cancer Cell 16(1):67-78, Cell Press, United States (2009).
Zhou, H., et al., "Updates of mTOR Inhibitors," Anticancer Agents in Medicinal Chemistry 10(7):571-581, Bentham Science Publishers, Netherlands (2010).
ZOMETA®, "About ZOMETA® (zoledronic acid) 4 mg/5 mL Injection," accessed at http://www.us.zometa.com/index.jsp?usertrack.filter_applied=true&Novald=29353769344676433633, accessed on Apr. 3, 2015, 2 pages.
Yersal, O and Barutca, S., "Biological Subtypes of Breast Cancer: Prognostic and Therapeutic Implications," World Journal of Clinical Oncology, 5(3):412-424, Baishideng Publishing Group, United States (Aug. 2014).
Co-pending U.S. Appl. No. 17/108,390, Inventors Gomis, R., et al., filed Dec. 1, 2020 (Not Published).
Creative Bioarray, "IGH/MAF Translocation, Dual Fusion Probe," accessed at http://www.creative-bioarray.com/IGH-MAF-Translocation,-Dual-Fusion-Probe-FHPC-066-item-4707.htm, accessed on May 21, 2015, 2 pages.
Dako Denmark A/S, "HER2 IQFISH pharmDxTM, Code K5731," Assay Information, 3rd edition, 184 pages (Jun. 2015).
Haas, D, "On the Expanding, Then Contracting Scope of Scientific Publications," FEMS Microbiology Reviews 34(1):1-2, Oxford University Press, United Kingdom (published online Dec. 2009, published in print Jan. 2010).
Haas, M. J., "RANKLing Non-skeletal Tumors," SciBX 3(18):1-2, 2 pages, Targets and Mechanisms, Nature Publishing Group, United Kingdom (published online May 2010).
Paterson, A. H. G., et al., "Validation of MAF biomarker for response prediction to adjuvant bisphosphonates in 2 clinical trials: AZURE and NSABP-B34," Journal of Clinical Oncology 38(15_suppl):513-513, American Society of Clinical Oncology, United States (May 2020).
Reis-Filho, J. S., "Triple Negative and Basal-like Breast Cancer: One or Many diseases? Implications for surgical Pathologists," accessed at https://web.archive.org/web/20130319192034/http://www.uscap.org/site~/98th/pdf/companion03h03.pdf on Aug. 29, 2019, 19 pages, United States & Canadian Academy of Pathology, United States (2009).
Co-pending U.S. Appl. No. 17/241,571, inventors Gomis, R., et al., filed Apr. 27, 2021 (Not yet Published).
Co-pending U.S. Appl. No. 17/339,024, inventor Gomis, R., filed Jun. 4, 2021 (Not yet Published).
Co-pending U.S. Appl. No. 17/353,013, inventor Gomis, R., filed Jun. 21, 2021 (Not yet Published).
Deeks, E. D., and Perry, C. M., "Zoledronic Acid: A Review of its Use in the Treatment of Osteoporosis," Drugs Aging 25(11):963-986, Springerlink, Germany (2008).
GenBank Database, NCBI Reference Sequence NP_001026974.1, accessed on Oct. 16, 2014, accessed at http://www.ncbi.nlm.nih.gov/protein/ NP_001026974.1, 4 pages.
GenBank Database, NCBI Reference Sequence NP_005351.2, accessed on Oct. 16, 2014, accessed at http://www.ncbi.nlm.nih.gov/protein/ NP_005351.2, 4 pages.
Kristensen, B., et al., "Oral Clodronate in Breast Cancer Patients With Bone Metastases: A Randomized Study," Journal of Internal Medicine, 246(1):67-74, Blackwell Scientific Publications, United Kingdom (1999).
Rosen, L,S., et al., "Zoledronic Acid is Superior to Pamidronate for the Treatment of Bone Metastases in Breast Carcinoma Patients With at Least One Osteolytic Lesion," Cancer, 100(1):36-43, Wiley, United States (2004).
Zefei, J., et al., "Expert Consensus on Clinical Diagnosis and Treatment of Breast Cancer Bone Metastasis and Bone-related Diseases (2014 Edition)," Chinese Medical Journal, 95(4):241-247, Chinese Medical Association Publishing House and Wolters Kluwer Medknow, China (Jan. 2015).
Zhao, X, and Hu, X., "Dosing of Zoledronic Acid with its Anti-Tumor Effects in Breast Cancer," Journal of Bone Oncology 4(3):98-101, Elsevier, Netherlands (Oct. 2015).
Martin, M., et al., "Benefit of denosumab therapy inpatients with bone metastases from breast cancer: a number needed-to-treat (NNT) analysis," Breast (Edinburgh, Scotland) (Breast) 20(1):S85, Abstract P347, accessed at URL:[https://www.thebreastonline.com/article/S0960-9776(11)70283-1/pdf] on Feb. 23, 2022, 1 page, Elsevier, Netherlands (Mar. 2011).
Coleman, R., et al., "Abstract P1-09-01: Impact of the MAF gene amplification on disease recurrence and effects of adjuvant zoledronic acid in early breast cancer," Cancer Research 77(4): P1-09-01, AACR Publications, United States (2017).

(56) References Cited

OTHER PUBLICATIONS

Coleman, R., et al., "Adjuvant zoledronic acid in patients with early breast cancer: final efficacy analysis of the AZURE (BIG 01/04) randomized open-bale phase 3 trial," The Lancet Oncology 15:997-1006, Elsevier, Netherlands (2014).

Gnant, M., et al., "Adjuvant endocrine therapy plus zoledronic acid in premenopausal women with eariy-stage breast cancer: 62-month follow-up from the ABCSG-12 randomised trial," Oncology Articles Lancet Oncol 631-641, Elsevier, Netherlands (2011).

Hoon, K., et al., "Multi-cancer computational analysis reveals invasion-associated variant of desmoplastic reaction involving INHBA, THBS2 and col. 11A1," BMC Medical Genomics (3)1:51, Biomed Central Ltd., United Kingdom (2010).

International Search Report and Written Opinion for International Application No. PCT/IB2017/053094, European Patent Office, Netherlands, dated Aug. 14, 2017, 16 pages.

Pavlovic, M., et al., "Enhanced MAF Oncogene Expression and Breast Cancer Bone Metastasis," Journal of the National Cancer Institute 107(12): djv256, Oxford University Press, England (2015).

International Preliminary Report on patentability for International Application No. PCT/IB2017/053094, European Patent Office, Netherlands, dated Mar. 26, 2018 23 pages.

Gralow, J., et al., "Phase III Trial of Bisphosphonates as Adjuvant therapy in Primary Breast Cancer: SWOG/Alliance/ECOG-ACRIN/NCIC Clinical trials Group/NRG Oncology Study S0307," ASCO Meeting Library. Jun. 1, 2015. Retrieved from https://meetinglibrary.asco.org/record/111882/abstract.

* cited by examiner

Figure 1

| MAF-FISH assay validation parameters | MAF-IHC assay validation parameters |
|---|---|
| Different probes analyzed | Dako Autostainer Link vs. Ventana Benchmark Ultra |
| Lot-to-lot variation | |
| Intra-assay-repeatability (same run, same person evaluates) | |
| Intra-assay-repeatability (separate run, same person evaluates) | |
| Stability of the biomarker / storage | |
| Intermediate precision (2 separate technicians performing assay) | Intermediate precision (staining was performed on two different devices) |
| Probe concentration, hybridization temperature | Antibody concentration |

- Impact of Zoledronic Ac. treatment on DFS according MAF FISH on post menopausal patients Figure 30. Impact of Zoledronic Ac. treatment on OS according to MAF FISH

- Impact of Zoledronic Ac. treatment on OS according to MAF FISH in post menopausal patients

SEQUENCE LISTING

<160> NUMBER OF SEQ ID NOS: 24

<210> SEQ ID NO 1
<211> LENGTH: 6878
<212> TYPE: DNA
<213> ORGANISM: Homo sapiens

<400> SEQUENCE: 1

| | | | | | |
|---|---|---|---|---|---|
| agaggcttta | aatctttttt | tcatcttcta | gctgtagctc | gggctgcttg | tcggcttggc | 60 |
| ctcccctcc | cccctttgct | ctctgcctcg | tctttcccca | ggacttcgct | attttgcttt | 120 |
| tttaaaaaaa | ggcaagaaag | aactaaactc | cccctcct | ctcctccagt | cgggctgcac | 180 |
| ctctgccttg | cactttgcac | agaggtagag | agcgcgcgag | ggagagagag | gaaagaaaaa | 240 |
| aaataataaa | gagagccaag | cagaagagga | ggcgagaagc | atgaagtgtt | aactcccccg | 300 |
| tgccaaggcc | cgcgccgccc | ggacagacgc | ccgccgcgcc | tccagccccg | agcggacgcc | 360 |
| gcgcgcgccc | tgcctgcagc | ccgggccggc | gaggcgagcc | cttccttatg | caaagcgcgc | 420 |
| agcggagcgg | cgagcggggg | acgccgcgca | ccgggccggg | ctcctccagc | ttcgccgccg | 480 |
| cagccaccac | cgccgccacc | gcagctcgcg | gaggatcttc | ccgagcctga | agccgccggc | 540 |
| tcggcgcgca | aggaggcgag | cgagcaagga | ggggccgggg | cgagcgaggg | agcacattgg | 600 |
| cgtgagcagg | ggggagggag | ggcggccgcg | ggggcgcgg | gcagggcggg | ggggtgtgtg | 660 |
| tgtgagcgcg | ctcggaggtt | tcgggccagc | caccgccgcg | caagctagaa | gcgccccagc | 720 |
| ccggcaagct | ggctcacccg | ctggccaccc | agcacagccc | gctggcccct | ctcctgcagc | 780 |
| ccatctggcg | gagcggcggc | ggcggcggcg | gcggcggcag | gagaatggca | tcagaactgg | 840 |
| caatgagcaa | ctccgacctg | cccaccagtc | ccctggccat | ggaatatgtt | aatgacttcg | 900 |
| atctgatgaa | gtttgaagtg | aaaaaggaac | cggtggagac | cgaccgcatc | atcagccagt | 960 |
| gcggccgtct | catcgccggg | ggctcgctgt | cctccacccc | catgagcacg | ccgtgcagct | 1020 |
| cggtgccccc | ttccccagc | ttctcggcgc | ccagcccggg | ctcgggcagc | gagcagaagg | 1080 |
| cgcacctgga | agactactac | tggatgaccg | gctacccgca | gcagctgaac | ccgaggcgc | 1140 |
| tgggcttcag | ccccgaggac | gcggtcgagg | cgctcatcag | caacagccac | cagctccagg | 1200 |
| gcggcttcga | tggctacgcg | cgcggggcgc | agcagctggc | cgcggcggcc | ggggccggtg | 1260 |
| ccggcgcctc | cttgggcggc | agcggcgagg | agatgggccc | cgccgccgcc | gtggtgtccg | 1320 |
| ccgtgatcgc | cgcggccgcc | gcgcagagcg | cgcgggccc | gcactaccac | caccaccacc | 1380 |
| accacgccgc | cggccaccac | caccacccga | cggccggcgc | gccggcgcc | gcgggcagcg | 1440 |
| cggccgcctc | ggccggtggc | gctggggcg | cgggcggcgg | tggcccggcc | agcgctgggg | 1500 |
| gcggcggcgg | cggcggcgc | ggcggaggcg | gcggggcgc | ggcggggcg | ggggcgccc | 1560 |
| tgcacccgca | ccacgccgcc | ggcggcctgc | acttcgacga | ccgcttctcc | gacgagcagc | 1620 |
| tggtgaccat | gtctgtgcgc | gagctgaacc | ggcagctgcg | cggggtcagc | aaggaggagg | 1680 |
| tgatccggct | gaagcagaag | aggcggacct | gaaaaaccg | cggctatgcc | cagtcctgcc | 1740 |
| gcttcaagag | ggtgcagcag | agacacgtcc | tggagtcgga | gaagaaccag | ctgctgcagc | 1800 |
| aagtcgacca | cctcaagcag | gagatctcca | ggctggtgcg | cgagagggac | gcgtacaagg | 1860 |
| agaaatacga | gaagttggtg | agcagcggct | tccgagaaaa | cggctcgagc | agcgacaacc | 1920 |
| cgtcctctcc | cgagttttc | atgtgagtct | gacacgcgat | tccagctagc | caccctgata | 1980 |
| agtgctccgc | gggggtccgg | ctcggtgtg | ggcttgctag | ttctagagcc | atgctcgcca | 2040 |
| ccacctcacc | accccaccc | ccaccgagtt | tggccccctt | ggccccctac | acacacacaa | 2100 |

```
acccgcacgc acacaccaca cacacacaca cacacacaca cacaccccac accctgctcg    2160
agtttgtggt ggtggtggct gttttaaact ggggagggaa tgggtgtctg gctcatggat    2220
tgccaatctg aaattctcca taacttgcta gcttgttttt ttttttttttt tacaccccccc   2280 cgccccaccc ccggacttgc acaatgttca atgatctcag cagagttctt catgtgaaac    2340
gttgatcacc tttgaagcct gcatcattca catatttttt cttcttcttc cccttcagtt    2400
catgaactgg tgttcatttt ctgtgtgtgt gtgtgtttta ttttgtttgg attttttttt    2460
ttaattttac ttttagagct tgctgtgttg cccaccttt ttccaacctc caccctcact    2520
ccttctcaac ccatctcttc cgagatgaaa gaaaaaaaaa agcaaagttt tttttcttc     2580 tcctgagttc ttcatgtgag attgagcttg caaaggaaaa aaaaatgtga aatgttatag    2640
acttgcagcg tgccgagttc catcgggttt ttttttagc attgttatgc aaaatagag     2700 aaaaaaatcc tcatgaacct tccacaatca agcctgcatc aaccttctgg gtgtgacttg    2760
tgagttttgg ccttgtgatg ccaaatctga gagtttagtc tgccattaaa aaaactcatt    2820
ctcatctcat gcattattat gcttgctact ttgtcttagc aacaatgaac tataactgtt    2880
tcaaagactt tatggaaaag agacattata ttaataaaaa aaaaaagcct gcatgctgga    2940
catgtatggt ataattattt ttttcctttt ttttcctttt ggcttggaaa tggacgttcg    3000
aagacttata gcatggcatt catacttttg ttttattgcc tcatgacttt tttgagttta    3060
gaacaaaaca gtgcaaccgt agagccttct tcccatgaaa ttttgcatct gctccaaaac    3120
tgctttgagt tactcagaac ttcaacctcc caatgcactg aaggcattcc ttgtcaaaga    3180
taccagaatg ggttacacat ttaacctggc aaacattgaa gaactcttaa tgttttcttt    3240
ttaataagaa tgacgcccca ctttggggac taaaattgtg ctattgccga gaagcagtct    3300
aaaatttatt ttttaaaaag agaaactgcc ccattatttt tggtttgttt tattttattt    3360 ttatatttt tggcttttgg tcattgtcaa atgtggaatg ctctgggttt ctagtatata    3420
atttaattct agttttttata atctgttagc ccagttaaaa tgtatgctac agataaagga    3480
atgttataga taaatttgaa agagttaggt ctgtttagct gtagattttt taaacgattg    3540
atgcactaaa ttgtttacta ttgtgatgtt aaggggggta gagtttgcaa ggggactgtt    3600
taaaaaaagt agcttataca gcatgtgctt gcaacttaaa tataagttgg gtatgtgtag    3660
tctttgctat accactgact gtattgaaaa ccaaagtatt aagagggaaa acgcccctgt    3720
ttatatctgt agggtattt tacattcaaa aatgtatgtt ttttttttctt ttcaaaatta   3780 aagtatttgg gactgaattg cactaagata taacctgcaa gcatataata caaaaaaaaa   3840
ttgcaaaact gtttagaacg ctaataaaat ttatgcagtt ataaaaatgg cattactgca    3900
cagttttaag atgatgcaga tttttttaca gttgtattgt ggtgcagaac tggattttct    3960
gtaacttaaa aaaaaatcca cagttttaaa ggcaataatc agtaaatgtt attttcaggg    4020
actgacatcc tgtctttaaa aagaaatgaa aagtaaatct taccacaata aatataaaaa    4080
aatcttgtca gttactttc ttttacatat tttgctgtgc aaaattgttt tatatcttga    4140
gttactaact aaccacgcgt gttgttccta tgtgcttttc tttcattttc aattctggtt    4200
atatcaagaa aagaataatc tacaataata acggcattt tttttgatt ctgtactcag     4260 tttcttagtg tacagtttaa ctgggcccaa caacctcgtt aaaagtgtaa aatgcatcct    4320
tttctccagt ggaaggattc ctggaggaat agggagacag taattcaggg tgaaattata    4380
ggctgttttt tgaagtgagg aggctggccc catatactga ttagcaatat ttaatataga    4440
tgtaaattat gacctcattt ttttctcccc aaagttttca gttttcaaat gagttgagcc    4500
```

```
ataattgccc ttggtaggaa aaacaaaaca aaacagtgga actaggcttc ctgagcatgg    4560
ccctacactt ctgatcagga gcaaagccat ccatagacag aggagccgga caaatatggc    4620
gcatcagagg tggcttgcgc acatatgcat tgaacggtaa agagaaacag cgcttgcctt    4680
ttcactaaag ttgactattt ttccttcttc tcttacacac cgagattttc ttgttagcaa    4740
ggcctgacaa gatttaacat aaacatgaca aatcatagtt gtttgttttg ttttgctttt    4800
ctctttaaca ctgaagatca tttgtcttaa ataggaaaaa gaaatccac tccttacttc     4860 catatttcca agtacatatc tggtttaaac tatgttatca aatcatattt caccgtgaat    4920
attcagtgga gaacttctct acctggatga gctagtaatg atttcagatc atgctatccc    4980
cagaaataaa agcaaaaaat aatacctgtg tggaatatag gctgtgcttt gatttactgg    5040
tatttacccc aaaataggct gtgtatgggg gctgacttaa agatcccttg gaaagactca    5100
aaactacctt cactagtagg actcctaagc gctgacctat ttttaaatga cacaaattca    5160
tgaaactaat gttacaaatt catgcagttt gcactcttag tcatcttccc ctagcacacc    5220
aatagaatgt tagacaaagc cagcactgtt ttgaaaatac agccaaacac gatgactttt    5280
gttttgtttt ctgccgttct taaaagaaaa aaagataata ttgcaactct gactgaaaga    5340
cttattttta agaaaacagg ttgtgtttgg tgctgctaag ttctggccag tttatcatct    5400
ggccttcctg cctatttttt acaaaacacg aagacagtgt gtaacctcga cattttgacc    5460
ttcctttatg tgctagttta gacaggctcc tgaatccaca cttaattttg cttaacaaaa    5520
gtcttaatag taaacctccc ctcatgagct tgaagtcaag tgttcttgac ttcagatatt    5580
tctttccttt ttttttttt ttcctcatca caactaagag atacacaaac tctgaagaag    5640
cagaaatgga gagaatgctt ttaacaaaaa agcatctgat gaaagatttt aggcaaacat    5700
tctcaaaata agagtgatat tctggatgta gttattgcag ttatctcatg acaaatgagg    5760
cctggattgg aaggaaaata tagttgtgta gaattaagca ttttgatagg aatctacaag    5820
gtagttgaat ataataagca ggtttgggcc cccaaacttt agaaaatcaa atgcaaaggt    5880
gctggcaaaa atgaggtttg agtggctggc tgtaagagaa ggttaactcc tagtaaaagg    5940 cattttaga aataacaatt actgaaaact ttgaagtata gtgggagtag caaacaaata     6000
catgtttttt ttttcttaca aagaactcct aaatcctgag taagtgccat tcattacaat    6060
aagtctctaa atttaaaaaa aaaaaaatca tatgaggaaa tctagctttc ccctttacgc    6120
tgcgtttgat cttttgtctaa atagtgttaa aattcctttc attccaatta cagaactgag    6180
cccactcgca agttggagcc atcagtggga tacgccacat tttggaagcc ccagcatcgt    6240
gtacttacca gtgtgttcac aaaatgaaat ttgtgtgaga gctgtacatt aaaaaaaatc    6300
atcattatta ttattatttg cagtcatgga gaaccaccta cccctgactt ctgtttagtc    6360 tccttttttaa ataaaaatta ctgtgttaga gaagaaggct attaaatgta gtagttaact    6420
atgcctcttg tctgggggtt tcatagagac cggtaggaaa gcgcactcct gcttttcgat    6480
ttatggtgtg tgcaagtaaa caggtgcatt gctttcaacc tgccatacta gttttaaaaa    6540
ttcactgaaa ttacaaagat acatatatat gcatatatat aatggaaagt ttcccggaat    6600
gcaacaatta gcattttaaa atcatatata ggcatgcaca ttctaaatag tactttttca    6660
tgcttcattg tttctctggc agataatttt actaagaaga aaaatagata ttcgactccc    6720
cttccctaaa caaatccacg ggcagaggct ccagcggagc cgagccccct ggttttctcg    6780
taggccctag acgtgttgc atttatcagt gatgtcaaac gtgctcattt gtcagacata     6840
gctgtaaatg aaaacaatgt gtggcaaaat acaaagtt                             6878
```

```
<210> SEQ ID NO 2
<211> LENGTH: 2656
<212> TYPE: DNA
<213> ORGANISM: Homo sapiens

<400> SEQUENCE: 2
```

| | | | | | |
|---|---|---|---|---|---|
| gaggctttaa | aatcttttt | catcttctag | ctgtagctcg | ggctgcttgt | cggcttggcc | 60 |
| tcccctccc | cctttgctc | tctgcctcgt | ctttccccag | gacttcgcta | ttttgctttt | 120 |
| ttaaaaaag | gcaagaaaga | actaaactcc | ccctccctc | tcctccagtc | gggctgcacc | 180 |
| tctgccttgc | actttgcaca | gaggtagaga | gcgcgcgagg | gagagagagg | aaagaaaaaa | 240 |
| aataataaag | agagccaagc | agaagaggag | gcgagaagca | tgaagtgtta | actccccgt | 300 |
| gccaaggccc | gcgccgcccg | gacagacgcc | cgccgcgcct | ccagccccga | gcggacgccg | 360 |
| cgcgcgccct | gcctgcagcc | cgggccggcg | aggcgagccc | ttccttatgc | aaagcgcgca | 420 |
| gcggagcggc | gagcggggga | cgccgcgcac | cgggccgggc | tcctccagct | tcgccgccgc | 480 |
| agccaccacc | gccgccaccg | cagctcgcgg | aggatcttcc | cgagcctgaa | gccgccggct | 540 |
| cggcgcgcaa | ggaggcgagc | gagcaaggag | gggccggggc | gagcgaggga | gcacattggc | 600 |
| gtgagcaggg | gggagggagg | gcgggcgcgg | ggggcgcggg | cagggcgggg | gggtgtgtgt | 660 |
| gtgagcgcgc | tcggaggttt | cgggccagcc | accgccgcgc | aagctagaag | cgccccagcc | 720 |
| cggcaagctg | gctcacccgc | tggccaccca | gcacagcccg | ctggcccctc | tcctgcagcc | 780 |
| catctggcgg | agcggcggcg | gcggcggcgg | cggcggcagg | agaatggcat | cagaactggc | 840 |
| aatgagcaac | tccgacctgc | ccaccagtcc | cctggccatg | gaatatgtta | atgacttcga | 900 |
| tctgatgaag | tttgaagtga | aaaggaacc | ggtggagacc | gaccgcatca | tcagccagtg | 960 |
| cggccgtctc | atcgccgggg | gctcgctgtc | ctccaccccc | atgagcacgc | cgtgcagctc | 1020 |
| ggtgcccct | tcccccagct | tctcggcgcc | cagcccgggc | tcgggcagcg | agcagaaggc | 1080 |
| gcacctggaa | gactactact | ggatgaccgg | ctacccgcag | cagctgaacc | ccgaggcgct | 1140 |
| gggcttcagc | cccgaggacg | cggtcgaggc | gctcatcagc | aacagccacc | agctccaggg | 1200 |
| cggcttcgat | ggctacgcgc | gcggggcgca | gcagctggcc | gcggcggccg | ggccggtgc | 1260 |
| cggcgcctcc | ttgggcggca | gcggcgagga | gatgggcccc | gccgccgccg | tggtgtccgc | 1320 |
| cgtgatcgcc | gcggccgccg | cgcagagcgg | cgcgggcccg | cactaccacc | accaccacca | 1380 |
| ccacgccgcc | ggccaccacc | accacccgac | ggccggcgcg | cccggcgccg | cgggcagcgc | 1440 |
| ggccgcctcg | gccggtggcg | ctgggggcgc | gggcggcggt | ggcccggcca | gcgctggggg | 1500 |
| cggcggcggc | ggcggcggcg | gcggaggcgg | cggggcgcg | gcggggcgg | ggggcgccct | 1560 |
| gcacccgcac | cacgccgccg | gcggcctgca | cttcgacgac | cgcttctccg | acagcagct | 1620 |
| ggtgaccatg | tctgtgcgcg | agctgaaccg | gcagctgcgc | ggggtcagca | aggaggaggt | 1680 |
| gatccggctg | aagcagaaga | ggcggaccct | gaaaaccgc | ggctatgccc | agtcctgccg | 1740 |
| cttcaagagg | gtgcagcaga | gacacgtcct | ggagtcggaa | agaaccagc | tgctgcagca | 1800 |
| agtcgaccac | ctcaagcagg | agatctccag | gctggtgcgc | gagagggacg | cgtacaagga | 1860 |
| gaaatacgag | aagttggtga | gcagcggctt | ccgagaaaac | ggctcgagca | gcgacaaccc | 1920 |
| gtcctctccc | gagtttttca | taactgagcc | cactcgcaag | ttggagccat | cagtgggata | 1980 |
| cgccacattt | tggaagcccc | agcatcgtgt | acttaccagt | gtgttcacaa | aatgaaattt | 2040 |
| gtgtgagagc | tgtacattaa | aaaaaatcat | cattattatt | attatttgca | gtcatggaga | 2100 |
| accacctacc | cctgacttct | gtttagtctc | cttttttaaat | aaaaattact | gtgttagaga | 2160 |

| | |
|---|---:|
| agaaggctat taaatgtagt agttaactat gcctcttgtc tggggtttc atagagaccg | 2220 |
| gtaggaaagc gcactcctgc ttttcgattt atggtgtgtg caagtaaaca ggtgcattgc | 2280 |
| tttcaacctg ccatactagt tttaaaaatt cactgaaatt acaaagatac atatatatgc | 2340 |
| atatatataa tggaaagttt cccggaatgc aacaattagc attttaaaat catatatagg | 2400 |
| catgcacatt ctaaatagta cttttcatg cttcattgtt tctctggcag ataattttac | 2460 |
| taagaagaaa aatagatatt cgactcccct tccctaaaca aatccacggg cagaggctcc | 2520 |
| agcggagccg agcccctgg ttttctcgta ggccctagac ggtgttgcat ttatcagtga | 2580 |
| tgtcaaacgt gctcatttgt cagacatagc tgtaaatgaa acaatgtgt ggcaaaatac | 2640 |
| aaagttaaaa aaaaaa | 2656 |

<210> SEQ ID NO 3
<211> LENGTH: 6887
<212> TYPE: DNA
<213> ORGANISM: Homo sapiens

<400> SEQUENCE: 3

| | |
|---|---:|
| gaggctttaa aatctttttt catcttctag ctgtagctcg ggctgcttgt cggcttggcc | 60 |
| tcccctccc cctttgctc tctgcctcgt cttcccag gacttcgcta ttttgctttt | 120 |
| ttaaaaaag gcaagaaaga actaaactcc cccctccctc tcctccagtc gggctgcacc | 180 |
| tctgccttgc actttgcaca gaggtagaga gcgcgcgagg gagagagagg aaagaaaaaa | 240 |
| aataataaag agagccaagc agaagaggag gcgagaagca tgaagtgtta actccccgt | 300 |
| gccaaggccc gcgccgcccg gacagacgcc cgccgcgcct ccagccccga gcggacgccg | 360 |
| cgcgcgccct gcctgcagcc cgggccggcg aggcgagccc ttccttatgc aaagcgcgca | 420 |
| gcggagcggc gagcggggga cgccgcgcac cgggccgggc tcctccagct tcgccgccgc | 480 |
| agccaccacc gccgccaccg cagctcgcgg aggatcttcc cgagcctgaa gccgccggct | 540 |
| cggcgcgcaa ggaggcgagc gagcaaggag gggccggggc gagcgaggga gcacattggc | 600 |
| gtgagcaggg gggagggagg gcgggcgcgg ggggcgcggg cagggcgggg gggtgtgtgt | 660 |
| gtgagcgcgc tcggaggttt cgggccagcc accgccgcgc aagctagaag cgccccagcc | 720 |
| cggcaagctg gctcacccgc tggccaccca gcacagcccg ctggcccctc tcctgcagcc | 780 |
| catctggcgg agcggcggcg gcggcggcgg cggcggcagg agaatggcat cagaactggc | 840 |
| aatgagcaac tccgacctgc ccaccagtcc cctggccatg gaatatgtta atgacttcga | 900 |
| tctgatgaag tttgaagtga aaaggaacc ggtggagacc gaccgcatca tcagccagtg | 960 |
| cggccgtctc atcgccgggg gctcgctgtc ctccaccccc atgagcacgc cgtgcagctc | 1020 |
| ggtgccccct tccccagct tctcggccgc cagcccgggc tcgggcagcg agcagaaggc | 1080 |
| gcacctggaa gactactact ggatgaccgg ctacccgcag cagctgaacc ccgaggcgct | 1140 |
| gggcttcagc cccgaggacg cggtcgaggc gctcatcagc aacagccacc agctccaggg | 1200 |
| cggcttcgat ggctacgcgc gcggggcgca gcagctggcc gcggcggccg ggccggtgc | 1260 |
| cggcgcctcc ttgggcggca gcggcgagga gatgggcccc gccgccgccg tggtgtccgc | 1320 |
| cgtgatcgcc gcggccgccg cgcagagcgg cgcgggcccg cactaccacc accaccacca | 1380 |
| ccacgccgcc ggccaccacc acacccgac ggccggcgcg cccggcgccg cgggcagcgc | 1440 |
| ggccgcctcg gccggtggcg ctggggggcg gcggcggt ggcccggcca gcgctggggg | 1500 |
| cggcggcggc ggcggcggcg gcggaggcgg cggggcgcg gcggggcgg ggggcgccct | 1560 |
| gcacccgcac cacgccgccg gcggcctgca cttcgacgac cgcttctccg acgagcagct | 1620 |

```
ggtgaccatg tctgtgcgcg agctgaaccg gcagctgcgc ggggtcagca aggaggaggt    1680
gatccggctg aagcagaaga ggcggaccct gaaaaaccgc ggctatgccc agtcctgccg    1740
cttcaagagg gtgcagcaga gacacgtcct ggagtcggag aagaaccagc tgctgcagca    1800
agtcgaccac ctcaagcagg agatctccag gctggtgcgc gagagggacg cgtacaagga    1860
gaaatacgag aagttggtga gcagcggctt ccgagaaaac ggctcgagca gcgacaaccc    1920
gtcctctccc gagttttca tgtgagtctg acacgcgatt ccagctagcc accctgataa     1980
gtgctccgcg ggggtccggc tcgggtgtgg gcttgctagt tctagagcca tgctcgccac    2040
cacctcacca ccccaccccc caccgagttt ggccccttg gccccctaca cacacacaaa    2100
cccgcacgca cacaccacac acacacacac acacacacac acaccccaca ccctgctcga    2160
gtttgtggtg gtggtggctg ttttaaactg gggagggaat gggtgtctgg ctcatggatt    2220
gccaatctga aattctccat aacttgctag cttgtttttt ttttttttt acacccccc    2280
gccccacccc cggacttgca caatgttcaa tgatctcagc agagttcttc atgtgaaacg    2340
ttgatcacct ttgaagcctg catcattcac atattttttc ttcttcttcc ccttcagttc    2400
atgaactggt gttcatttc tgtgtgtgtg tgtgttttat tttgtttgga ttttttttt     2460
taatttact tttagagctt gctgtgttgc ccacctttt tccaacctcc accctcactc      2520
cttctcaacc catctcttcc gagatgaaag aaaaaaaaaa gcaaagtttt tttttcttct    2580
cctgagttct tcatgtgaga ttgagcttgc aaaggaaaaa aaaatgtgaa atgttataga    2640
cttgcagcgt gccgagttcc atcgggtttt tttttagca ttgttatgct aaaatagaga    2700
aaaaaatcct catgaacctt ccacaatcaa gcctgcatca accttctggg tgtgacttgt    2760
gagttttggc cttgtgatgc caaatctgag agtttagtct gccattaaaa aaactcattc    2820
tcatctcatg cattattatg cttgctactt tgtcttagca acaatgaact ataactgttt    2880
caaagacttt atggaaaaga gacattatat taataaaaaa aaaaagcctg catgctggac    2940
atgtatggta taattatttt ttcctttttt tttcctttg gcttggaaat ggacgttcga    3000
agacttatag catggcattc atactttgt tttattgcct catgacttt ttgagtttag     3060
aacaaaacag tgcaaccgta gagccttctt cccatgaaat tttgcatctg ctccaaaact    3120
gctttgagtt actcagaact tcaacctccc aatgcactga aggcattcct tgtcaaagat    3180
accagaatgg gttacacatt taacctgcaa acattgaag aactcttaat gttttctttt     3240
taataagaat gacgccccac tttggggact aaaattgtgc tattgccgag aagcagtcta    3300
aaatttattt tttaaaaaga gaaactgccc cattattttt ggtttgtttt attttattt     3360
tatattttt ggcttttggt cattgtcaaa tgtggaatgc tctgggtttc tagtatataa     3420
tttaattcta gttttataa tctgttagcc cagttaaaat gtatgctaca gataaaggaa     3480
tgttatagat aaatttgaaa gagttaggtc tgtttagctg tagattttt aaacgattga     3540
tgcactaaat tgtttactat tgtgatgtta agggggtag agtttgcaag gggactgttt     3600
aaaaaagta gcttatacag catgtgcttg caacttaaat ataagttggg tatgtgtagt     3660
ctttgctata ccactgactg tattgaaaac caaagtatta agaggggaaa cgcccctgtt    3720
tatatctgta ggggtatttt acattcaaaa atgtatgttt ttttttcttt tcaaaattaa    3780
agtatttggg actgaattgc actaagatat aacctgcaag catataatac aaaaaaaaat    3840
tgcaaaactg tttagaacgc taataaaatt tatgcagtta taaaaatggc attactgcac    3900
agttttaaga tgatgcagat ttttttacag ttgtattgtg gtgcagaact ggattttctg    3960
taacttaaaa aaaaatccac agttttaaag gcaataatca gtaaatgtta ttttcaggga    4020
```

```
ctgacatcct gtctttaaaa agaaatgaaa agtaaatctt accacaataa atataaaaaa    4080
atcttgtcag ttacttttct tttacatatt ttgctgtgca aaattgtttt atatcttgag    4140
ttactaacta accacgcgtg ttgttcctat gtgcttttct ttcattttca attctggtta    4200
tatcaagaaa agaataatct acaataataa acggcatttt tttttgattc tgtactcagt    4260
ttcttagtgt acagtttaac tgggcccaac aacctcgtta aaagtgtaaa atgcatcctt    4320
ttctccagtg gaaggattcc tggaggaata gggagacagt aattcagggt gaaattatag    4380
gctgtttttt gaagtgagga ggctggcccc atatactgat tagcaatatt taatatagat    4440
gtaaattatg acctcatttt tttctcccca aagttttcag ttttcaaatg agttgagcca    4500
taattgccct tggtaggaaa acaaaacaa aacagtggaa ctaggcttcc tgagcatggc     4560
cctacacttc tgatcaggag caaagccatc catagacaga ggagccggac aaatatggcg    4620
catcagaggt ggcttgcgca catatgcatt gaacggtaaa gagaaacagc gcttgccttt    4680
tcactaaagt tgactatttt tccttcttct cttacacacc gagattttct tgttagcaag    4740
gcctgacaag atttaacata aacatgacaa atcatagttg tttgttttgt tttgcttttc    4800
tcttaaacac tgaagatcat ttgtcttaaa taggaaaaag aaaatccact ccttacttcc    4860
atatttccaa gtacatatct ggtttaaact atgttatcaa atcatatttc accgtgaata    4920
ttcagtggag aacttctcta cctggatgag ctagtaatga tttcagatca tgctatcccc    4980
agaaataaaa gcaaaaaata ataccctgtgt ggaatatagg ctgtgctttg atttactggt    5040
atttacccca aaataggctg tgtatggggg ctgacttaaa gatcccttgg aaagactcaa    5100
aactaccttc actagtagga ctcctaagcg ctgacctatt tttaaatgac acaaattcat    5160
gaaactaatg ttacaaattc atgcagtttg cactcttagt catcttcccc tagcacacca    5220
atagaatgtt agacaaagcc agcactgttt tgaaaataca gccaaacacg atgacttttg    5280
ttttgttttc tgccgttctt aaaagaaaaa aagataatat tgcaactctg actgaaagac    5340
ttatttttaa gaaaacaggt tgtgtttggt gctgctaagt tctggccagt ttatcatctg    5400
gccttcctgc ctattttta caaaacacga agacagtgtg taacctcgac attttgacct    5460
tcctttatgt gctagtttag acaggctcct gaatccacac ttaattttgc ttaacaaaag    5520
tcttaatagt aaacctcccc tcatgagctt gaagtcaagt gttcttgact tcagatattt    5580
ctttcctttt tttttttttt tcctcatcac aactaagaga tacacaaact ctgaagaagc    5640
agaaatggag agaatgcttt taacaaaaaa gcatctgatg aaagatttta ggcaaacatt    5700
ctcaaaataa gagtgatatt ctggatgtag ttattgcagt tatctcatga caaatgaggc    5760
ctggattgga aggaaaatat agttgtgtag aattaagcat tttgatagga atctacaagg    5820
tagttgaata taataagcag gtttgggccc ccaaacttta gaaaatcaaa tgcaaaggtg    5880
ctggcaaaaa tgaggtttga gtggctggct gtaagagaag gttaactcct agtaaaaggc    5940
atttttagaa ataacaatta ctgaaaactt tgaagtatag tgggagtagc aaacaaaatac   6000 atgttttttt tttcttacaa agaactccta aatcctgagt aagtgccatt cattacaata    6060
agtctctaaa tttaaaaaaa aaaaatcat atgaggaaat ctagctttcc cctttacgct     6120
gcgtttgatc tttgtctaaa tagtgttaaa attcctttca ttccaattac agaactgagc    6180
ccactcgcaa gttggagcca tcagtgggat acgccacatt ttggaagccc cagcatcgtg    6240
tacttaccag tgtgttcaca aaatgaaatt tgtgtgagag ctgtacatta aaaaaaatca    6300
tcattattat tattatttgc agtcatggag aaccacctac ccctgacttc tgtttagtct    6360
cctttttaaa taaaaattac tgtgttagag aagaaggcta ttaaatgtag tagttaacta    6420
```

-continued

```
tgcctcttgt ctgggggttt catagagacc ggtaggaaag cgcactcctg cttttcgatt    6480
tatggtgtgt gcaagtaaac aggtgcattg ctttcaacct gccatactag ttttaaaaat    6540
tcactgaaat tacaaagata catatatatg catatatata atggaaagtt tcccggaatg    6600
caacaattag cattttaaaa tcatatatag gcatgcacat tctaaatagt acttttttcat   6660 gcttcattgt ttctctggca gataatttta ctaagaagaa aaatagatat tcgactcccc    6720
ttccctaaac aaatccacgg gcagaggctc cagcggagcc gagcccctg gtttttctcgt    6780 aggccctaga cggtgttgca tttatcagtg atgtcaaacg tgctcatttg tcagacatag    6840
ctgtaaatga aacaatgtg tggcaaaata caaagttaaa aaaaaaa                    6887
```

```
<210> SEQ ID NO 4
<211> LENGTH: 400
<212> TYPE: PRT
<213> ORGANISM: Homo sapiens

<400> SEQUENCE: 4

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
                20                  25                  30

Lys Lys Glu Pro Val Glu Thr Asp Arg Ile Ile Ser Gln Cys Gly Arg
            35                  40                  45

Leu Ile Ala Gly Gly Ser Leu Ser Ser Thr Pro Met Ser Thr Pro Cys
        50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
            100                 105                 110

Ala Val Glu Ala Leu Ile Ser Asn Ser His Gln Leu Gln Gly Gly Phe
        115                 120                 125

Asp Gly Tyr Ala Arg Gly Ala Gln Gln Leu Ala Ala Ala Gly Ala
    130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190

His His Pro Thr Ala Gly Ala Pro Gly Ala Ala Gly Ser Ala Ala Ala
        195                 200                 205

Ser Ala Gly Gly Ala Gly Ala Gly Gly Gly Pro Ala Ser Ala
    210                 215                 220

Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
            260                 265                 270

Glu Leu Asn Arg Gln Leu Arg Gly Val Ser Lys Glu Glu Val Ile Arg
        275                 280                 285
```

```
Leu Lys Gln Lys Arg Arg Thr Leu Lys Asn Arg Gly Tyr Ala Gln Ser
            290                 295                 300

Cys Arg Phe Lys Arg Val Gln Arg His Val Leu Glu Ser Glu Lys
305                 310                 315                 320

Asn Gln Leu Leu Gln Gln Val Asp His Leu Lys Gln Glu Ile Ser Arg
                    325                 330                 335

Leu Val Arg Glu Arg Asp Ala Tyr Lys Glu Lys Tyr Glu Lys Leu Val
                340                 345                 350

Ser Ser Gly Phe Arg Glu Asn Gly Ser Ser Asp Asn Pro Ser Ser
                355                 360                 365

Pro Glu Phe Phe Ile Thr Glu Pro Thr Arg Lys Leu Glu Pro Ser Val
370                 375                 380

Gly Tyr Ala Thr Phe Trp Lys Pro Gln His Arg Val Leu Thr Ser Val
385                 390                 395                 400

<210> SEQ ID NO 5
<211> LENGTH: 373
<212> TYPE: PRT
<213> ORGANISM: Homo sapiens

<400> SEQUENCE: 5

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
                20                  25                  30

Lys Lys Glu Pro Val Glu Thr Asp Arg Ile Ile Ser Gln Cys Gly Arg
                35                  40                  45

Leu Ile Ala Gly Gly Ser Leu Ser Ser Thr Pro Met Ser Thr Pro Cys
50                  55                  60

Ser Ser Val Pro Pro Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
                100                 105                 110

Ala Val Glu Ala Leu Ile Ser Asn Ser His Gln Leu Gln Gly Gly Phe
                115                 120                 125

Asp Gly Tyr Ala Arg Gly Ala Gln Gln Leu Ala Ala Ala Gly Ala
                130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                    165                 170                 175

Ala Gly Pro His Tyr His His His His His Ala Ala Gly His His
                180                 185                 190

His His Pro Thr Ala Gly Ala Pro Gly Ala Ala Gly Ser Ala Ala Ala
                195                 200                 205

Ser Ala Gly Gly Ala Gly Gly Ala Gly Gly Gly Pro Ala Ser Ala
210                 215                 220

Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
                260                 265                 270
```

```
Glu Leu Asn Arg Gln Leu Arg Gly Val Ser Lys Glu Val Ile Arg
            275                 280                 285

Leu Lys Gln Lys Arg Arg Thr Leu Lys Asn Arg Gly Tyr Ala Gln Ser
    290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
            340                 345                 350

Ser Ser Gly Phe Arg Glu Asn Gly Ser Ser Ser Asp Asn Pro Ser Ser
            355                 360                 365

Pro Glu Phe Phe Met
    370

<210> SEQ ID NO 6
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 6
acggcucgag cagcgacaa                                                  19

<210> SEQ ID NO 7
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 7
cuuaccagug uguucacaa                                                  19

<210> SEQ ID NO 8
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 8
uggaagacua cuacuggaug                                                 20

<210> SEQ ID NO 9
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 9
auuugcaguc auggagaacc                                                 20

<210> SEQ ID NO 10
<211> LENGTH: 20
<212> TYPE: RNA
<213> ORGANISM: Artificial Sequence
<220> FEATURE:
<223> OTHER INFORMATION: c-MAF specific siRNA
```

-continued

```
<400> SEQUENCE: 10
caaggagaaa uacgagaagu                                                    20

<210> SEQ ID NO 11
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 11
acaaggagaa auacgagaag                                                    20

<210> SEQ ID NO 12
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 12
accuggaaga cuacuacugg                                                    20

<210> SEQ ID NO 13
<211> LENGTH: 13878
<212> TYPE: DNA
<213> ORGANISM: Homo sapiens

<400> SEQUENCE: 13
aactatatat taaacacctc cggtctgaga ggccgtgttg ggtgtctttg tcaggtgaag        60
aaagagaaga aggctggtac accttcccag gaattctcac tgaagaaaac atctggattt      120
tttacatctc ttgtgcaaaa caaacaaaga tttcattaag tgatgtatat tgttttccaa      180
ggaagaaacc tgcagagaca aaaacaaata agcaaataat tgaaacaaaa atatgataaa      240
cccccaaatt cttccagtgc taatttactt gttatcatgg ttctctacaa aggcagagat      300
cactaattac aggttttttcc agaattcaca tttcacgtca agatcatcca atccaaacag     360
tgtacggaaa gcctagggcc ttcttcactt tgccccctac cccaccctac acacacgccc      420
ccatctaaat gataccctytg gaaagaaacc tacacatctc atttgtctat attttgcttc     480
ctccctcgcc tccggtaac caaatgtgag ttgttctcta actgcactgg agaatcagaa       540
tttattgtac atatgtttgt gttccactta ataaaaaaac ctatatttta agataaactt      600
tgttagtaat tcatgaggta agtgactatt atgctaatc aggcagaaat atattctcaa       660
gcataatgca ttacataaat ttgaatgtaa aatgttcaat tatgaagtaa atacaggtaa      720
tgcaaataat aaaattacctc taataaaaat tataaaagat gtgccttgaa agagagagcg     780
gctttaactt acaactgtga attgcttaaa gagaaaagaa ttaataaatg ctgaattact      840
ctgatgatta tttagcacat aattcaccta ttcataacga ctcctagtaa tcagactgtt      900
gtttcacatc ctccaacatg aggcaagact gtttcctcag caattttgcc cttatcagat      960
tatctcgtct gattctatta atttttcttcc atgaatctgc taacagtgat ttgtgattta   1020
cttaccctgc taactgaaga ctgttaaaag gattatcta acactggacc taagaacagt     1080
gtacgcctta tcgttcagtt actctgaaga actctttctc aaatcaattt agttggtttc    1140
atagtgaaat ttagtggaca ctggttagtt ctgccccata aaatcagccc ctaaacaaag    1200
agtccagaca ccatacctga tgcatccatt tctattcaga ttatggatgt ctgattccaa    1260
catgatatat ttgagttgct ataactcaca atcggggaaa atatattcct ttaagctttt    1320
```

```
aatctttgta atttggacat gaacagggt  tttgttttc  attttgcat  gaagtcatta  1380
tgtatgtact gacgtgaaac tataattgtg tttctgatgt tactgtgtca caatattcta  1440
tgcgatgtaa cccatgtcct cctcccctc  acaaatctcc tataaatatt cattgctttc  1500
aaaaactta  atactactgg tccgaattgg tcaataatga caaatgcatg gtttctaaat  1560
tactgtatat tgttctacag agattactag agtatatata gcaagggat  gttaagcagt  1620
aagaaaacac agttcacatt gtatttggat tagattggct tggatagaag tgaaacaaac  1680
aatgttagca aagaagtcta aagacatgtg gcccactgta attgtacaga atcaaaaacc  1740
tgaatagtac tcattaaaat gagagagctc aattgttata aagaaatgc  tgctaacaga  1800
gaactgtaaa tgtttagaca cccctgtgaa tcactaaata ataatgtaaa aaggataaaa  1860
atgagaatta agttataagc ctgagagcat tactgctaca catctaaaaa aataattctg  1920
atcctctctt ttttttttcc aagagaaaat gggcgactat aaaagaacctt gcaataagag  1980
aaataaaaat accatgtctt cacagcagtg tacataaata aaccataaaa atgtgcagat  2040
aataatatat ttagctgccc aaacatgggc atttaatttc tagaaatgat atataacaat  2100
gtaacaatta gatactcagc catgaatgtg tatggcacag tcttcatcat tagcaaactt  2160
tgtgtataaa atattattta ttatttatta taatactgct ttcagaggca atgatcatac  2220
cttacagctt ttaacacaaa tatgatgcaa aaggattaaa agtatatcat aaacaaacaa  2280
taaattcttt ctaaatacac ttaaattcat attttacatg aaaatataa  acttcctaca  2340
tttgtgacta ctgactttta aaagaccta  gaaaactatt gttacgggca atgttaaatg  2400
acataatgct tatgtaatgg aaagtgtgga ttttcctcta aataaactat aatcccttaa  2460
cttcattact agggaaaata ttgttaaaga gaaggaaagc aagggaattc tgctaggttg  2520
cataaatatt gacataatct tcactctttc ttccccaaac tggtaataga catagtttat  2580
tccacccaac aaaatgctct tataagacca aaactaccct tattaacaac ttctctgcag  2640
tcacgatgaa aagaaacact acttgtctga aaaataccga cagcgctgcc ttttcagat   2700
tagggtgtgc ctacgaatct tttgggaagt cttccattaa ggattcctgg gtttgctgaa  2760
actgaagtct actaggatca gagaaattaa cacaggtcta atatggtgca aggaacgagt  2820
gagagacacc tgaggttata aatagcaaag catgctgcgg ggtggggaag accattctga  2880
agtgcaatgt tcaagacgct ggcttaatat atgactaagt gtcagaagtc aggttttctg  2940
agaattactt tccagataaa caactttata gcactgcact taatcttact tactagagac  3000
atctcattta tcactgaatt acaagtaact ttaatcctat tgatattgcc ataaagcccg  3060
ttgaaaatcc atcctggcac ttttaagg   tttggggccc tgttacatgg ggatcctctt  3120
gcaaggtct  cagccagaaa ttacaccccg agggtgtctg tatccctgg  cctctttgtc  3180
aacaatcaag gagaagagga ggggcaaaaa tgatctctgc atctgccagc actttcttcg  3240
gcccctttcc tatagggtcg ggttctccca cttcagtcaa actaactttg tgtgtctctt  3300
tcctcctccc acactgggta accagctgct tttcacttca tcgacaaaac tggacacgga  3360
tcaatttcaa ctgacctttg ccgaaaggtg gcgctgttga ggtaaaaacc aactcgctcc  3420
aacaatagtt tccactcttc gatccttttg caggcttttc agaatttttt ttttttttta  3480
atgcacccctc ctagcgtctc ccccttctca taaagtaaaa taaatacgat taaaaacacc  3540
aaatgcattt cattaattga aggaatcaac agtcccaact tctaagcaga cgggctggtc  3600
ttccaaaggc tgggtcggtt tcaggagctt tctctccaaa taaatctctg cttcttcgac  3660
ttgcctatcg ctttaaaatc ttagaaacag agttagttgt tggtttcctt cttttttctt  3720
```

-continued

```
tttcttttttt atttcttttt tgcataaact tttagagaat caatctagaa atttgaacta    3780
cttattagca tttgcaactg ggggtggggg gagcagcctc ccccacccca cccccactc      3840
tgcgtttccg gactagttcc agaaaccgcg gtttaaaatt taaccctccg agggtagctg    3900
gtgagggctg gggtattgtt tttccccctt gctccctgcc acgatcaagt ccgaaataat    3960
taaaggaaac gtaaaagtgc aaagggcgcg cctgaccctg ataaacagag gtcagatttc    4020
gtaaggggac gggtgagtgt gagtgtgtgt gtgtttgtgt gtgtgtgtgt aagagagaga    4080
gagagcgagc gcgcaatatg agtctcaaag gccaaactcc ggccagtcag gagccggaag    4140
gctgagcccg gctgacctga ctttgagctt ccccggagtt atctcgcata ggcgctcgct    4200
ctgtccaagg gcacgcgacg ccagcgggca gccggtctcc gtgaagaatg gcctctaaac    4260
aacttatttt acctcgttgt aaagagaggg ataaaatggg ctttccctct ccacggatgc    4320
ccagccttct gggcaggcgc atggccgggc ggcgcccagc ccgcagcccc gatccggaca    4380
ccccactgca tccctccctt cccggtccct tccccgcacg ggcgcccgag agacggacaa    4440
agagttgggg ccaagtttga gcgccgggca cggccaggct cagggaagga aggtccccgg    4500
cagacacctg ggtaccagag ttggtgcgag gaggaaaagc tgggaggcga attcacaatc    4560
ctggggtgg agggcaggca ggggagggga atcaggccaa tcccagccga gtgagccccc    4620
agcgagctgg ggctccggat gggaggcctg tctcgcgctc caaagaaaag caaaccgccc    4680
tcccaggtcc gcccggattg ccgaagcccc tctggaaaaa ctccttcccc tcttacacca    4740
aactttgcgc cgggcctcgt tccctcccgg gtaggcagcg gcgcaggaag ggttaagcca    4800
gcccgtccca gctgacagtc agctgattgg gccctgattg acagtccga aaagtttcct    4860
tgtttctata ctattatgct aatcgcggcc gctctcgccg cctcccattg gcccggagtg    4920
ccagtcaatt tctcatttgg acctgacgtc acgagtgcta taaaactcag caattgcttt    4980
aaactcttct tgctggatca gaggctttaa aatcttttt catcttctag ctgtagctcg    5040
ggctgcttgt cggcttggcc tccccctccc ccctttgctc tctgcctcgt ctttccccag    5100
gacttcgcta ttttgctttt ttaaaaaaag gcaagaaaga actaaactcc cccctccctc    5160
tcctccagtc gggctgcacc tctgccttgc actttgcaca gaggtagaga gcgcgcgagg    5220
gagagagagg aaagaaaaaa aataataaag agagccaagc agaagaggag gcgagaagca    5280
tgaagtgtta actcccccgt gccaaggccc gcgccgcccg gacagacgcc cgccgcgcct    5340
ccagccccga gcggacgccg cgcgcgccct gcctgcagcc cgggccggcg aggcgagccc    5400
ttccttatgc aaagcgcgca gcggagcggc gagcggggga cgccgcgcac cgggccgggc    5460
tcctccagct tcgccgccgc agccaccacc gccgccaccg cagctcgcgg aggatcttcc    5520
cgagcctgaa gccgccggct cggcgcgcaa ggaggcgagc gagcaaggag gggccggggc    5580
gagcgaggga gcacattggc gtgagcaggg gggagggagg gcgggcgcgg ggggcgcggg    5640
cagggcgggg gggtgtgtgt gtgagcgcgc tcggagtttt cggccagcc accgccgcgc    5700
aagctagaag cgccccagcc cggcaagctg gctcacccgc tggccaccca gcacagcccg    5760
ctggcccctc tcctgcagcc catctggcgg agcggcggcg gcgcggcggcg cggcggcagg    5820
agaatggcat cagaactggc aatgagcaac tccgacctgc caccagtcc cctgccatg     5880
gaatatgtta atgacttcga tctgatgaag tttgaagtga aaaggaacc ggtggagacc     5940
gaccgcatca tcagccagtg cggccgtctc atcgccgggg gctcgctgtc ctccacccc    6000
atgagcacgc cgtgcagctc ggtgcccct tccccagct tctcggcgcc cagcccgggc    6060
tcgggcagcg agcagaaggc gcacctggaa gactactact ggatgaccgg ctacccgcag    6120
```

```
cagctgaacc ccgaggcgct gggcttcagc cccgaggacg cggtcgaggc gctcatcagc    6180
aacagccacc agctccaggg cggcttcgat ggctacgcgc gcggggcgca gcagctggcc    6240
gcggcggccg gggccggtgc cggcgcctcc ttgggcggca gcggcgagga gatgggcccc    6300
gccgccgccg tggtgtccgc cgtgatcgcc gcggccgccg cgcagagcgg cgcgggcccg    6360
cactaccacc accaccacca ccacgccgcc ggccaccacc accacccgac ggccggcgcg    6420 cccgcgccg cggcagcgc ggccgcctcg gccggtggcg ctgggggcgc gggcggcggt      6480
ggcccggcca gcgctggggg cggcggcggc ggcggcggcg gcggaggcgg cggggggcgcg   6540 gcggggggcgg ggggcgccct gcacccgcac cacgccgccg gcggcctgca cttcgacgac   6600
cgcttctccg acgagcagct ggtgaccatg tctgtgcgcg agctgaaccg gcagctgcgc    6660
ggggtcagca aggaggaggt gatccggctg aagcagaaga gcggaccct gaaaaaccgc     6720 ggctatgccc agtcctgccg cttcaagagg gtgcagcaga gacacgtcct ggagtcggag    6780
aagaaccagc tgctgcagca agtcgaccac ctcaagcagg agatctccag gctggtgcgc    6840
gagagggacg cgtacaagga gaaatacgag aagttggtga gcagcggctt ccgagaaaac    6900
ggctcgagca gcgacaaccc gtcctctccc gagttttca tgtgagtctg acacgcgatt     6960
ccagctagcc accctgataa gtgctccgcg ggggtccggc tcgggtgtgg gcttgctagt    7020
tctagagcca tgctcgccac cacctcacca ccccaccccc caccgagttt ggccccccttg   7080 gcccctaca cacacacaaa cccgcacgca cacaccacac acacacacac acacacacac    7140 acacccaca ccctgctcga gtttgtggtg gtggtggctg ttttaaactg gggagggaat    7200
gggtgtctgg ctcatggatt gccaatctga aattctccat aacttgctag cttgttttt    7260 ttttttttt acacccccc gccccacccc cggacttgca caatgttcaa tgatctcagc     7320
agagttcttc atgtgaaacg ttgatcacct ttgaagcctg catcattcac atatttttc    7380 ttcttcttcc ccttcagttc atgaactggt gttcattttc tgtgtgtgtg tgtgttttat   7440
tttgtttgga tttttttttt taattttact tttagagctt gctgtgttgc ccaccttttt   7500
tccaacctcc accctcactc cttctcaacc catctcttcc gagatgaaag aaaaaaaaaa   7560
gcaaagtttt ttttcttct cctgagttct tcatgtgaga ttgagcttgc aaaggaaaaa   7620
aaaatgtgaa atgttataga cttgcagcgt gccgagttcc atcgggtttt tttttagca   7680 ttgttatgct aaaatagaga aaaaaatcct catgaacctt ccacaatcaa gcctgcatca   7740
accttctggg tgtgacttgt gagttttggc cttgtgatgc caaatctgag agtttagtct   7800
gccattaaaa aaactcattc tcatctcatg cattattatg cttgctactt tgtcttagca   7860
acaatgaact ataactgttt caaagacttt atggaaaaga gacattatat taataaaaaa   7920
aaaaagcctg catgctggac atgtatggta taattatttt ttccttttt tttccttttg   7980 gcttggaaat ggacgttcga agacttatag catggcattc atacttttgt tttattgcct   8040
catgactttt ttgagtttag aacaaaacag tgcaaccgta gagccttctt cccatgaaat   8100
tttgcatctg ctccaaaact gctttgagtt actcagaact tcaacctccc aatgcactga   8160
aggcattcct tgtcaaagat accagaatgg gttacacatt taacctggca acattgaag    8220 aactcttaat gttttctttt taataagaat gacgccccac tttggggact aaaattgtgc   8280
tattgccgag aagcagtcta aaatttattt tttaaaaaga gaaactgccc cattattttt   8340
ggtttgtttt attttattt tatatttttt ggcttttggt cattgtcaaa tgtggaatgc    8400
tctgggtttc tagtatataa tttaattcta gttttttataa tctgttagcc cagttaaaat  8460
gtatgctaca gataaaggaa tgttatagat aaatttgaaa gagttaggtc tgtttagctg   8520
```

-continued

```
tagattttttt aaacgattga tgcactaaat tgtttactat tgtgatgtta agggggggtag    8580 agtttgcaag gggactgttt aaaaaaagta gcttatacag catgtgcttg caacttaaat    8640
ataagttggg tatgtgtagt ctttgctata ccactgactg tattgaaaac caaagtatta    8700 agagggaaa cgcccctgtt tatatctgta ggggtatttt acattcaaaa atgtatgttt    8760
ttttttcttt tcaaaattaa agtatttggg actgaattgc actaagatat aacctgcaag    8820
catataatac aaaaaaaaat tgcaaaactg tttagaacgc taataaaatt tatgcagtta    8880
taaaaatggc attactgcac agttttaaga tgatgcagat ttttttacag ttgtattgtg    8940
gtgcagaact ggattttctg taacttaaaa aaaaatccac agttttaaag gcaataatca    9000
gtaaatgtta ttttcaggga ctgacatcct gtctttaaaa agaaatgaaa agtaaatctt    9060
accacaataa atataaaaaa atcttgtcag ttacttttct tttacatatt ttgctgtgca    9120
aaattgtttt atatcttgag ttactaacta accacgcgtg ttgttcctat gtgcttttct    9180
ttcattttca attctggtta tatcaagaaa agaataatct acaataataa acggcattttt    9240 ttttttgattc tgtactcagt ttcttagtgt acagtttaac tgggcccaac aacctcgtta    9300
aaagtgtaaa atgcatcctt ttctccagtg gaaggattcc tggaggaata gggagacagt    9360
aattcagggt gaaattatag gctgtttttt gaagtgagga ggctggcccc atatactgat    9420
tagcaatatt taatatagat gtaaattatg acctcatttt tttctcccca aagttttcag    9480
ttttcaaatg agttgagcca taattgccct tggtaggaaa aacaaaacaa aacagtggaa    9540
ctaggcttcc tgagcatggc cctacacttc tgatcaggag caaagccatc catagacaga    9600
ggagccggac aaatatggcg catcagaggt ggcttgcgca catatgcatt gaacggtaaa    9660
gagaaacagc gcttgccttt tcactaaagt tgactatttt tccttcttct cttacacacc    9720
gagattttct tgttagcaag gcctgacaag atttaacata aacatgacaa atcatagttg    9780
tttgttttgt tttgcttttc tctttaacac tgaagatcat ttgtcttaaa taggaaaaag    9840
aaaatccact ccttacttcc atatttccaa gtacatatct ggtttaaact atgttatcaa    9900
atcatatttc accgtgaata ttcagtggag aacttctcta cctggatgag ctagtaatga    9960
tttcagatca tgctatcccc agaaataaaa gcaaaaaata ataccttgtgt ggaatatagg    10020 ctgtgctttg atttactggt atttacccca aaataggctg tgtatggggg ctgacttaaa    10080
gatcccttgg aaagactcaa aactaccttc actagtagga ctcctaagcg ctgacctatt    10140
tttaaatgac acaaattcat gaaactaatg ttacaaattc atgcagtttg cactcttagt    10200
catcttcccc tagcacacca atagaatgtt agacaaagcc agcactgttt tgaaaataca    10260
gccaaacacg atgactttttg ttttgttttc tgccgttctt aaaagaaaaa aagataatat    10320
tgcaactctg actgaaagac ttatttttaa gaaaacaggt tgtgtttggt gctgctaagt    10380
tctggccagt ttatcatctg gccttcctgc ctatttttta caaaacacga agacagtgtg    10440
taacctcgac atttttgacct tccttttatgt gctagtttag acaggctcct gaatccacac    10500
ttaattttgc ttaacaaaag tcttaatagt aaacctcccc tcatgagctt gaagtcaagt    10560
gttcttgact tcagatattt ctttcctttt ttttttttttt tcctcatcac aactaagaga    10620
tacacaaact ctgaagaagc agaaatggag agaatgcttt taacaaaaaa gcatctgatg    10680
aaagatttta ggcaaacatt ctcaaaataa gagtgatatt ctggatgtag ttattgcagt    10740
tatctcatga caaatgaggc ctggattgga aggaaaatat agttgtgtag aattaagcat    10800
tttgatagga atctacaagg tagttgaata taataagcag gtttgggccc ccaaacttta    10860
gaaaatcaaa tgcaaaggtg ctggcaaaaa tgaggtttga gtggctggct gtaagagaag    10920
```

```
gttaactcct agtaaaaggc attttttagaa ataacaatta ctgaaaactt tgaagtatag   10980
tgggagtagc aaacaaatac atgttttttt tttcttacaa agaactccta aatcctgagt   11040
aagtgccatt cattacaata agtctctaaa tttaaaaaaa aaaaaatcat atgaggaaat   11100
ctagctttcc cctttacgct gcgtttgatc tttgtctaaa tagtgttaaa attcctttca   11160
ttccaattac agaactgagc ccactcgcaa gttggagcca tcagtgggat acgccacatt   11220
ttggaagccc cagcatcgtg tacttaccag tgtgttcaca aaatgaaatt tgtgtgagag   11280
ctgtacatta aaaaaaatca tcattattat tattatttgc agtcatggag aaccacctac   11340
ccctgacttc tgtttagtct ccttttaaa taaaaattac tgtgttagag aagaaggcta   11400
ttaaatgtag tagttaacta tgcctcttgt ctggggtttt catagagacc ggtaggaaag   11460
cgcactcctg cttttcgatt tatggtgtgt gcaagtaaac aggtgcattg ctttcaacct   11520
gccatactag ttttaaaaat tcactgaaat tacaaagata catatatatg catatatata   11580
atggaaagtt tcccggaatg caacaattag catttttaaaa tcatatatag gcatgcacat   11640
tctaaatagt acttttttcat gcttcattgt ttctctggca gataattttta ctaagaagaa   11700 aaatagatat tcgactcccc ttccctaaac aaatccacgg gcagaggctc cagcggagcc   11760 gagcccctg gttttctcgt aggccctaga cggtgttgca tttatcagtg atgtcaaacg   11820
tgctcatttg tcagacatag ctgtaaatga aacaatgtg tggcaaaata caaagttagt   11880
taaatacaca ccctctgtgt gattttttgc tccctttttct tttttgctcc tactcaaaaa   11940
aaaaaaaatc acctcctttta catttccctg gcttcttgca tgtttcccctt ttcaaaaacc   12000 atgtaataat tttttacaat gtatctgaca cattaatata ttgacatcaa ataggcagac   12060
attctacttt tgcctggcaa ataaatctgc tacggagaca tcatttcctc actgtctcaa   12120
agccataact acctgggagt ctttcaacac agacccctcc gatgggaaat gctgtttatt   12180
actgaatgca ggatgctcac gctctgatct tttctccctt gtgcctttac cccagtcatt   12240
tttacttagc aacaccaatt ctagatactt ctgttctgaa gtagaaccac ccccttgcca   12300
cactgccagt tttcctgcta aaagcagtgg acagaagaca gatcatggtc accctcacaa   12360
acatggcaca cagctgtctc ggtagctgca ttcccagcat gtcctggtct aaatatctag   12420
agttgcctat gacacgttca aaggttccca agcacagtac attgggaggc ttttgctgct   12480
gtggccgttg ttttcgttta ggccaactta cttccgtatt cacatactct ggctttacg   12540 aaatacactc ctccagtcta ctaggccaat caatatattt aaaagtctga ttgccacata   12600
agtctctctc tctctcttttt tgttttttgt ttgtttgttt tttctgtttt tggctgccgg   12660
tagttaaaga ctgagatagg ttggaagact aaaatacagg agtacatgag tgacaacctt   12720
cagccgtctg atttccatgc cggtaaaaca cacaaccaag ctcttcttag cgctgctaat   12780
ataaacattc actaagaggg aataggaagt gagatttacc agcttcactt tgctgatttg   12840
caaggttccc cactacgatt cactgtcatt tgattttga aaaataattt tgtccgtctc   12900
tttgaagaaa tgtcttagtt cttttatttt gtttgtttgg ttttttttag agaagtttta   12960
tctgcagtga taggctacaa ttttatctc cgctgattat ttgtcaggat gctgaatgaa   13020
taatttggtc ctgtgccttc cttgttgttc tgaggaaaat aagagaaact tggaagtttg   13080
tttcactctt agcccatcct aaatctaaaa gaagatgtcc caggtccagg caggccatgt   13140
agtagttata aaggaggtgg tccaggtcca gccacctcaa tcaggatttg tttgttttga   13200
agcatttgct taaaagcgga gcaagagtct taacccaact tgccataaca ctgctttttct   13260 cgcttttgat gtaaatcttc aaaattcaga catcaaacag ccccagaaaa ggggaattct   13320
```

```
ctccaggcat tgctccgccc cagctcctga acaaacccag ctctgtctag cattttttc   13380 cctagcgggg gtaggggaca gggtgagaga atttcagtct cccaggctgt ctcatgattg   13440
ttagggcata agaaacaca gtcctgccac aaattgggag catctttacc ctttagagag    13500
aaacaaaaca aaactaaaca aacaaatcaa attgctttgc atgaaggcgt agcaaataaa   13560
atctcgggct ccctgttccc tgcaccattt gtaggaggtg agaaatgagg gaaacaagag   13620 aaagggaac tttaaaagcg ggaggcccag aaataatccc tgttaccagt ctgaatttca    13680
cttgctccgt ggctaacgtc agacctagtg tgcatgtatg ccagaagtaa actaggctcg   13740
gctgtccatt tctttaaaat atgttccat gtttcctttt tgaaaacaat tttggggact    13800
aaacccaaat ggagagattt gaggaaatcg ttaatgtctt aacatttgag tatatttata   13860
aatgtatcag tctgtgat                                                 13878
```

```
<210> SEQ ID NO 14
<211> LENGTH: 455
<212> TYPE: PRT
<213> ORGANISM: Artificial Sequence
<220> FEATURE:
<223> OTHER INFORMATION: INB-1-11-8 (H1) Heavy Chain
<220> FEATURE:
<221> NAME/KEY: MISC_FEATURE
<222> LOCATION: (1)..(132)
<223> OTHER INFORMATION: Variable Heavy Chain
<220> FEATURE:
<221> NAME/KEY: MISC_FEATURE
<222> LOCATION: (133)..(138)
<223> OTHER INFORMATION: Start of constant region
<220> FEATURE:
<221> NAME/KEY: MISC_FEATURE
<222> LOCATION: (317)..(416)
<223> OTHER INFORMATION: Variant

<400> SEQUENCE: 14

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
                20                  25                  30

Gly Thr Pro Leu Thr Leu Thr Cys Thr Ala Ser Gly Phe Ser Leu Asn
            35                  40                  45

Asn Tyr Pro Met Thr Trp Val Arg Gln Ala Pro Gly Lys Gly Leu Asp
        50                  55                  60

Tyr Ile Gly Val Ile Asn Asn Ser Gly Glu Thr Ala Tyr Ala Thr Trp
65                  70                  75                  80

Ala Lys Arg Arg Phe Thr Ile Ser Arg Thr Ser Thr Thr Leu Tyr Leu
                85                  90                  95

Lys Ile Ala Ser Pro Thr Ile Glu Asp Thr Ala Thr Tyr Phe Cys Ala
            100                 105                 110

Arg Gly Gly Pro Val Ser Ser Asp Met Trp Gly Pro Gly Thr Leu Val
        115                 120                 125

Ile Val Ser Ser Gly Gln Pro Lys Ala Pro Ser Val Phe Pro Leu Ala
130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190
```

```
Gly Leu Tyr Ser Leu Ser Ser Val Ser Val Thr Ser Ser Ser Gln
            195                 200                 205

Pro Val Thr Cys Asn Val Ala His Pro Ala Thr Asn Thr Lys Val Asp
    210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
    275                 280                 285

Asn Glu Gln Val Arg Thr Ala Arg Pro Pro Leu Arg Glu Gln Gln Phe
290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
    355                 360                 365

Arg Ser Val Ser Leu Thr Cys Met Ile Asn Gly Phe Tyr Pro Ser Asp
370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
    435                 440                 445

Ile Ser Arg Ser Pro Gly Lys
    450                 455

<210> SEQ ID NO 15
<211> LENGTH: 132
<212> TYPE: PRT
<213> ORGANISM: Artificial Sequence
<220> FEATURE:
<223> OTHER INFORMATION: INB-1-11-8 (H1) Variable Heavy Chain

<400> SEQUENCE: 15

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Asn Tyr Pro Met Thr Trp Val Arg Gln Ala Pro Gly Lys Gly Leu Asp
    50                  55                  60

Tyr Ile Gly Val Ile Asn Asn Ser Gly Glu Thr Ala Tyr Ala Thr Trp
65                  70                  75                  80

Ala Lys Arg Arg Phe Thr Ile Ser Arg Thr Ser Thr Thr Leu Tyr Leu
                85                  90                  95
```

```
Lys Ile Ala Ser Pro Thr Ile Glu Asp Thr Ala Thr Tyr Phe Cys Ala
            100                 105                 110

Arg Gly Gly Pro Val Ser Ser Asp Met Trp Gly Pro Gly Thr Leu Val
        115                 120                 125

Ile Val Ser Ser
    130

<210> SEQ ID NO 16
<211> LENGTH: 236
<212> TYPE: PRT
<213> ORGANISM: Artificial Sequence
<220> FEATURE:
<223> OTHER INFORMATION: INB-1-11-8 (L4) Light Chain
<220> FEATURE:
<221> NAME/KEY: MISC_FEATURE
<222> LOCATION: (1)..(133)
<223> OTHER INFORMATION: Variable Light Chain
<220> FEATURE:
<221> NAME/KEY: MISC_FEATURE
<222> LOCATION: (134)..(139)
<223> OTHER INFORMATION: Start of constant region
<220> FEATURE:
<221> NAME/KEY: MISC_FEATURE
<222> LOCATION: (146)..(149)
<223> OTHER INFORMATION: Variant

<400> SEQUENCE: 16

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Val Val Gly Gly Thr Val Thr Ile Asn Cys Gln Ser Ser
        35                  40                  45

Gln Ser Val Tyr Arg Gly Asp Trp Leu Ala Trp Tyr Gln Gln Arg Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Ser Gly Ser Gly Thr His Phe Thr
                85                  90                  95

Leu Thr Ile Ser Asp Leu Asp Cys Asp Asp Ala Ala Thr Tyr Tyr Cys
            100                 105                 110

Ala Gly Gly Phe Ser Gly His Ile Tyr Asp Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235
```

```
<210> SEQ ID NO 17
<211> LENGTH: 133
<212> TYPE: PRT
<213> ORGANISM: Artificial Sequence
<220> FEATURE:
<223> OTHER INFORMATION: INB-1-11-8 (L4) Variable Light Chain

<400> SEQUENCE: 17

Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Ala Ser Pro
            20                  25                  30

Val Ser Ala Val Val Gly Gly Thr Val Thr Ile Asn Cys Gln Ser Ser
        35                  40                  45

Gln Ser Val Tyr Arg Gly Asp Trp Leu Ala Trp Tyr Gln Gln Arg Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Ser Gly Ser Gly Thr His Phe Thr
                85                  90                  95

Leu Thr Ile Ser Asp Leu Asp Cys Asp Asp Ala Ala Thr Tyr Tyr Cys
            100                 105                 110

Ala Gly Gly Phe Ser Gly His Ile Tyr Asp Phe Gly Gly Gly Thr Glu
        115                 120                 125

Val Val Val Lys Gly
    130

<210> SEQ ID NO 18
<211> LENGTH: 13
<212> TYPE: PRT
<213> ORGANISM: Artificial Sequence
<220> FEATURE:
<223> OTHER INFORMATION: CDR1

<400> SEQUENCE: 18

Gln Ser Ser Gln Ser Val Tyr Arg Gly Asp Trp Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: CDR2

<400> SEQUENCE: 19

Gly Ala Ser Thr Leu Ala Ser
1               5

<210> SEQ ID NO 20
<211> LENGTH: 10
<212> TYPE: PRT
<213> ORGANISM: Artificial Sequence
<220> FEATURE:
<223> OTHER INFORMATION: CDR3

<400> SEQUENCE: 20

Ala Gly Gly Phe Ser Gly His Ile Tyr Asp
1               5                   10
```

```
<210> SEQ ID NO 21
<211> LENGTH: 5
<212> TYPE: PRT
<213> ORGANISM: Artificial Sequence
<220> FEATURE:
<223> OTHER INFORMATION: CDR1

<400> SEQUENCE: 21

Asn Tyr Pro Met Thr
1               5

<210> SEQ ID NO 22
<211> LENGTH: 16
<212> TYPE: PRT
<213> ORGANISM: Artificial Sequence
<220> FEATURE:
<223> OTHER INFORMATION: CDR2

<400> SEQUENCE: 22

Val Ile Asn Asn Ser Gly Glu Thr Ala Tyr Ala Thr Trp Ala Lys Arg
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: CDR3

<400> SEQUENCE: 23

Gly Gly Pro Val Ser Ser Asp Met
1               5

<210> SEQ ID NO 24
<211> LENGTH: 18
<212> TYPE: PRT
<213> ORGANISM: Homo sapiens

<400> SEQUENCE: 24

Glu Gln Lys Ala His Leu Glu Asp Tyr Tyr Trp Met Thr Gly Tyr Pro
1               5                   10                  15

Gln Gln
```

THERAPEUTIC TREATMENT OF BREAST CANCER BASED ON C-MAF STATUS

CROSS-REFERENCE TO RELATED APPLICATIONS

This application is a 35 U.S.C. § 371 National Phase Application of International Application No. PCT/IB2017/053094, filed May 25, 2017, which claims the benefit of U.S. Provisional Application Nos. 62/344,836, filed Jun. 2, 2016, and 62/341,333, filed May 25, 2016, the content of each of which is incorporated herein by reference in its entirety.

REFERENCE TO SEQUENCE LISTING SUBMITTED ELECTRONICALLY VIA EFS-WEB

The content of the electronically submitted sequence listing (Name: 3190_0150002_ST25.txt; Size: 58,793 bytes; and Date of Creation: Nov. 13, 2018) is herein incorporated by reference in its entirety.

BACKGROUND OF THE INVENTION

Field of the Invention

The present invention relates to the design of a customized therapy for a subject with breast cancer, wherein the customized therapy is selected based on the c-MAF expression level, copy number, amplification, gain, or translocation and the menopausal status of the subject. In some embodiments, the customized therapy comprises an agent for avoiding or preventing bone remodelling. In some embodiments, the agent for avoiding or preventing bone remodelling is zoledronic acid.

Background Art

Breast cancer is the second most common type of cancer worldwide (10.4%; after lung cancer) and the fifth most common cause of death by cancer (after lung cancer, stomach cancer, liver cancer, and colon cancer). Among women, breast cancer is the most common cause of death by cancer. In 2005, breast cancer caused 502,000 deaths worldwide (7% of the deaths by cancer; almost 1% of all deaths). The number of cases worldwide has increased significantly from the 1970s, a phenomenon which is partly due to the modern lifestyle in the western world.

Breast cancer is classified into stages according to the TNM system. (See American Joint Committee on Cancer. AJCC Cancer Staging Manual. 6th ed. New York, N.Y.: Springer, 2002, which is incorporated herein by reference in its entirety.) The prognosis is closely related to the results of the stage classification, and the stage classification is also used to assign patients to treatments both in clinical trials and in the medical practice. The information for classifying into stages is as follow:

TX: The primary tumor cannot be assessed. T0: there is no evidence of tumor. Tis: in situ carcinoma, no invasion. T1: The tumor is 2 cm or less. T2: The tumor is more than 2 cm but less than 5 cm. T3: The tumor is more than 5 cm. T4: Tumor of any size growing in the wall of the breast or skin, or inflammatory breast cancer.

NX: The nearby lymph nodes cannot be assessed. N0: The cancer has not spread to the regional lymph nodes. N1: The cancer has spread to 1 to 3 axillary lymph nodes or to one internal mammary lymph node. N2: The cancer has spread to 4 to 9 axillary lymph nodes or to multiple internal mammary lymph nodes. N3: One of the followings applies:

The cancer has spread to 10 or more axillary lymph nodes, or the cancer has spread to the infraclavicular lymph nodes, or the cancer has spread to the supraclavicular lymph nodes or the cancer affects the axillary lymph nodes and has spread to the internal mammary lymph nodes, or the cancer affects 4 or more axillary lymph nodes and minimum amounts of cancer are in the internal mammary nodes or in sentinel lymph node biopsy.

MX: The presence of distant spread (metastasis) cannot be assessed. M0: There is no distant spread. M1: spreading to distant organs which do not include the supraclavicular lymph node has been produced.

The fact that most of the patients with solid tumor cancer die after metastasis means that it is crucial to understand the molecular and cellular mechanisms allowing a tumor to metastasize. Recent publications have demonstrated how the metastasis is caused by means of complex yet little known mechanisms and also how the different metastatic cell types have a tropism towards specific organs These tissue specific metastatic cells have a series of acquired functions allowing them to colonize specific organs.

All cells have receptors on their surface, in their cytoplasm and in the cell nucleus. Certain chemical messengers such as hormones bind to said receptors and this causes changes in the cell. There are three significant receptors which may affect the breast cancer cells: estrogen receptor (ER), progesterone receptor (PR) and HER2/neu. For the purpose of naming the cells having any of these receptors, a positive sign is placed thereto when the receptor is present and a negative sign if it is absent: ER positive (ER+), ER negative (ER−), PR positive (PR+), PR negative (PR−), HER2 positive (HER2+) and HER2 negative (HER2−). The receptor state has become a critical assessment for all breast cancers since it determines the suitability of using specific treatments, for example, tamoxifen or trastuzumab.

Unsupervised gene expression array profiling has provided biological evidence for the heterogeneity of breast cancer through the identification of intrinsic subtypes such as luminal A, luminal B, HER2+/ER− and the basal-like subtype.

Triple-negative cancers are defined as tumors that do not express the genes for estrogen receptor (ER), progesterone receptor (PR) nor HER2. This subgroup accounts for 15% of all types of breast cancer and for a higher percentage of breast cancer arising in African and African-American women who are premenopausal. Triple negative breast cancers have a relapse pattern that is very different from Estrogen Receptor positive breast cancers: the risk of relapse is much higher for the first 3-5 years but drops sharply and substantially below that of Estrogen Receptor positive breast cancers after that.

The basal-like subtype is characterized by low expression of both the ER and HER2 clusters of genes, so is typically ER-negative, PR-negative, and HER2-negative on clinical testing; for this reason, it is often referred to as "triple-negative" breast cancer (Breast Cancer Research 2007, 9(Suppl 1):S13). Basal-like cancers express genes usually found in "basal"/myoepithelial cells of the normal breast including high molecular weight cytokeratins (5/6, 14 and 17), P-cadherin, caveolins 1 and 2, nestin, αB crystalline and epidermal growth factor receptor (Reis-Fiho J. et al.).

Given that there is no internationally accepted definition for basal-like breast cancers, it is not surprising that there has been a great deal of confusion as to whether triple negative and basal-like breast cancers are synonymous.

Although several groups have used these terms interchangeably, it should be noted that not all basal-like cancers lack ER, PR and HER2 and not all triple negative cancers display a basal-like phenotype. The vast majority of triple negative cancers are of basal-like phenotype. Likewise, the vast majority of tumors expressing 'basal' markers are triple negative. It should be noted, however, that there is a significant number of triple negative cancers that do not express basal markers and a small, but still significant, subgroup of basal-like cancers that express either hormone receptors or HER2. Bertucci et al. (Int J Cancer. 2008 Jul. 1; 123(1): 236-40) have addressed this issue directly and confirmed that not all triple negative tumors when analyzed by gene expression profiling were classified as basal-like cancers (i.e. only 71% were of basal-like phenotype) and not all basal-like breast carcinomas classified by expression arrays displayed a triple negative phenotype (i.e. 77%).

The keystone for treating breast cancer is surgery when the tumor is localized with possible adjuvant hormone therapy (with tamoxifen or an aromatase inhibitor), chemotherapy, and/or radiotherapy. Currently, the suggestions for treatment after the surgery (adjuvant therapy) follow a pattern. This pattern is subject to change because every two years a world conference takes place in St. Gallen, Switzerland to discuss the actual results of the worldwide multicenter studies. Likewise, said pattern is also reviewed according to the consensus criterion of the National Institute of Health (NIH). Based on in these criteria, more than 85-90% of the patients not having metastasis in lymph nodes would be candidates to receive adjuvant systemic therapy.

Currently, PCR assays such as Oncotype DX or microarray assays such as MammaPrint can predict the risk of breast cancer relapse based on the expression of specific genes. In February 2007, the MammaPrint assay became the first breast cancer indicator in achieving official authorization from the Food and Drug Administration.

Patent application EP1961825-A1 describes a method for predicting the occurrence of breast cancer metastasis to bone, lung, liver or brain, which comprises determining in a tumor tissue sample the expression level of one or more markers with respect to their corresponding expression level in a control sample, among which include c-MAF. However, this document requires determining several genes simultaneously to enable determining the survival of breast cancer patients and the correlation between the capacities of the gene signature for predicting the survivability free from bone metastasis was not statistically significant.

Patent publication U.S. Publ. No. 2011/0150979 describes a method for predicting a prognosis of a basal like breast cancer comprising detecting the level of FOXC1.

Patent publication U.S. Publ. No. 2010/0210738 relates to a method for prognosing cancer in a subject with triple negative breast cancer comprising detecting in a sample the expression levels of a series of genes which are randomly up-regulated or down-regulated.

Patent publication U.S. Publ. No. 2011/0130296 relates to the identification of marker genes useful in the diagnosis and prognosis of triple negative breast cancer.

There is a need for the identification of subsets of patients with breast cancer that will benefit from specific treatments, and, conversely, subsets of patients with breast cancer that will not benefit, or will potentially be harmed, by specific treatments.

SUMMARY OF THE INVENTION

In one embodiment, the present invention relates to an in vitro method for designing a customized therapy for a subject having breast cancer which comprises: i) quantifying the c-MAF gene expression level, copy number, amplification, or gain in a sample of said subject and ii) comparing the expression level, copy number, amplification, or gain obtained in i) with a reference value, wherein if the expression level, copy number, amplification, or gain is not increased with respect to said reference value, then said subject is susceptible to receive a therapy aiming to prevent and/or treat bone remodeling, improve disease free survival or overall survival.

In some embodiments, the subject is non-postmenopausal. In other embodiments, the subject is postmenopausal.

In one embodiment, the present invention relates to an in vitro method for designing a customized therapy for a non-postmenopausal subject having breast cancer which comprises: i) quantifying the c-MAF gene expression level, copy number, amplification, or gain in a sample of said subject and ii) comparing the expression level, copy number, amplification, or gain obtained in i) with a reference value, wherein if the expression level, copy number, amplification, or gain is increased with respect to said reference value, then said subject is not susceptible to receive a therapy aiming to prevent and/or treat bone remodeling, improve disease free survival or overall survival.

In one embodiment, the present invention relates to an in vitro method for designing a customized therapy for a postmenopausal subject having breast cancer which comprises: i) quantifying the c-MAF gene expression level, copy number, amplification, or gain in a sample of said subject and ii) comparing the expression level, copy number, amplification, or gain obtained in i) with a reference value, wherein if the expression level, copy number, amplification, or gain is increased with respect to said reference value, then said subject is susceptible to receive a therapy aiming to prevent and/or treat bone remodeling, improve disease free survival or overall survival.

In some embodiments, the subject is administered a therapy aiming to prevent and/or treat bone remodeling, improve disease free survival or overall survival. In other embodiments, the subject is not administered a therapy aiming to prevent and/or treat bone remodeling, improve disease free survival or overall survival.

In certain embodiments, the therapy aiming to prevent and/or treat bone remodelling or improve disease free survival or overall survival is an agent intended to prevent or inhibit bone degradation, improve disease free survival or overall survival is selected from the group consisting of: a bisphosphonate, a RANKL inhibitor, PTH, a PTHLH inhibitor (including neutralizing antibodies and peptides), a PRG analog, strontium ranelate, a DKK-1 inhibitor, a dual MET and VEGFR2 inhibitor, an estrogen receptor modulator, calcitonin, Radium-223, a CCR5 antagonist, a Src kinase inhibitor, a COX-2 inhibitor, an mTor inhibitor, and a cathepsin K inhibitor. In some embodiments, the RANKL inhibitor is selected from the group consisting of: a RANKL specific antibody, a RANKL-specific nanobody, and osteoprotegerin. In particular embodiments, the RANKL specific antibody is denosumab. In some embodiments, the bisphosphonate is zoledronic acid. In other embodiments, the RANKL specific nanobody is ALX-0141. In certain embodiments, the dual MET and VEGFR2 inhibitor is Cabozantinib.

In some embodiments, the quantification of the c-MAF gene expression level comprises quantifying the messenger RNA (mRNA) of said gene, or a fragment of said mRNA, the complementary DNA (cDNA) of said gene, or a fragment of said cDNA or quantifying the levels of protein encoded by said gene. In particular embodiments, the expression level, copy number, amplification or gain is quantified by means of a quantitative polymerase chain reaction (PCR) or a DNA or RNA array or nucleotide hybridization technique. In embodiments, the level of protein is quantified by means of western blot, ELISA, immunohistochemistry or a protein array. In certain embodiments, the level of protein is quantified using an antibody comprising a heavy chain CDR1 of SEQ ID NO: 21, and/or a heavy chain CDR2 of SEQ ID NO: 22, and/or a heavy chain CDR3 of SEQ ID NO: 23; and/or comprising a light chain CDR1 of SEQ ID NO: 18, and/or a light chain CDR2 of SEQ ID NO: 19 and/or a light chain CDR3 of SEQ ID NO: 20 In some embodiments, the amplification or gain of the c-MAF gene is determined by means of using a c-MAF gene-specific probe. In particular embodiments, the c-MAF gene-specific probe is Vysis LSI/IGH MAF Dual Color Dual Fusion Probe. In other embodiments, the amplification or gain is determined by means of in situ hybridization or PCR.

In certain embodiments, the reference value is that of a tumor tissue sample of breast cancer from a subject who has not suffered metastasis.

In one embodiment, the present invention relates to a method for the treatment of bone metastasis in a subject having breast cancer and having not increased c-MAF expression levels in a metastatic tumor sample with respect to a control sample comprising administering an agent capable of preventing or inhibiting bone remodelling, or improving disease free survival or overall survival wherein the agent capable of avoiding or preventing bone remodeling or improving disease free survival or overall survival is selected from the group consisting of: a bisphosphonate, a RANKL inhibitor, PTH, PTHLH inhibitor (including neutralizing antibodies and peptides), a PRG analog, strontium ranelate, a DKK-1 inhibitor, a dual MET and VEGFR2 inhibitor, an estrogen receptor modulator, an EGFR inhibitor, calcitonin, Radium-223, a CCR5 antagonist, a Src kinase inhibitor, a COX-2 inhibitor, an mTor inhibitor, and a cathepsin K inhibitor.

In certain embodiments, the subject is non-postmenopausal. In other embodiments, the subject is postmenopausal.

In one embodiment, the present invention relates to a method for the treatment of bone metastasis in a postmenopausal subject having breast cancer and having increased c-MAF expression levels in a metastatic tumor sample with respect to a control sample comprising administering an agent capable of preventing or inhibiting bone remodelling, or improving disease free survival or overall survival wherein the agent capable of avoiding or preventing bone remodelling is selected from the group consisting of: a bisphosphonate, a RANKL inhibitor, PTH, PTHLH inhibitor (including neutralizing antibodies and peptides), a PRG analog, strontium ranelate, a DKK-1 inhibitor, a dual MET and VEGFR2 inhibitor, an estrogen receptor modulator, an EGFR inhibitor, calcitonin, Radium-223, a CCR5 antagonist, a Src kinase inhibitor, a COX-2 inhibitor, an mTor inhibitor, and a cathepsin K inhibitor.

In particular embodiments, the RANKL inhibitor is selected from the group of: a RANKL specific antibody, a RANKL specific nanobody, and osteoprotegerin. In further embodiments, the RANKL specific antibody is denosumab. In other embodiments, the bisphosphonate is zoledronic acid. In yet other embodiments, the RANKL specific nanobody is ALX-9141. In certain embodiments, the dual MET and VEGFR2 inhibitor is Cabozantinib.

In one embodiment, the present invention relates to a method of classifying a subject suffering from breast cancer into a cohort, comprising: a) determining the expression level, copy number, amplification, or gain of c-MAF in a breast tumor sample of said subject; b) comparing the expression level, copy number, amplification, or gain of c-MAF in said sample to a predetermined reference level of c-MAF expression; and c) classifying said subject into a cohort based on said expression level, copy number, amplification, or gain of c-MAF in the sample and the status of the subject as post-menopausal or non-post-menopausal.

In certain embodiments, the subjects are administered different treatments based on their c-MAF expression levels and/or their post-menopausal or non-post-menopausal status.

In some embodiments, the quantification of the c-MAF expression level comprises quantifying the messenger RNA (mRNA) of said gene, or a fragment of said mRNA, the complementary DNA (cDNA) of said gene, or a fragment of said cDNA or quantifying the levels of protein encoded by said gene. In particular embodiments, the level of protein is quantified using an antibody comprising a heavy chain CDR1 of SEQ ID NO: 21, and/or a heavy chain CDR2 of SEQ ID NO: 22, and/or a heavy chain CDR3 of SEQ ID NO: 23; and/or comprising a light chain CDR1 of SEQ ID NO: 18, and/or a light chain CDR2 of SEQ ID NO: 19 and/or a light chain CDR3 of SEQ ID NO: 20 In certain embodiments, the amplification is determined by means of in situ hybridization or PCR. In further embodiments, the in situ hybridization is fluorescence in situ hybridization (FISH), chromogenic in situ hybridization (CISH) or silver in situ hybridization (SISH). In still further embodiments, the in situ hybridization is fluorescence in situ hybridization (FISH).

In some embodiments, the copy number of c-MAF as measured using FISH is ≥2.1, 2.2, 2.3, 2.4, 2.5, 2.6, 2.7, 2.8, 2.9 or 3.0. In particular embodiments, the copy number of c-MAF as measured using FISH is ≥2.2. In further embodiments, the copy number of c-MAF as measured using FISH is ≥2.3. In still further embodiments, the copy number of c-MAF as measured using FISH is ≥2.4. In certain embodiments, the copy number of c-MAF as measured using FISH is ≥2.5. In other embodiments, the copy number of c-MAF as measured using FISH is <2.1, 2.2, 2.3, 2.4, 2.5, 2.6, 2.7, 2.8, 2.9 or 3.0.

In one embodiment, the present invention relates to an in vitro method for predicting the IDFS of a patient with breast cancer which comprises i) quantifying the expression level, copy number, amplification, or gain of the c-MAF gene in a sample of said subject and ii) comparing the expression level, copy number, amplification, or gain 1 obtained in step i) with a reference value, wherein increased expression level, copy number, amplification, or gain of said gene with respect to said reference value is indicative of a poor IDFS.

In one embodiment, the present invention relates to an in vitro method for predicting IDFS of a patient with breast cancer which comprises determining the c-MAF gene expression level, copy number, amplification, or gain in a sample of said subject relative to a reference wherein an increase of the c-MAF gene expression level, copy number, amplification, or gain with respect to said reference is indicative of a poor IDFS.

In one embodiment, the present invention relates to an in vitro method for predicting IDFS excluding bone recurrence of a patient with breast cancer which comprises determining the c-MAF gene expression level, copy number, amplification, or gain in a sample of said subject relative to a reference wherein an increase of the c-MAF gene expression level, copy number, amplification, or gain with respect to said reference is indicative of poor IDFS excluding bone recurrence.

In some embodiments, the agent capable of preventing or inhibiting bone remodelling is an agent capable of preventing or inhibiting bone degradation In some embodiments, the quantification of the c-MAF expression level comprises quantifying the messenger RNA (mRNA) of said gene, or a fragment of said mRNA, the complementary DNA (cDNA) of said gene, or a fragment of said cDNA or quantifying the levels of protein encoded by said gene. In certain embodiments, the level of protein is quantified using an antibody comprising a heavy chain CDR1 of SEQ ID NO: 21, and/or a heavy chain CDR2 of SEQ ID NO: 22, and/or a heavy chain CDR3 of SEQ ID NO: 23; and/or comprising a light chain CDR1 of SEQ ID NO: 18, and/or a light chain CDR2 of SEQ ID NO: 19 and/or a light chain CDR3 of SEQ ID NO: 20. In other embodiments, the amplification is determined by means of in situ hybridization or PCR. In further embodiments, the in situ hybridization is fluorescence in situ hybridization (FISH), chromogenic in situ hybridization (CISH) or silver in situ hybridization (SISH). In still further embodiments, the in situ hybridization is fluorescence in situ hybridization (FISH).

In some embodiments, the copy number of c-MAF as measured using FISH is ≥2.1, 2.2, 2.3, 2.4, 2.5, 2.6, 2.7, 2.8, 2.9 or 3.0. In certain embodiments, the copy number of c-MAF as measured using FISH is ≥2.2. In other embodiments, the copy number of c-MAF as measured using FISH is ≥2.3. In further embodiments, the copy number of c-MAF as measured using FISH is ≥2.4. In still further embodiments, the copy number of c-MAF as measured using FISH is ≥2.5. In some embodiments, the copy number is determined as the average copy number per cell.

In some embodiments, the breast cancer is ER+ breast cancer. In particular embodiments, the breast cancer is ER– breast cancer. In other embodiments, the breast cancer is triple negative breast cancer. In different embodiments, the breast cancer is of the basal-like subtype. In some embodiments, the breast cancer is HER2+ breast cancer.

In some embodiments, the expression level, copy number, amplification, or gain of the c-MAF gene is determined by means of determining the expression level, copy number, amplification, or gain of the locus 16q23 or 16q22-q24.

In some embodiments, the treatment is an mTOR inhibitor or a CDK4/6 inhibitor. In other embodiments, the treatment is hormonal therapy extended beyond the standard of care.

In some embodiments, the invention relates to a method for the treatment of a subject having breast cancer and having increased c-MAF expression levels, copy number, amplification, or gain in a metastatic tumor sample with respect to a control sample comprising administering an mTOR inhibitor or a CDK4/6 inhibitor. In some embodiments, the invention relates to a method for the treatment of a subject having breast cancer and having increased c-MAF expression levels, copy number, amplification, or gain in a metastatic tumor sample with respect to a control sample comprising administering hormonal therapy extended beyond the standard of care. In some embodiments, the invention relates to a method for the treatment of a subject having breast cancer and having not increased c-MAF expression levels, copy number, amplification, or gain in a metastatic tumor sample with respect to a control sample comprising not administering an mTOR inhibitor or a CDK4/6 inhibitor. In some embodiments, the invention relates to a method for the treatment of a subject having breast cancer and having not increased c-MAF expression levels, copy number, amplification, or gain in a metastatic tumor sample with respect to a control sample comprising not administering hormonal therapy extended beyond the standard of care.

In one embodiment, the present invention relates to a method for predicting the disease free survival status of a patient comprising measuring the c-MAF gene expression level, copy number, amplification, or gain with respect to a reference sample level, and using the c-MAF gene expression level, copy number, amplification, or gain to predict the overall survival of the patient. In some embodiments, an increase in the c-MAF gene expression level, copy number, amplification, or gain with respect to a reference sample level is predictive of a shorter disease free survival than a patient without an increase in the c-MAF gene expression level, copy number, amplification, or gain with respect to a reference sample level.

In one embodiment, the present invention relates to a method for predicting the overall survival status of a patient comprising measuring the c-MAF gene expression level, copy number, amplification, or gain with respect to a reference sample level, and using the c-MAF gene expression level, copy number, amplification, or gain to predict the overall survival of the patient. In another embodiment, an increase in the c-MAF gene expression level, copy number, amplification, or gain with respect to a reference sample level is predictive of a shorter overall survival than a patient without an increase in the c-MAF gene expression level, copy number, amplification, or gain with respect to a reference sample level.

In embodiments, the menopausal status of the patient is also used to predict the survival status of the patient. In some embodiments, the subject is non-postmenopausal. In certain embodiments, the subject is premenopausal. In particular embodiments, the subject is postmenopausal.

BRIEF DESCRIPTION OF THE DRAWINGS

FIG. 1. Overview of the assay parameters.

Cumulative incidence of bone metastasis (A) as a first event and (B) at any time during follow-up. Analyses were by intention to treat. HR-hazard ratio.

Figure 14:
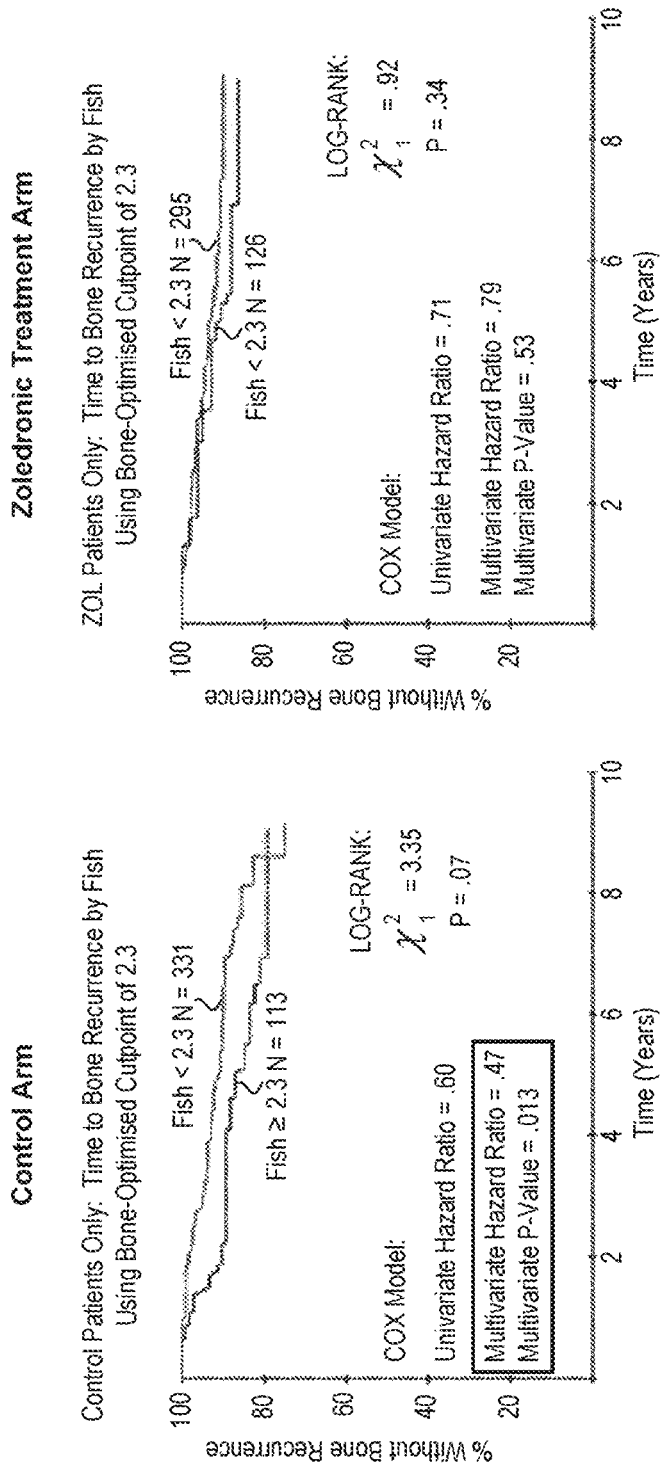

FIG. 14. Evaluation of the time to bone metastasis as a first event in AZURE control patients and zoledronic acid treated patients. A bone-optimized cutoff of 2.3 was used.

FIGS. 15A and B. Disease (DFS) and invasive disease (IDFS) free survival between the control arm and the zoledronic acid treated patients. Kaplan-Meier curves of (A) disease-free-survival and (B) invasive disease-free survival. Analyses were by intention to treat. HR=hazard ratio.

Figure 16:
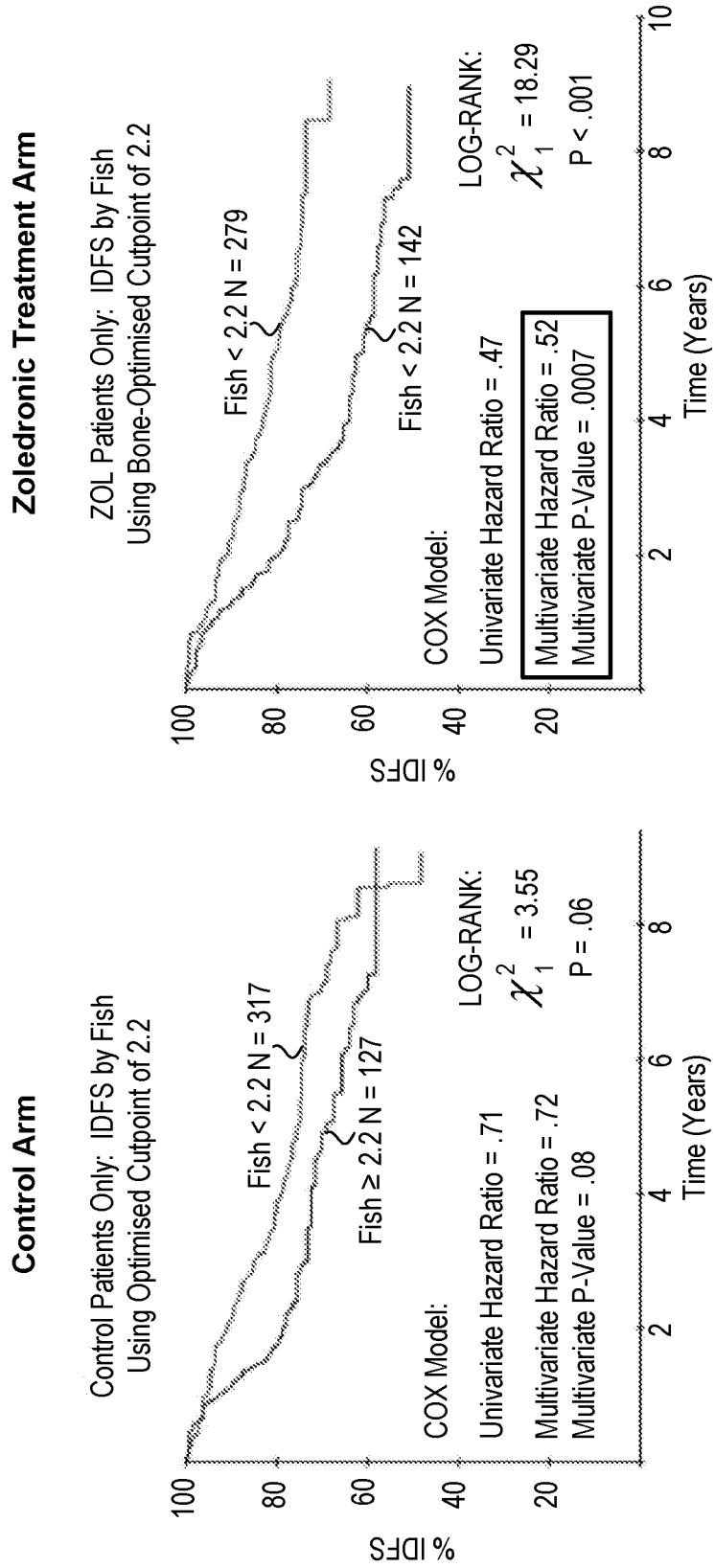

FIG. 16. Time to distant recurrence between the control arm and the zoledronic acid treated patients.

Figure 17:
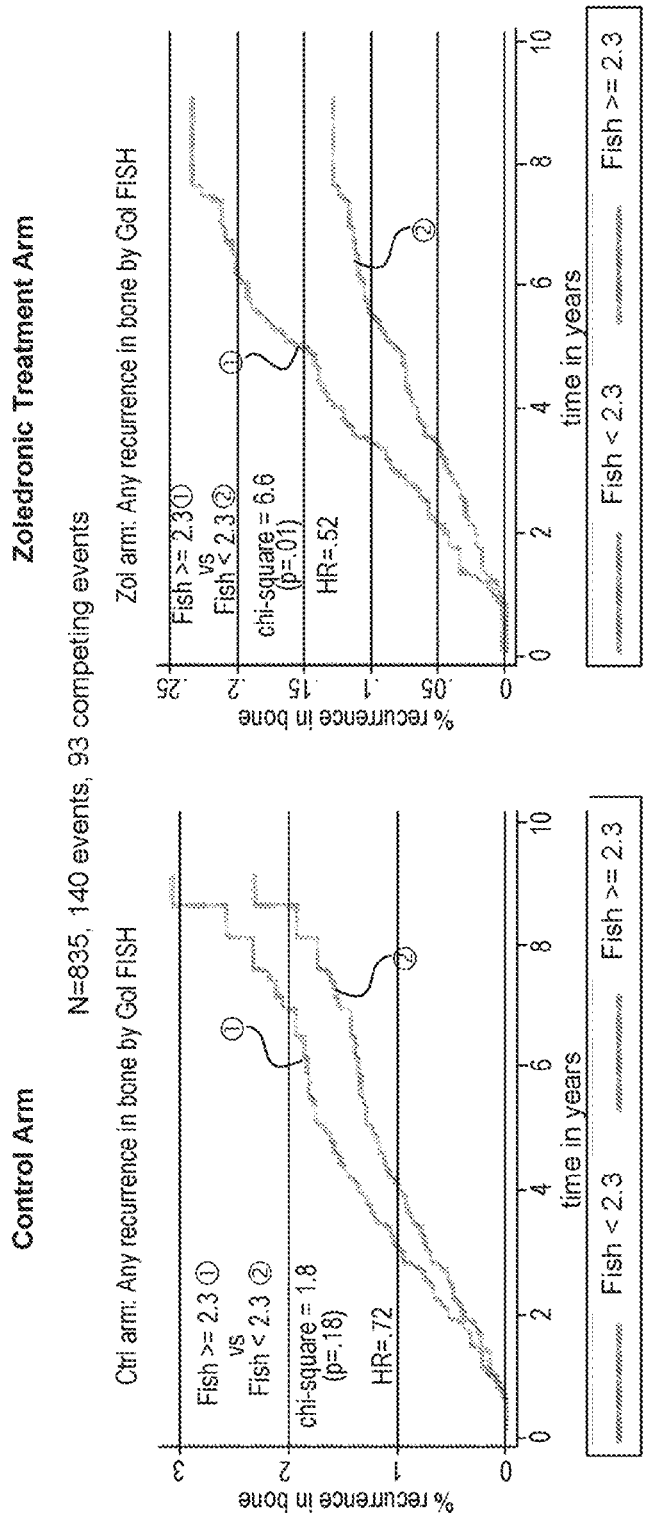

FIG. 17. Time to a bone metastatic event (anytime) according to treatment. Death as a competing event is used in time to bone metastasis (anytime).

Figure 18:
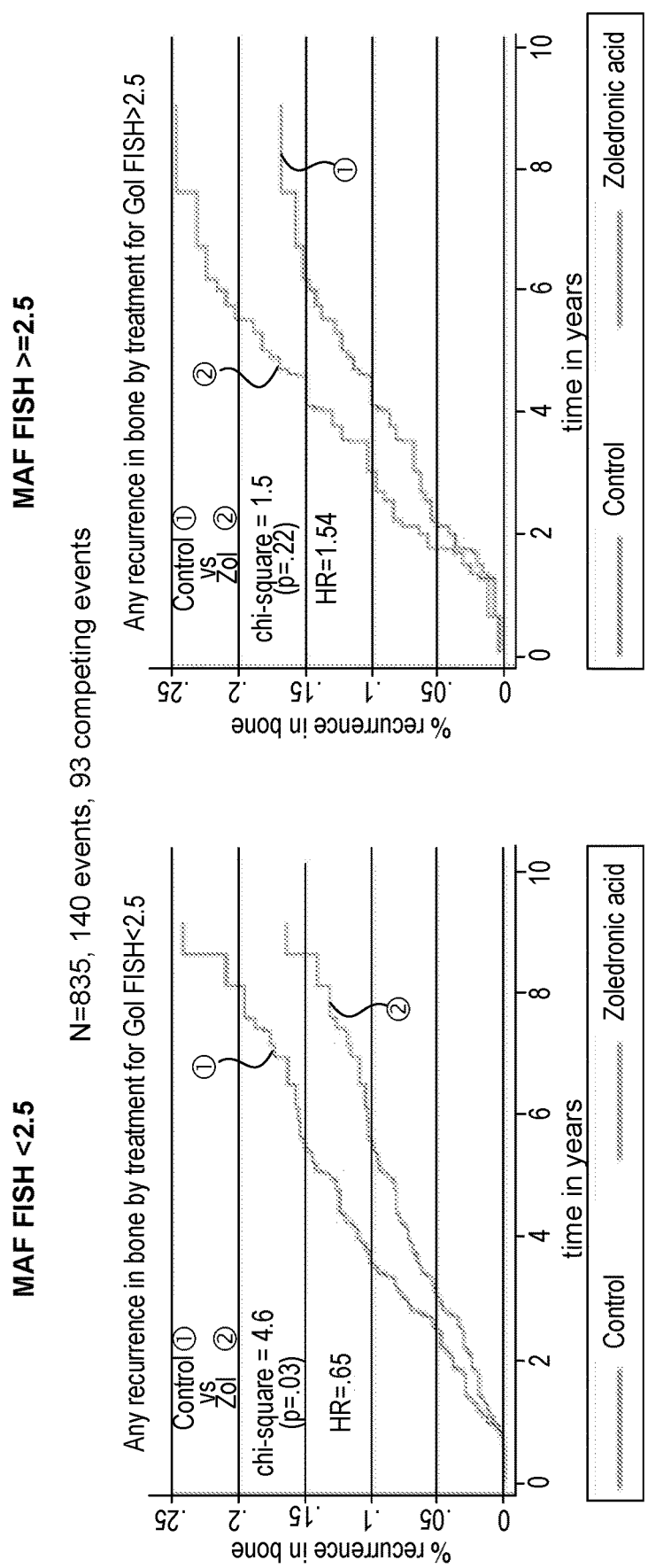

FIG. 18. Time to a bone metastatic event (anytime) according to MAF copy number (according to pre-specified MAF cut off of 2.5).

FIGS. 19A and B. IDFS by menopausal status of the AZURE trial. Kaplan-Meir curve of invasive disease-free survival by menopausal status. (A) premenopause, peri-menopause, and unknown menopausal status and (B) more than 5 years since menopause. Test of heterogeneity by menopausal status $\chi^2_1$ 4.71; p=0.03.

Figure 20:
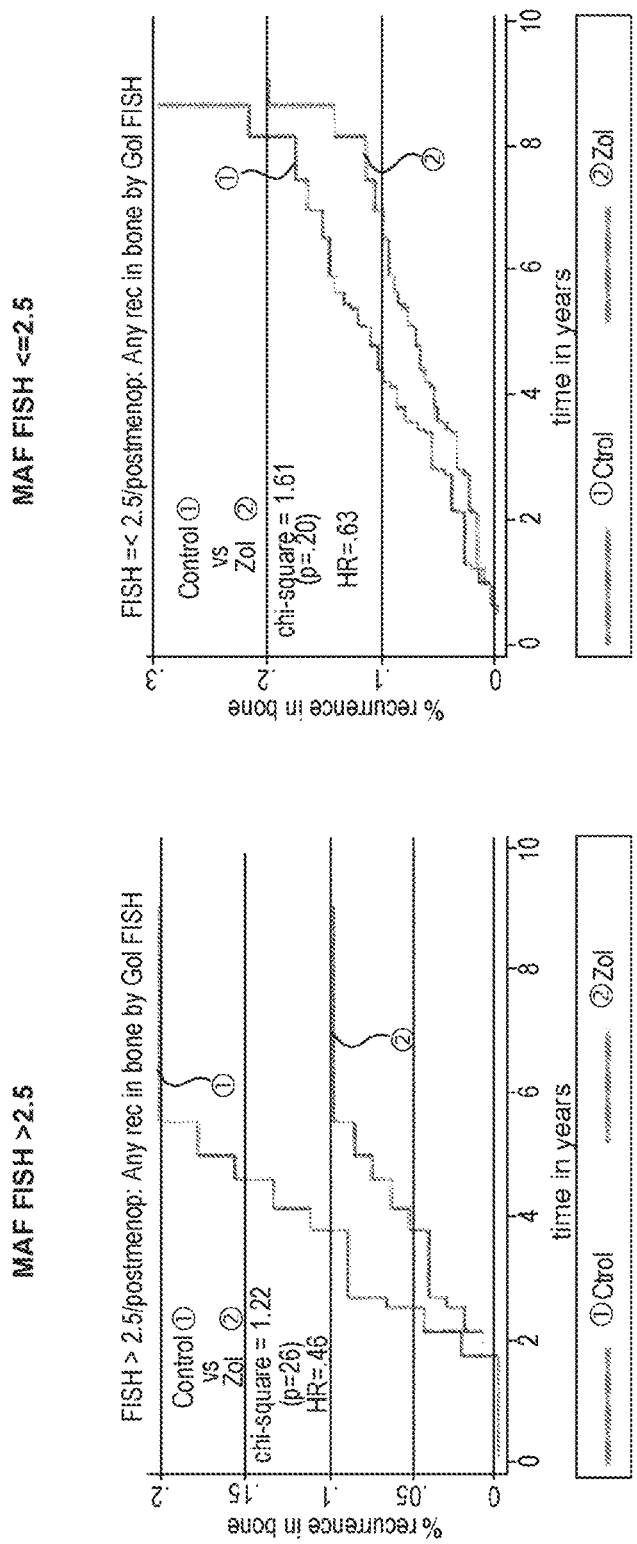

FIG. 20. Time to a bone metastatic event (anytime) according to MAF copy number (data according to a pre-specified cut off of 2.5) in post menopausal patients.

Figure 21:
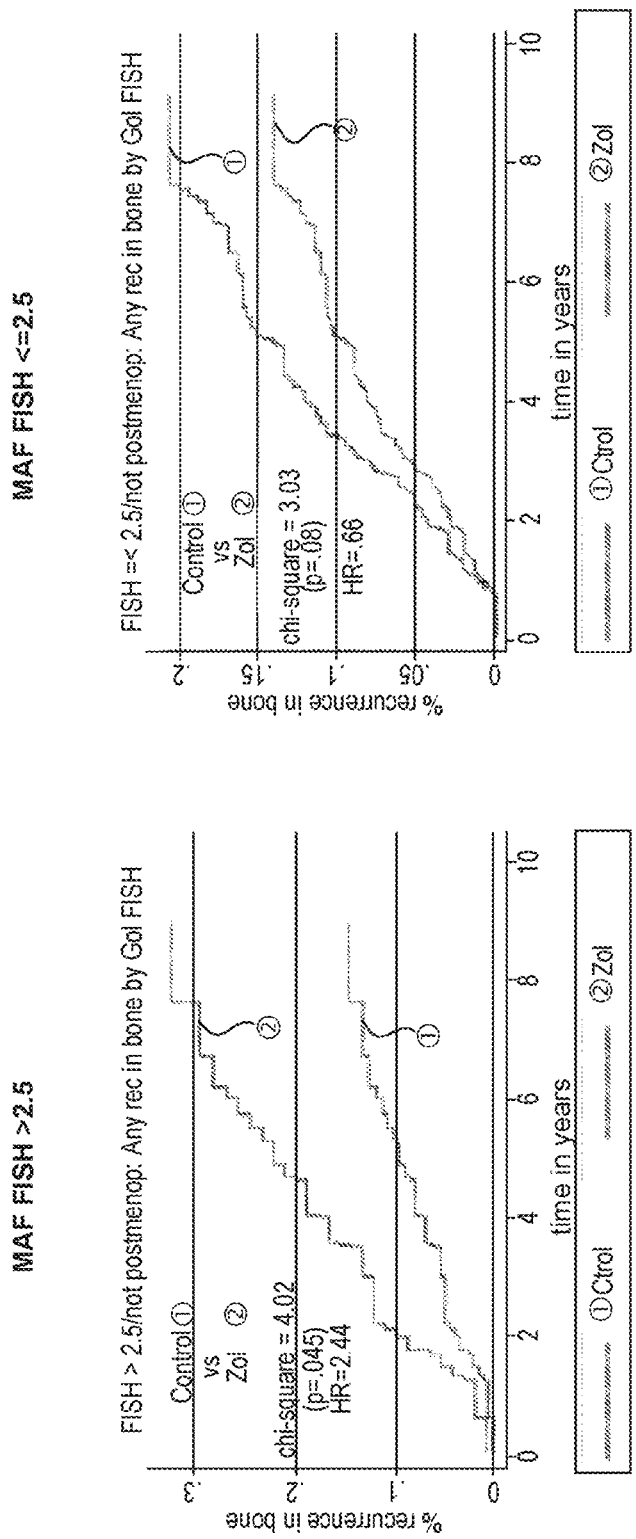

FIG. 21. Time to a bone metastatic event (anytime) according to MAF copy number (data according to a pre-specified cut off of 2.5) in non-post menopausal patients.

Figure 22:
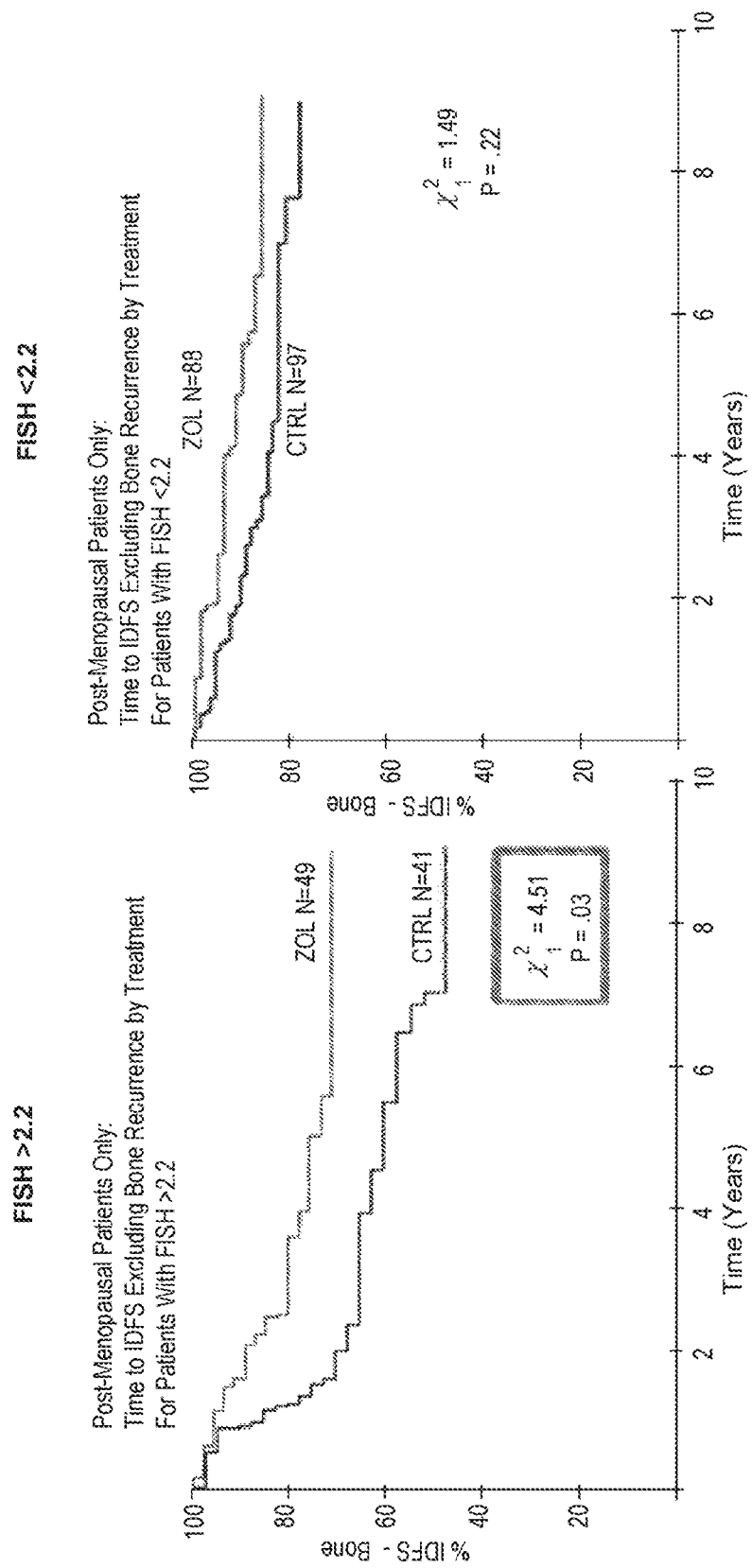

FIG. 22. IDFS of the zoledronic acid treatment arm and the control arm, excluding bone metastasis of post-menopausal women.

Figure 23:
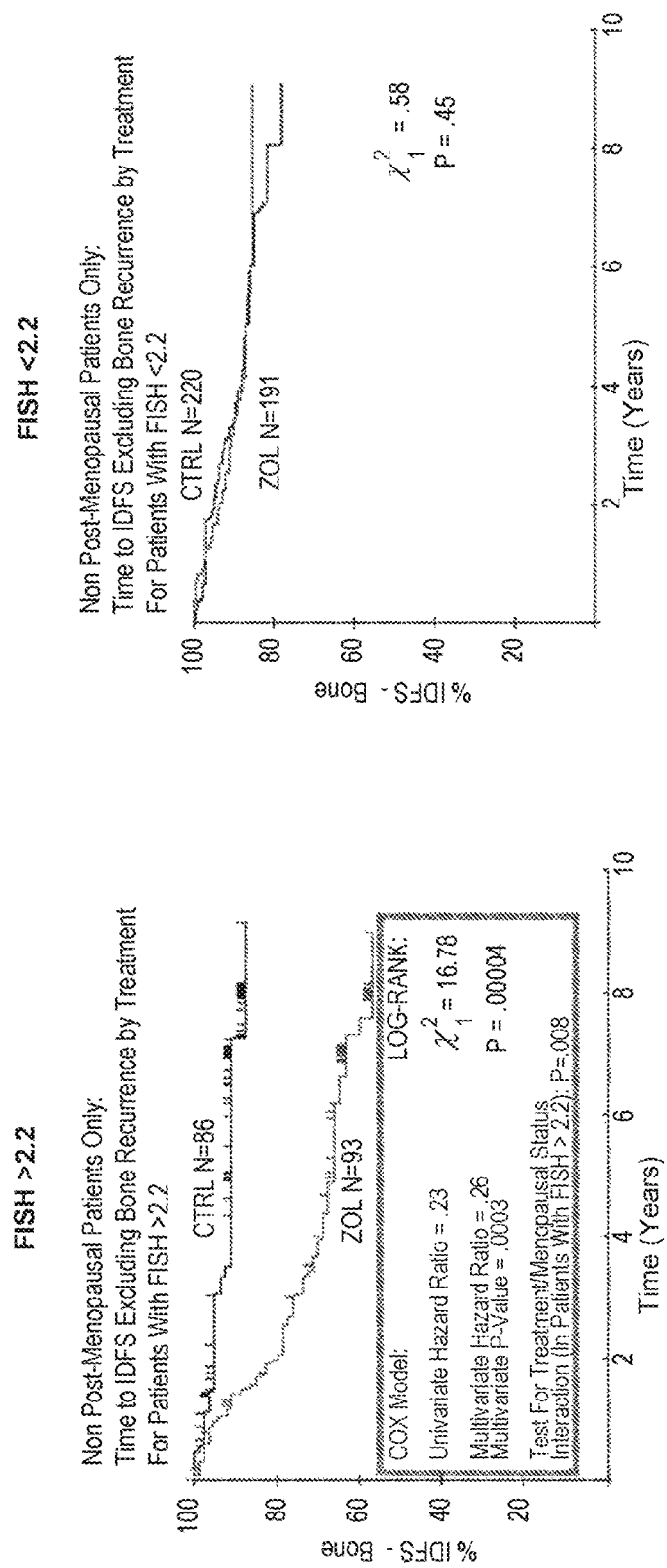

FIG. 23. IDFS of the zoledronic acid treatment arm and the control arm, excluding bone metastasis of non-post-menopausal women.

Figure 24:
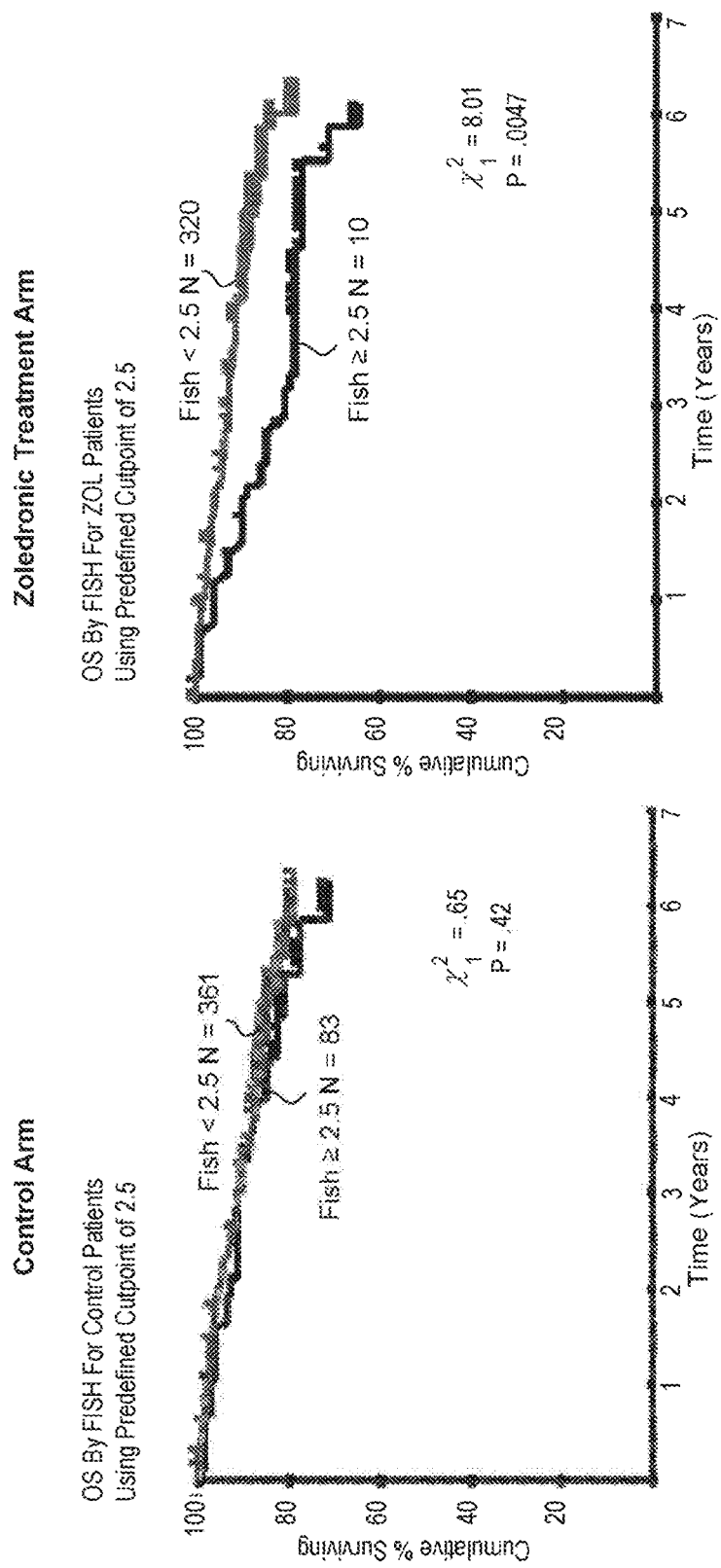

FIG. 24. Overall survival (OS) by treatment arm. Treatment of MAF FISH positive patients with zoledronic acid significantly impacted the OS.

Figure 25:
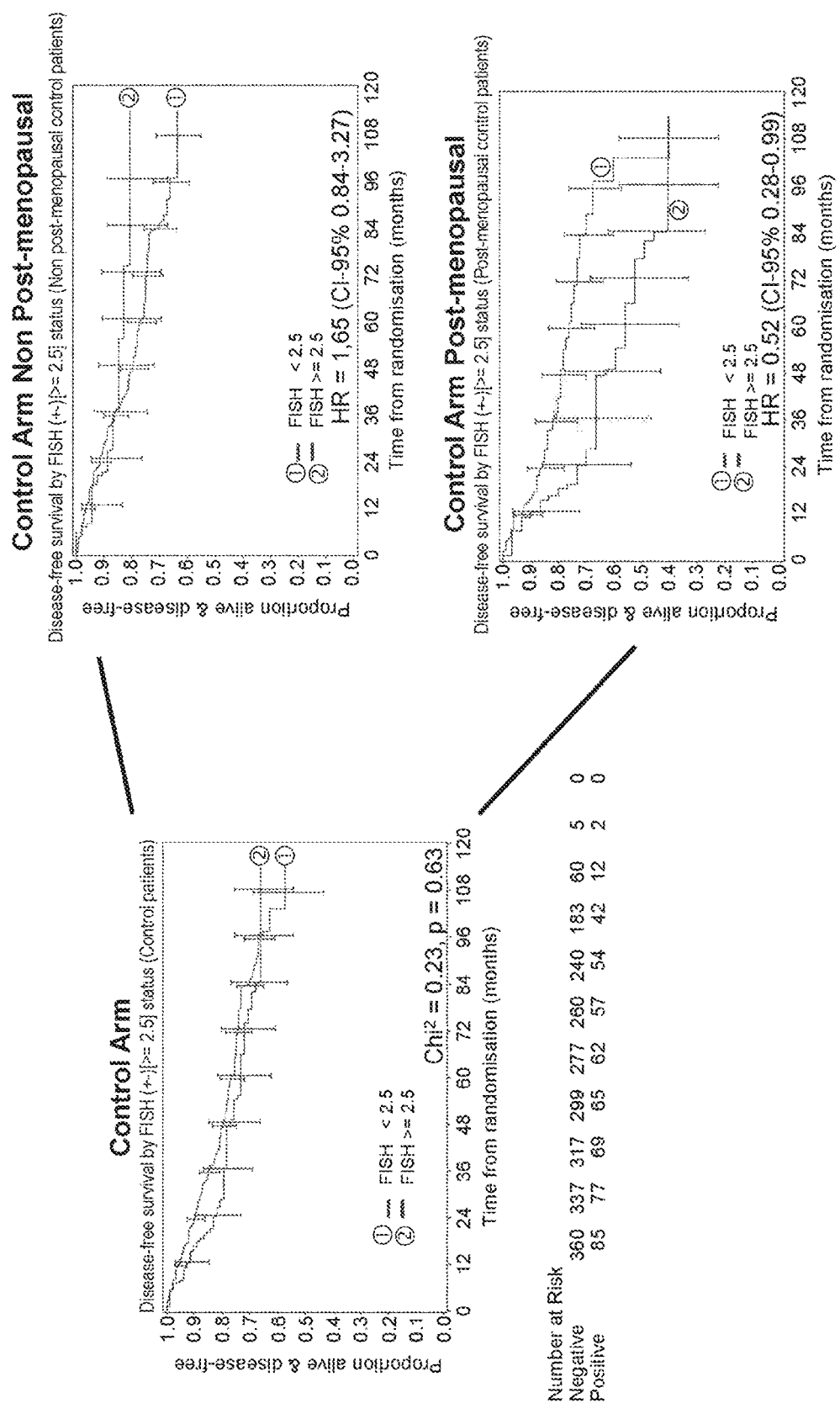

FIG. 25. Prognostic value of MAF FISH for disease free survival (DFS) in the Azure control arm.

Figure 26:
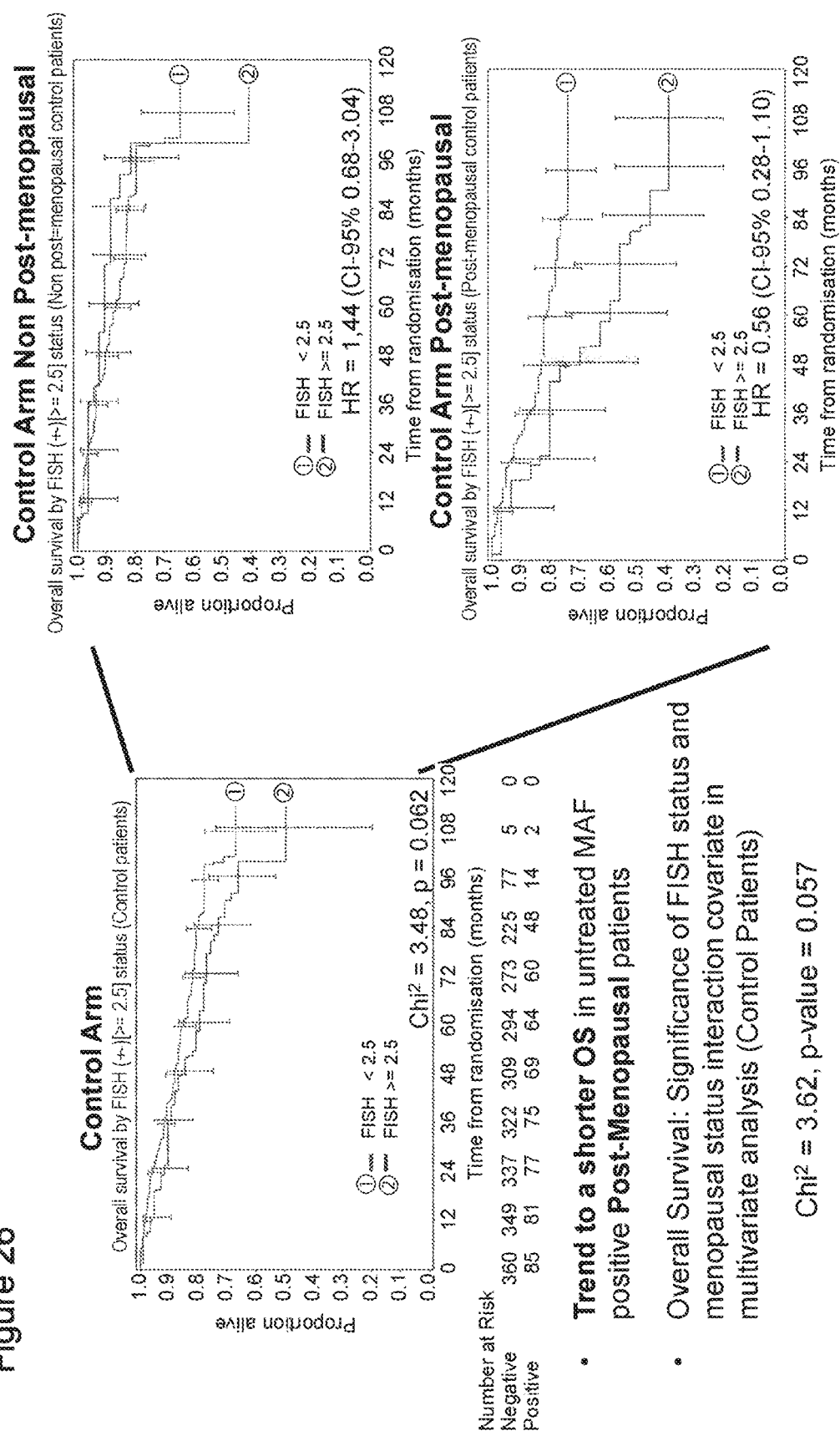

FIG. 26. Prognostic value of MAF FISH for overall survival (OS) in the Azure control arm.

Figure 27:
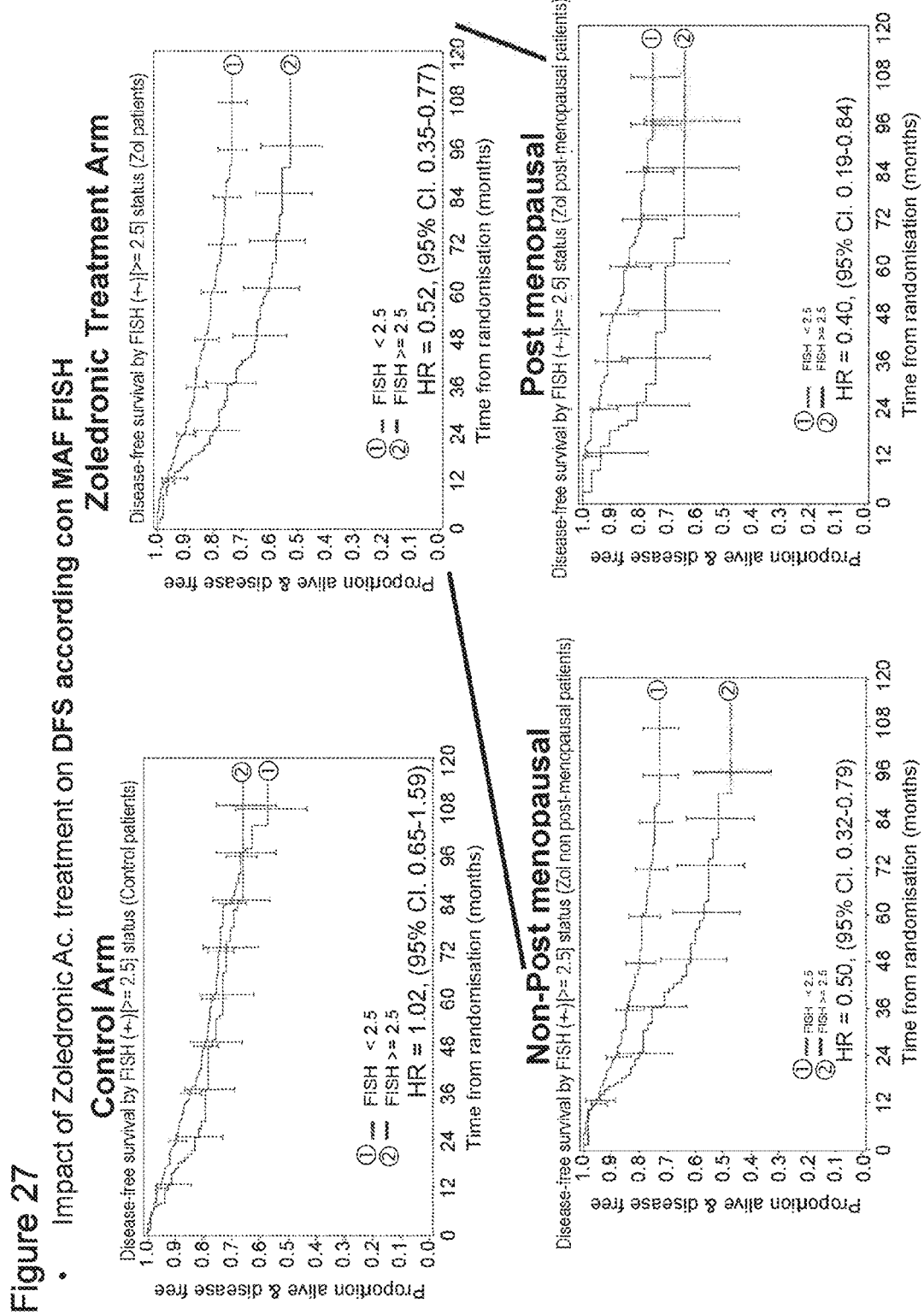

FIG. 27. Predictive value of MAF FISH for the effect of zoledronic acid treatment on the disease free survival (DFS) outcome.

Figure 28:
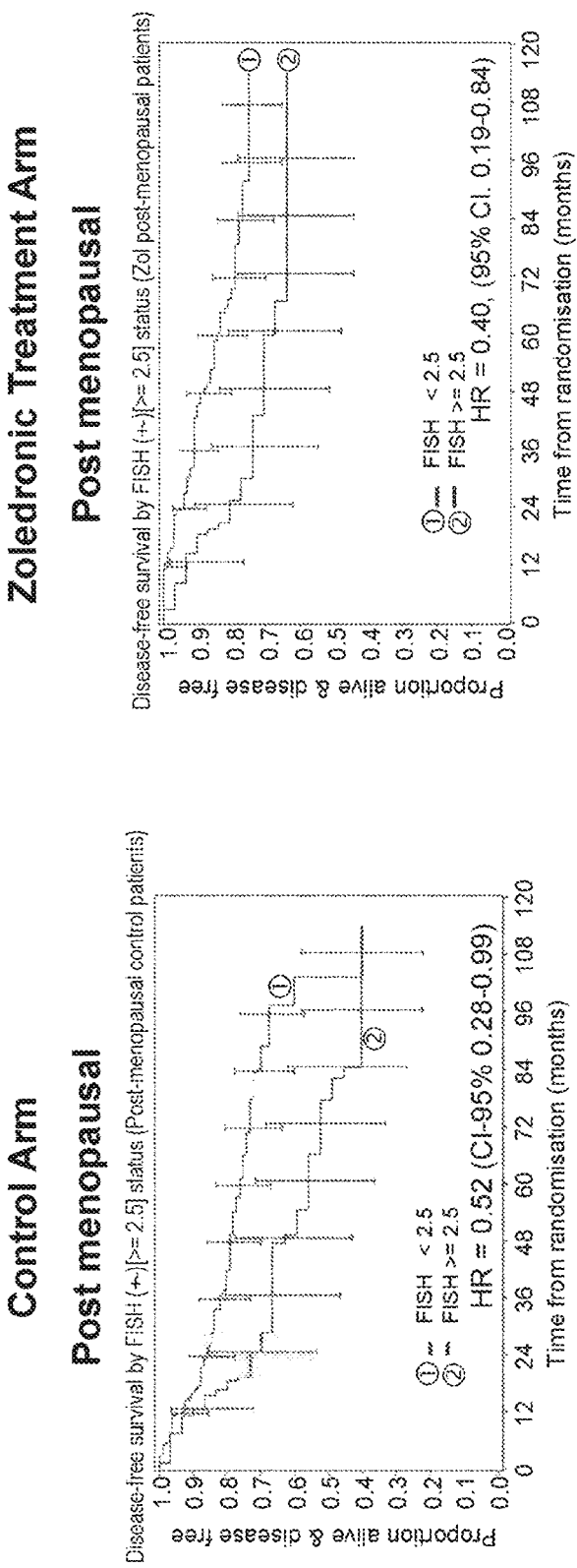

FIG. 28. Predictive value of MAF FISH for the effect of zoledronic acid treatment on the disease free survival (DFS) outcome on post menopausal patients.

Figure 29:
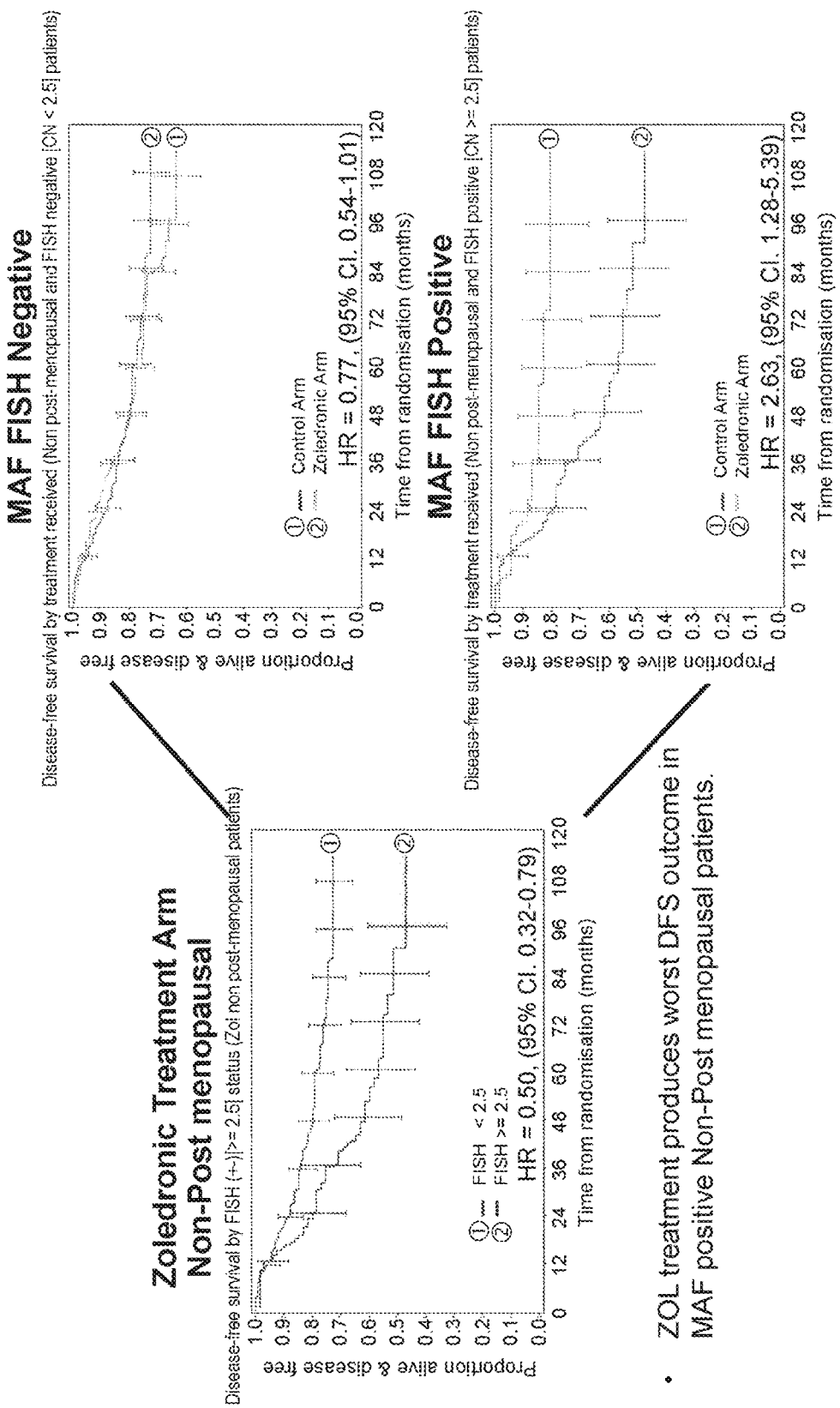

FIG. 29. Predictive value of MAF FISH for the effect of zoledronic acid treatment on the disease free survival (DFS) outcome on non-post menopausal patients.

Figure 30:
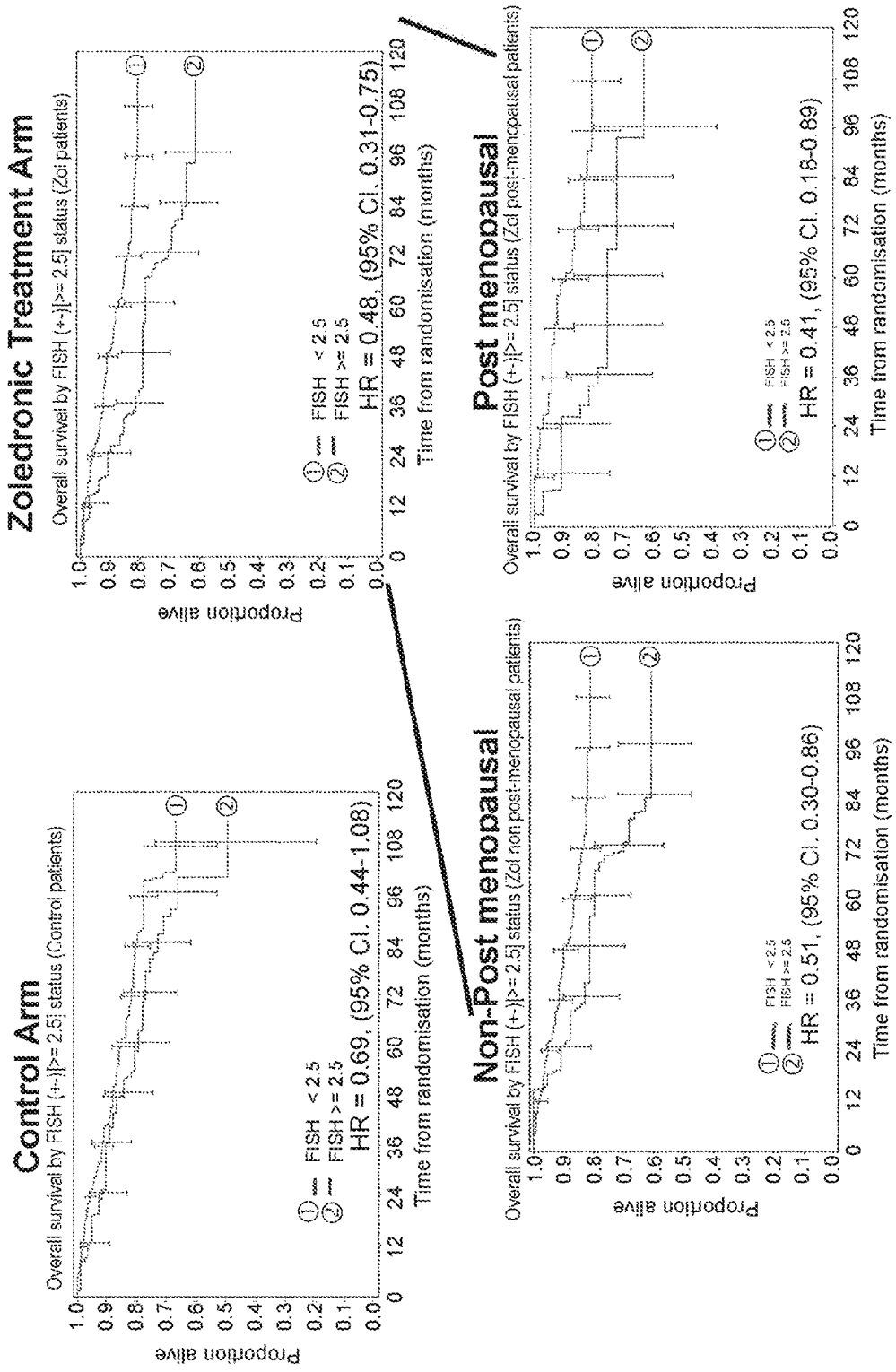

FIG. 30. Predictive value of MAF FISH for the effect of zoledronic acid treatment on the OS outcome.

Figure 31:
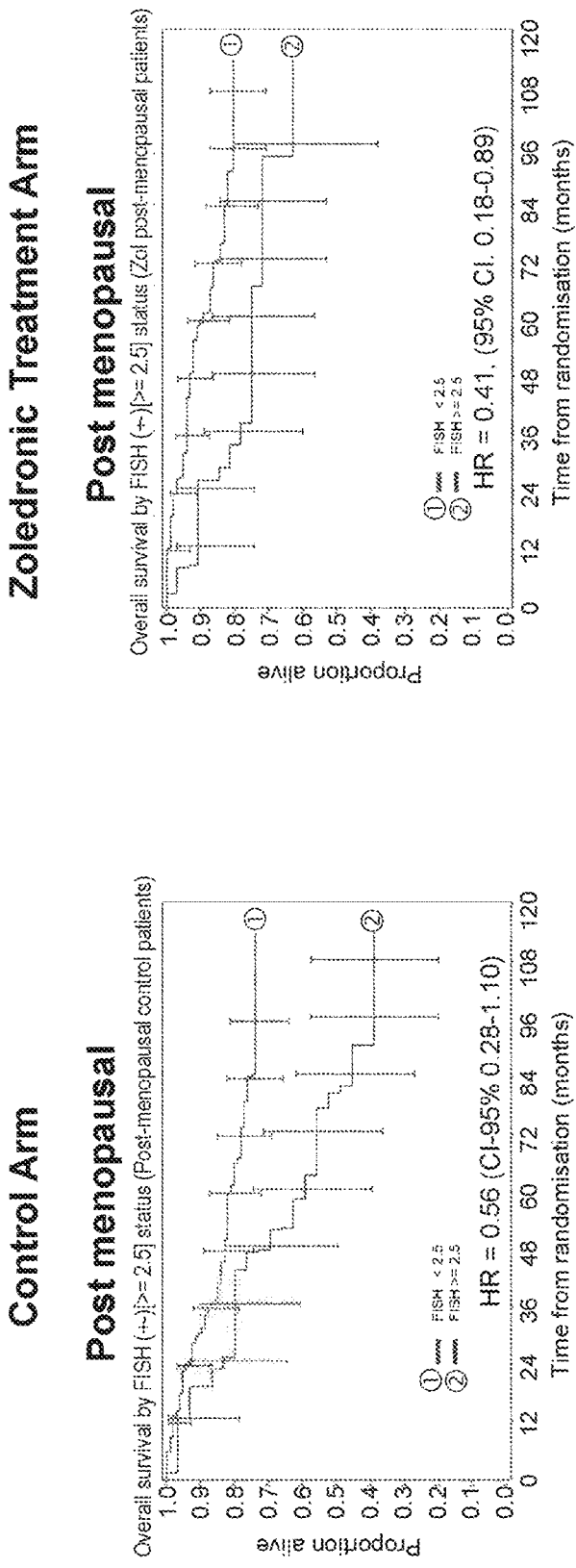

FIG. 31. Predictive value of MAF FISH for the effect of zoledronic acid treatment on the OS outcome in post menopausal patients.

Figure 32:
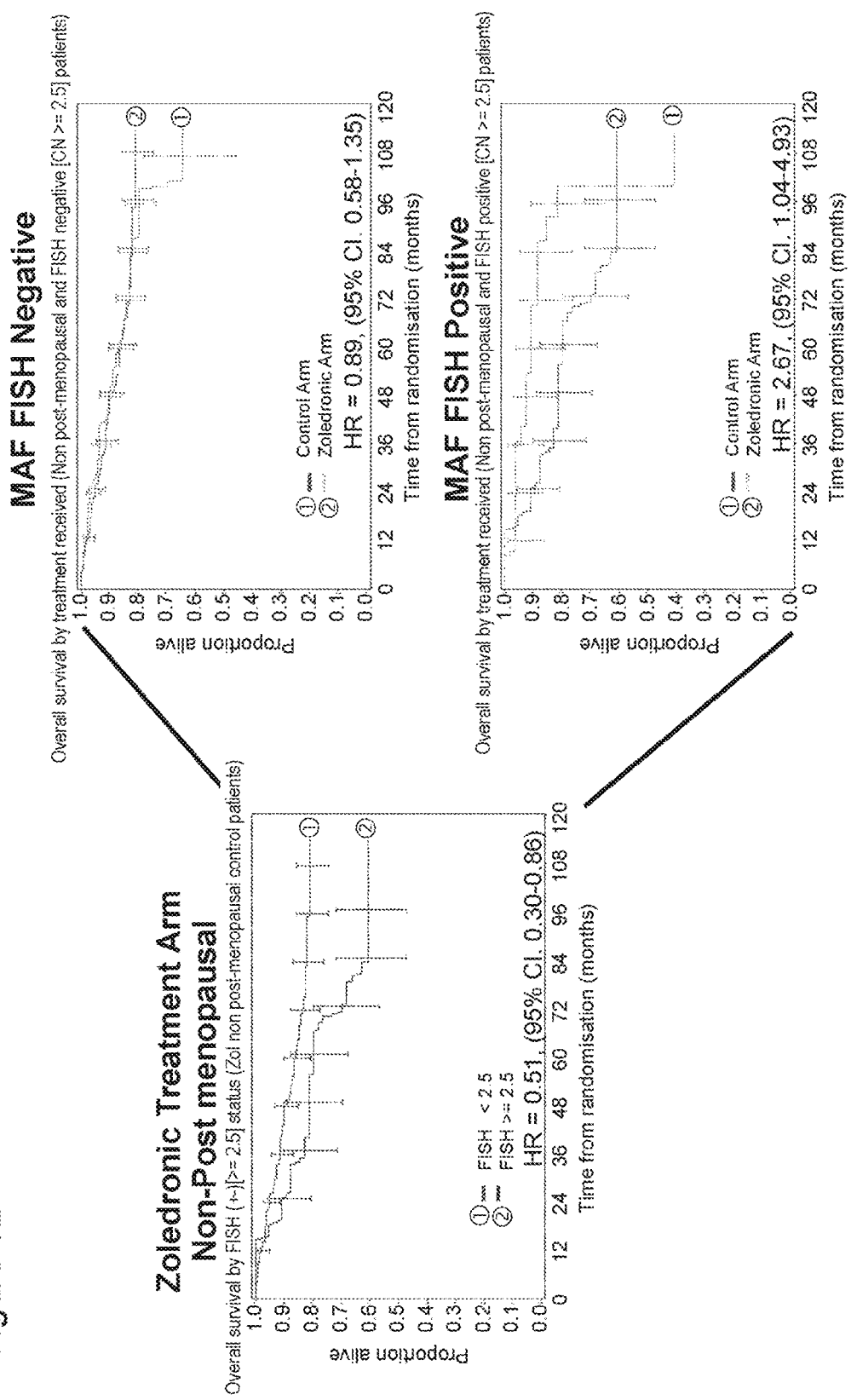

FIG. 32. Predictive value of MAF FISH for the effect of zoledronic acid treatment on the OS outcome in non-post menopausal patients.

DETAILED DESCRIPTION OF THE INVENTION

Definitions of General Terms and Expressions

"And/or" where used herein is to be taken as specific disclosure of each of the two specified features or components with or without the other. For example 'A and/or B' is to be taken as specific disclosure of each of (i) A, (ii) B and (iii) A and B, just as if each is set out individually herein.

The c-MAF gene (v-maf musculoaponeurotic fibrosarcoma oncogene homologue (avian) also known as MAF or MGC71685) is a transcription factor containing a leucine zipper which acts like a homodimer or a heterodimer. Depending on the DNA binding site, the encoded protein can be a transcriptional activator or repressor. The DNA sequence encoding c-MAF is described in the NCBI database under accession number NG_016440 (SEQ ID NO: 1)(coding)). The genomic sequence of c-MAF is set forth in SEQ ID NO:13. The methods of the present invention may utilize either the coding sequence or the genomic DNA sequence. Two messenger RNA are transcribed from said DNA sequence, each of the which will give rise to one of the two c-MAF protein isoforms, the α isoform and the β isoform. The complementary DNA sequences for each of said isoforms are described, respectively, in the NCBI database under accession numbers NM_005360.4 (SEQ ID NO: 2) and NM_001031804.2 (SEQ ID NO: 3). Use of the c-MAF gene to predict the prognosis of ER+ breast cancer can be found in U.S. application Ser. No. 13/878,114, which is incorporated herein by reference in its entirety. Use of the c-MAF gene to predict the prognosis of triple-negative and ER+ breast cancer is described in U.S. application Ser. No. 14/391,085, which is incorporated herein by reference in its entirety. Use of the c-MAF gene to predict the prognosis of thyroid cancer is described in U.S. Prov. Appl. No. 61/801,769, which is incorporated herein by reference in its entirety. Use of the c-MAF gene to predict the prognosis of renal cell carcinoma is described in U.S. Prov. application Ser. No. 14/776,390, which is incorporated herein by reference in its entirety. The use of a gene of interest, including c-MAF and the c-MAF gene locus, and probes to the gene locus, to determine the prognosis of an individual having breast cancer is described in U.S. application Ser. No. 14/776,412, which is incorporated herein by reference in its entirety. Use of the c-MAF gene to predict the prognosis of lung cancer is found in U.S. application Ser. No. 14/405,724, which is incorporated herein by reference in its entirety. Use of the c-MAF gene to predict the prognosis of prostate cancer is found in U.S. application Ser. Nos. 14/050,262 and 14/435,128, which are incorporated herein by reference in their entirety. Use of the c-MAF gene to predict the prognosis of HER2+ cancer is found in U.S. application Ser. No. 15/027,946, which is incorporated herein by reference in its entirety. Use of downstream genes of c-MAF to predict the prognosis of cancer is found in U.S. application Ser. Nos. 15/014,916 and 14/776,453, which are incorporated herein by reference in its entirety.

As used herein, the term "basal-like" "basal-like subtype," "breast cancer of the basal-like subtype" and the like, as used herein, refers to a particular subtype of breast cancer characterized by the two negative receptors ER and HER2 and at least one positive receptor of the group consisting of CK5/6, CK14, CK17 and EGFR. Thus, all sentences in the present application which cite and refer to triple negative breast cancer (ER, HER-2, PgR) can also be cited and refer also to basal-like breast cancer wherein ER and HER2 are negative and wherein at least one of CK5/6, CK14, CK17 and EGFR is positive. Alternatively, "basal-like" also refers to breast cancer characterized by a gene expression profile based on the up-regulation and/or down-regulation of the following ten genes: (1) Forkhead box CI (FOXC 1); (2) Melanoma inhibitory activity (MIA); (3) NDC80 homolog, kinetochore complex component (KNTC2); (4) Centrosomal protein 55 kDa (CEP55); (5) Anillin, actin binding protein (ANLN); (6) Maternal embryonic leucine zipper kinase (MELK); (7) G protein-coupled receptor 160 (GPR160); (8) Transmembrane protein 45B (TMEM45B); (9) Estrogen receptor 1 (ESR1); (10) Forkhead box A1 (FOXA1). Because the gene expression profile used to classify breast cancer tumors as basal-like subtype does not include the estrogen receptor, the progesterone receptor or Her2, both triple negative and non-triple negative breast cancers may be classified as basal-like subtype.

As used herein, "Triple-negative breast cancer" refers to a breast cancer which is characterized by a lack of detectable expression of both ER and PR (preferably when the measures of expression of ER and PR are carried out by the method disclosed by M. Elizabeth H et al., Journal of Clinical Oncology, 28(16): 2784-2795, 2010) and the tumor cells are not amplified for epidermal growth factor receptor type 2 (HER2 or ErbB2), a receptor normally located on the cell surface. Tumor cells are considered negative for expression of ER and PR if less than 5 percent of the tumor cell nuclei are stained for ER and PR expression using standard immunohistochemical techniques. As used herein, tumor cells are considered negative for HER2 overexpression if they yield a test result score of 0 or 1+, or 2+ when tested with a HercepTest™ Kit (Code K5204, Dako North America, Inc., Carpinteria, Calif.), a semi-quantitative immunohistochemical assay using a polyclonal anti-HER2 primary antibody or if they are HER2 FISH negative.

As used herein, "ER+ breast cancer" is understood as breast cancer the tumor cells of which express the estrogen receptor (ER). This makes said tumors sensitive to estrogen, meaning that the estrogen makes the cancerous breast tumor grow. In contrast, "ER– breast cancer" is understood as breast cancer the tumor cells of which do not express the estrogen receptor (ER). Among the ER+ breast cancer are included luminal A and B subtypes.

As used herein, "HER2+" refers to a breast cancer which is characterized by tumor cells with detectable expression of epidermal growth factor receptor type 2 (HER2 or ErbB2) and/or amplification for the HER2 gene, a receptor normally located on the cell surface. As used herein, tumor cells are considered negative for HER2 overexpression if they yield a test result score of 0 or 1+, or 2+ when tested with a HercepTest™ Kit (Code K5204, Dako North America, Inc., Carpinteria, Calif.), a semi-quantitative immunohistochemical assay using a polyclonal anti-HER2 primary antibody or if they are HER2 FISH negative.

In the context of the present invention, a "post-menopausal" subject is understood to be a woman who has undergone menopause and has experienced sixty consecutive months without menstruation. See Coleman et al Lancet Oncol 2014; 15: 997-1006. In certain embodiments, a woman may confirm her postmenopausal status through the measuring of follicle stimulating hormone (FSH).

In the context of the present invention, a "non post-menopausal" subject is any subject who has not gone through menopause and experienced sixty consecutive months without menstruation. "Non post-menopausal" subjects include premenopausal, perimenopausal, and unknown menopausal status women.

In the context of the present invention, "metastasis" is understood as the propagation of a cancer from the organ where it started to a different organ. It generally occurs through the blood or lymphatic system. When the cancer cells spread and form a new tumor, the latter is called a secondary or metastatic tumor. The cancer cells forming the secondary tumor are like those of the original tumor. If a breast cancer, for example, spreads (metastasizes) to the bone, the secondary tumor is formed of malignant breast cancer cells. The disease in the bone is metastatic breast cancer and not bone cancer. In a particular embodiment of the method of the invention, the metastasis is breast cancer which has spread (metastasized) to the bone.

In the context of the present invention, "recurrence" refers to the return of breast cancer following a period of time in which no cancer was detected. Breast cancer may reoccur locally in the breast or tissue surrounding the breast. Breast cancer may also reoccur in nearby lymph nodes or lymph nodes not in the surrounding area. When the breast cancer reoccurs by spreading to other tissues or travels through the blood stream to recur in bones or other organs, it is also referred to as metastasis. As used herein, recurrence also encompasses the risk of recurrence.

In the context of the present invention, "relapse" refers to the situation when symptoms have decreased, but the subject is not cancer free, and then cancer returns. Breast cancer may relapse locally in the breast or tissue surrounding the breast. Breast cancer may also relapse in nearby lymph nodes or lymph nodes not in the surrounding area. When the breast cancer relapses by spreading to other tissues or travels through the blood stream to recur in bones or other organs, it is also referred to as metastasis. As used herein, relapse also encompasses the risk of relapse.

As used herein, the term "disease free survival" refers to the length of time after primary treatment for a cancer ends that the patient survives without any signs or symptoms of that cancer. In some embodiments, disease free survival is referred to as DFS, relapse-free survival, or RFS.

As used herein, the term "overall survival" or "OS" refers to the length of time from either the date of diagnosis or the start of treatment for a cancer that patients diagnosed with the disease are still alive.

As used herein, the term "subject" or "patient" refers to all animals classified as mammals and includes but is not limited to domestic and farm animals, primates and humans, for example, human beings, non-human primates, cows, horses, pigs, sheep, goats, dogs, cats, or rodents. Preferably, the subject is a human man or woman of any age or race.

The terms "poor" or "good", as used herein to refer to a clinical outcome, mean that the subject will show a favorable or unfavorable outcome. As will be understood by those skilled in the art, such an assessment of the probability, although preferred to be, may not be correct for 100% of the subjects to be diagnosed. The term, however, requires that a statistically significant portion of subjects can be identified as having a predisposition for a given outcome. Whether a portion is statistically significant can be determined readily by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least about 50%, at least about 60%, at least about 70%, at least about 80%, at least about 90% at least about 95%. The p-values are, preferably, 0.05, 0.01, 0.005, or 0.0001 or less. More preferably, at least about 60 percent, at least about 70 percent, at least about 80 percent or at least about 90 percent of the subjects of a population can be properly identified by the method of the present invention.

In the present invention "tumor sample" is understood as a sample (e.g., tumor tissue, circulating tumor cell, circulating tumor DNA) originating from the primary breast cancer tumor. Said sample can be obtained by conventional methods, for example biopsy, using methods well known by the persons skilled in related medical techniques. The methods for obtaining a biopsy sample include splitting a tumor into large pieces, or microdissection, or other cell separating methods known in the art. The tumor cells can additionally be obtained by means of cytology through aspiration with a small gauge needle. To simplify sample preservation and handling, samples can be fixed in formalin and soaked in paraffin or first frozen and then soaked in a tissue freezing medium such as OCT compound by means of immersion in a highly cryogenic medium which allows rapid freezing.

In the context of the present invention, "functionally equivalent variant of the c-MAF protein" is understood as (i) variants of the c-MAF protein (SEQ ID NO: 4 or SEQ ID NO: 5) in which one or more of the amino acid residues are substituted by a conserved or non-conserved amino acid residue (preferably a conserved amino acid residue), wherein such substituted amino acid residue may or may not be one encoded by the genetic code, or (ii) variants comprising an insertion or a deletion of one or more amino acids and having the same function as the c-MAF protein, i.e., to act as a DNA binding transcription factor. Variants of the c-MAF protein can be identified using methods based on the capacity of c-MAF for promoting in vitro cell proliferation as shown in international patent application WO2005/046731 (hereby incorporated by reference in its entirety), based on the capacity of the so-called inhibitor for blocking the transcription capacity of a reporter gene under the control of cyclin D2 promoter or of a promoter containing the c-MAF responsive region (MARE or c-MAF responsive element) in cells expressing c-MAF as described in WO2008098351 (hereby incorporated by reference in its entirety), or based on the capacity of the so-called inhibitor for blocking reporter gene expression under the control of the IL-4 promoter in response to the stimulation with PMA/ionomycin in cells expressing NFATc2 and c-MAF as described in US2009048117A (hereby incorporated by reference in its entirety).

The variants according to the invention preferably have sequence similarity with the amino acid sequence of any of the c-MAF protein isoforms (SEQ ID NO: 4 or SEQ ID NO: 5) of at about least 50%, at least about 60%, at about least 70%, at least about 80%, at least about 90%, at least about 91%, at least about 92%, at least about 93%, at least about 94%, at least about 95%, at least about 96%, at least about 97%, at about least 98% or at about least 99%. The degree of similarity between the variants and the specific c-MAF protein sequences defined previously is determined using algorithms and computer processes which are widely known by the persons skilled in the art. The similarity between two amino acid sequences is preferably determined using the BLASTP algorithm [BLAST Manual, Altschul, S., et al., NCBI NLM NIH Bethesda, Md. 20894, Altschul, S., et al., J. Mol. Biol. 215: 403-410 (1990)].

As used herein, "agent for avoiding or preventing bone remodelling" refers to any molecule capable of preventing, inhibiting, treating, reducing, or stopping bone degradation either by stimulating the osteoblast proliferation or inhibiting the osteoclast proliferation or fixing the bone structure. Agents for avoiding or prevent bone remodeling include agents for avoiding or preventing bone degradation and include agents for avoiding or preventing bone synthesis.

As used herein, a "c-MAF inhibitory agent" refers to any molecule capable of completely or partially inhibiting the c-MAF gene expression, both by preventing the expression product of said gene from being produced (interrupting the c-MAF gene transcription and/or blocking the translation of the mRNA coming from the c-MAF gene expression) and by directly inhibiting the c-MAF protein activity. C-MAF gene expression inhibitors can be identified using methods based on the capacity of the so-called inhibitor to block the capacity of c-MAF to promote the in vitro cell proliferation, such as shown in the international patent application WO2005/046731 (the entire contents of which are hereby incorporated by reference), based on the capacity of the so-called inhibitor to block the transcription capacity of a reporter gene under the control of the cyclin D2 promoter or of a promoter containing the c-MAF response region (MARE or c-MAF responsive element) in cells which express c-MAF such as described in WO2008098351 (the entire contents of which are hereby incorporated by reference) or based on the capacity of the so-called inhibitor to block the expression of a reporter gene under the control of the IL-4 promoter in response to the stimulation with PMA/ionomycin in cells which express NFATc2 and c-MAF such as described in US2009048117A (the entire contents of which is hereby incorporated by reference).

As used herein, Mammalian target of rapamycin (mTOR) or "mTor" refers to those proteins that correspond to EC 2.7.11.1. mTor enzymes are serine/threonine protein kinases and regulate cell proliferation, cell motility, cell growth, cell survival, and transcription.

As used herein, an "mTor inhibitor" refers to any molecule capable of completely or partially inhibiting the mTor gene expression, both by preventing the expression product of said gene from being produced (interrupting the mTor gene transcription and/or blocking the translation of the mRNA coming from the mTor gene expression) and by directly inhibiting the mTor protein activity. Including inhibitors that have a dual or more targets and among them mTor protein activity.

As used herein, "Src" refers to those proteins that correspond to EC 2.7.10.2. Src is a non-receptor tyrosine kinase and a proto-oncogene. Src may play a role in cell growth and embryonic development.

As used herein, a "Src inhibitor" refers to any molecule capable of completely or partially inhibiting the Src gene expression, both by preventing the expression product of said gene from being produced (interrupting the Src gene transcription and/or blocking the translation of the mRNA coming from the Src gene expression) and by directly inhibiting the Src protein activity.

As used herein, "Prostaglandin-endoperoxide synthase 2", "cyclooxygenase-2" or "COX-2" refers to those proteins that correspond to EC 1.14.99.1. COX-2 is responsible for converting arachidonic acid to prostaglandin endoperoxide H2.

As used herein, a "COX-2 inhibitor" refers to any molecule capable of completely or partially inhibiting the COX-2 gene expression, both by preventing the expression product of said gene from being produced (interrupting the COX-2 gene transcription and/or blocking the translation of the mRNA coming from the COX-2 gene expression) and by directly inhibiting the COX-2 protein activity.

As used herein "outcome" or "clinical outcome" refers to the resulting course of disease and/or disease progression and can be characterized for example by recurrence, period of time until recurrence, relapse, metastasis, period of time until metastasis, number of metastases, number of sites of metastasis and/or death due to disease. For example a good clinical outcome includes cure, prevention of recurrence, prevention of metastasis and/or survival within a fixed period of time (without recurrence), and a poor clinical outcome includes disease progression, metastasis and/or death within a fixed period of time.

As used herein, "invasive disease free survival" or "IDFS" refers to, in cancer, the length of time after primary treatment for a cancer ends that the patient survives without any signs or symptoms of that cancer invading the same breast parenchyma as the original primary tumor or other tissues. In some embodiments, IDFS includes: ipsilateral invasive breast tumor recurrence, local or regional invasive breast cancer recurrence, metastatic or distant recurrence, death attributable to any cause, including breast cancer, contralateral invasive breast cancer, and second primary invasive cancer (non-breast but excluding basal-cell or squamous skin cancers). See Coleman et al Lancet Oncol 2014; 15: 997-1006.

In the present invention, "diagnosis of metastasis in a subject with breast cancer" is understood as identifying a disease (metastasis) by means of studying its signs, i.e., in the context of the present invention by means of increased c-MAF gene expression levels (i.e., overexpression) in the breast cancer tumor tissue with respect to a control sample.

In the present invention "prognosis of the tendency to develop metastasis in a subject with breast cancer" is understood as knowing based on the signs if the breast cancer that said subject has will metastasize in the future. In the context of the present invention, the sign is c-MAF gene overexpression in tumor tissue.

In the context of the present invention, it is understood that "a subject has a positive diagnosis for metastasis" when the breast cancer suffered by said subject has metastasized to other organs of the body, in a particular embodiment, to the bone. The term is similarly used for recurrence and relapse.

The person skilled in the art will understand that the prediction of the tendency for a primary tumor to metastasize, relapse or reoccur is not intended to be correct for all the subjects to be identified (i.e., for 100% of the subjects). Nevertheless, the term requires enabling the identification of a statistically significant part of the subjects (for example, a cohort in a cohort study). Whether a part is statistically significant can be determined in a simple manner by the person skilled in the art using various well known statistical evaluation tools, for example, the determination of confidence intervals, determination of p values, Student's T test, Mann-Whitney test, etc. Details are provided in Dowdy and Wearden, Statistics for Research, John Wiley and Sons, New York 1983. The preferred confidence intervals are at least about 90%, at least about 95%, at least about 97%, at least 98% or at least 99%. The p values are preferably 0.1, 0.05, 0.01, 0.005 or 0.0001. More preferably, at least about 60%, at least about 70%, at least about 80% or at least about 90% of the subjects of a population can be suitably identified by the method of the present invention.

As used herein, "poor prognosis" indicates that the subject is expected e.g. predicted to not survive and/or to have, or is at high risk of having, recurrence, relapse, or distant metastases within a set time period. The term "high" is a relative term and, in the context of this application, refers to the risk of the "high" expression group with respect to a clinical outcome (recurrence, distant metastases, etc.). A "high" risk can be considered as a risk higher than the average risk for a heterogeneous cancer patient population. In the study of Paik et al. (2004), an overall "high" risk of recurrence was considered to be higher than 15 percent. The risk will also vary in function of the time period. The time period can be, for example, five years, ten years, fifteen years or even twenty years of initial diagnosis of cancer or after the prognosis was made.

"Reference value", as used herein, refers to a laboratory value used as a reference for values/data obtained by laboratory examinations of patients or samples collected from patients. The reference value or reference level can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from a population of subjects of the chronological age matched group, or based on a pool of samples including or excluding the sample to be tested.

The term "treatment", as used herein, refers to any type of therapy, which aims at terminating, preventing, ameliorating or reducing the susceptibility to a clinical condition as described herein. In an embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, or immune deficiency.

As used herein, "sample" or "biological sample" means biological material isolated from a subject. The biological sample may contain any biological material suitable for determining the expression level of the c-MAF gene. The sample can be isolated from any suitable biological tissue or fluid such as, for example, tumor tissue, blood, blood plasma, serum, urine or cerebral spinal fluid (CSF).

As used herein, the term "expression level" of a gene as used herein refers to the measurable quantity of gene product produced by the gene in a sample of the subject, wherein the gene product can be a transcriptional product or a translational product. Accordingly, the expression level can pertain to a nucleic acid gene product such as mRNA or cDNA or a polypeptide gene product. The expression level is derived from a subject's sample and/or a reference sample or samples, and can for example be detected de novo or correspond to a previous determination. The expression level can be determined or measured, for example, using microarray methods, PCR methods (such as qPCR), and/or antibody based methods, as is known to a person of skill in the art.

"Increased expression level" is understood as the expression level when it refers to the levels of the c-MAF gene greater than those in a reference sample or control sample. These increased levels can be caused without excluding other mechanisms by a gene or 16q23 or 16q22-24 chromosomal locus amplification, copy gain or translocation. Particularly, a sample can be considered to have high c-MAF expression level when the expression level in the sample isolated from the patient is at least about 1.1 times, 1.2 times, 1.3 times, 1.4 times, 1.5 times, 2 times, 2.1 times, 2.2 times, 2.3 times, 2.4 times, 2.5 times, 3 times, 4 times, 5 times, 10 times, 20 times, 30 times, 40 times, 50 times, 60 times, 70 times, 80 times, 90 times, 100 times or even more with respect to the reference or control. In embodiments, an "increased expression level" is a "high" expression level. An expression level that is "not increased" or "non increased" is any value that is not included in the definition of "increased" expression level, including a value equal or the reference or control level or a decreased expression level in comparison to a reference or control level.

"Decreased expression level" is understood as the expression level when it refers to the levels of the c-MAF gene less than those in a reference sample or control sample. This decreased level can be caused without excluding other mechanisms by a gene or 16q23 or 16q22-24 chromosomal locus deletion. Particularly, a sample can be considered to have decreased c-MAF expression levels when the expression level in the sample isolated from the patient is at least about 1.1 times, 1.2 times, 1.3 times, 1.4 times, 1.5 times, 2 times, 2.1 times, 2.2 times, 2.3 times, 2.4 times, 2.5 times, 3 times, 4 times, 5 times, 10 times, 20 times, 30 times, 40 times, 50 times, 60 times, 70 times, 80 times, 90 times, 100 times or even less with respect to the reference or control. In embodiments, a "decreased expression level" is a "low" expression level.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population.

In the present invention, "increased gene copy number" is understood as when the c-MAF gene copy number is more than the copy number that a reference sample or control sample has. These increased gene copy number can be caused without excluding other mechanisms by a gene or 16q23 or 16q22-24 chromosomal locus amplification, copy gain or translocation. In particular, it can be considered that a sample has an increased c-MAF copy number when the copy number is more than 2 copies, for example, 2.1, 2.2, 2.3, 2.4, 2.5, 2.6, 2.7, 2.8, 2.9, 3, 4, 5, 6, 7, 8, 9 or 10 copies, and even more than 10 copies of the c-MAF gene. In embodiments, "increased gene copy number" is determined based on an average of copies per cells counted. In embodiments, it can be considered that a sample has an increased c-MAF copy number when the average copy number per cell counted is more than 2 copies, for example, 2.1, 2.2, 2.3, 2.4, 2.5, 2.6, 2.7, 2.8, 2.9, 3, 4, 5, 6, 7, 8, 9 or 10 copies, and even more than 10 copies of the c-MAF gene.

In the present invention, "decreased gene copy number" is understood as when the c-MAF gene copy number is less than the copy number that a reference sample or control sample has. These decreased gene copy number can be caused without excluding other mechanisms by a gene or 16q23 or 16q22-24 chromosomal locus deletions. In particular, it can be considered that a sample has a decreased c-MAF copy number when the copy number is less than 2 copies of the c-MAF gene.

In the present invention, a "not increased gene copy number" is understood as when the c-MAF gene copy number or the average c-MAF gene copy number is less than the copy number that a reference sample or positive for the increase sample has. The not increased gene copy number can be caused without excluding other mechanisms by no increase in gene or 16q23 or 16q22-24 chromosomal locus amplification, copy gain or translocation. In particular, it can be considered that a sample has not an increased c-MAF copy number or c-MAF average copy number when the copy number is less than 2.1, 2.2, 2.3, 2.4, 2.5, 2.6, 2.7, 2.8, 2.9 copies of the c-MAF gene.

The term "amplification of a gene" as understood herein refers to a process through which various copies of a gene or of a gene fragment are formed in an individual cell or a cell line. The copies of the gene are not necessarily located in the same chromosome. The duplicated region is often called an "amplicon". Normally, the amount of mRNA produced, i.e., the gene expression level also increases in proportion to the copy number of a particular gene.

The term "gain" refers any chromosomal copy number increase from the norm, i.e., in a diploid organism, 3 copies of a gene in a cell would be a gain. In some embodiments, "gain" includes the term "copy gain", and is used synonymously with "copy number".

"Probe", as used herein, refers to an oligonucleotide sequence that is complementary to a specific nucleic acid sequence of interest. In some embodiments, the probes may be specific to regions of chromosomes that are known to undergo translocations. In some embodiments, the probes have a specific label or tag. In some embodiments, the tag is a fluorophore. In some embodiments, the probe is a DNA in situ hybridization probe whose labeling is based on the stable coordinative binding of platinum to nucleic acids and proteins. In some embodiments, the probe is described in U.S. Pat. Nos. 9,127,302 and 9,134,237, which are incorporated by reference in their entirety, or as described in Swennenhuis et al. "Construction of repeat-free fluorescence in situ hybridization probes" Nucleic Acids Research 40(3): e20 (2012).

"Tag" or "label", as used herein, refers to any physical molecule that is directly or indirectly associated with a probe, allowing the probe or the location of the probed to be visualized, marked, or otherwise captured.

"Translocation", as used herein, refers to the exchange of chromosomal material in unequal or equal amounts between chromosomes. In some cases, the translocation is on the same chromosome. In some cases, the translocation is between different chromosomes. Translocations occur at a high frequency in many types of cancer, including breast cancer and leukemia. Translocations can be either primary reciprocal translocations or the more complex secondary translocations. There are several primary translocations that involve the immunoglobin heavy chain (IgH) locus that are believed to constitute the initiating event in many cancers. (Eychène, A., Rocques, N., and Puoponnot, C., A new MAFia in cancer. 2008. Nature Reviews: Cancer. 8: 683-693.)

"Polyploid" or "polyploidy", as used herein, indicates that the cell contains more than two copies of a gene of interest. In some instances, the gene of interest is MAF. In some embodiments, polyploidy is associated with an accumulation of expression of the gene of interest. In some embodiments, polyploidy is associated with genomic instability. In some embodiments, the genomic instability may lead to chromosome translocations.

"Whole genome sequencing", as used herein, is a process by which the entire genome of an organism is sequenced at a single time. See, e.g., Ng., P. C. and Kirkness, E. F., Whole Genome Sequencing. 2010. Methods in Molecular Biology. 628: 215-226.

"Exome sequencing", as used herein, is a process by which the entire coding region of the DNA of an organism is sequenced. In exome sequencing, the mRNA is sequenced. The untranslated regions of the genome are not included in exome sequencing. See, e.g., Choi, M. et al., Genetic diagnosis by whole exome capture and massively parallel DNA sequencing. 2009. PNAS. 106(45): 19096-19101.

As used herein, "binding member" describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, receptor-ligand and enzyme-substrate. In some embodiments, the binding member is an antibody. In some embodiments, the binding member is an antibody that binds a c-MAF antigen.

As used herein, "CDR region" or "CDR" is intended to indicate the hypervariable regions of the heavy and light chains of the immunoglobulin as defined by Kabat et al., (1991) Sequences of Proteins of Immunological Interest, 5th Edition. US Department of Health and Human Services, Public Service, NIH, Washington. An antibody typically contains 3 heavy chain CDRs, termed HCDR1, HCDR2, and HCDR3, and 3 light chain CDRs, termed LCDR1, LCDR2 and LCDR3. The term CDR or CDRs is used here in order to indicate one of these regions or several, or even the whole, of these regions which contain the majority of the amino acid residues responsible for the binding by affinity of the antibody for the antigen or the epitope which it recognizes. Among the six CDR sequences, the third CDR of the heavy chain (HCDR3) has a greatest size variability i.e. greater diversity, essentially due to the mechanism known in the art as V(D)J rearrangement of the V, D and J gene segments of the germline immunoglobulin heavy chain gene locus. The HCDR3 may be as short as two amino acids or as long as 26 amino acids, or may have any length in between these two extremes. CDR length may also vary according to the length that can be accommodated by the particular underlying framework. Functionally, HCDR3 can play an important role in the determination of the specificity of the antibody (Segal et al., (1974) Proc Natl Acad Sci USA. 71(11): 4298-302; Amit et al., (1986) Science 233(4765): 747-53; Chothia et al., (1987) J. Mol. Biol. 196(4): 901-17; Chothia et al., (1989) Nature 342(6252): 877-83; Caton et al., (1990) J. Immunol. 144(5): 1965-8; Sharon (1990a) PNAS USA. 87(12): 4814-7, Sharon (1990b) J. Immunol. 144: 4863-4869, Kabat et al., (1991) Sequences of Proteins of Immunological Interest, 5th Edition. US Department of Health and Human Services, Public Service, NIH, Washington).

As used herein, "antibody", "antibody molecule", or "antibodies" describes an immunoglobulin whether naturally, or partly, or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids. Antibody fragments that comprise an antibody antigen-binding site include, but are not limited to, molecules such as Fab, Fab', F(ab')2, Fab'-SH, scFv, Fv, dAb and Fd. Various other antibody molecules including one or more antibody antigen-binding sites have been engineered, including for example Fab2, Fab3, diabodies, triabodies, tetrabodies, camelbodies, nanobodies and minibodies. Antibody molecules and methods for their construction and use are described in Hollinger & Hudson (2005) Nature Biot. 23(9): 1126-1136.

As used herein, "antibody molecule" should be construed as covering any binding member or substance having an antibody antigen-binding site with the required specificity and/or binding to antigen. Thus, this term covers functional antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described for example in EP0120694A (Boss et al) and EP0125023A (Cabilly et al), which are incorporated herein in their entirety.

As used herein, "functional fragment or variant" of, for example, a binding member of the present invention means a fragment or variant of a binding member that retains at least some function of a full binding member (e.g., the ability to specifically bind to antigen such as Maf).

"Tumor tissue sample" is understood as the tissue sample originating from the breast cancer tumor, including but not limited to circulating tumor cells and circulating tumor DNA. Said sample can be obtained by conventional methods, for example biopsy, using methods well known by the persons skilled in related medical techniques.

"Osteolytic bone metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

Method for Designing Customized Therapy of the Invention in Patients with Breast Tumors The present invention is directed to identifying subjects suffering from breast cancer who will benefit from treatment with particular agents and/or therapies. In some embodiments, the invention is directed to identifying subjects suffering from breast cancer who will not benefit from treatment with particular agents and therapies. In some embodiments, the subjects have a high expression level, copy number, amplification, gain and/or translocation of c-MAF. In certain embodiments, the subjects have a low expression level, copy number, amplification, gain and/or translocation of c-MAF. In particular embodiments, the cancer is triple-negative breast cancer. In other embodiments, the cancer is ER+ breast cancer. In further embodiments, the cancer is ER-breast cancer. In still further embodiments, the cancer is HER2+ breast cancer. In some embodiments, the cancer is a basal-like breast cancer. In one embodiment, the subjects are post-menopausal. In an embodiment, the subjects are non-post menopausal. As described U.S. application Ser. No. 14/391,085, U.S. Prov. Appl. No. 61/801,769, U.S. Prov. application Ser. No. 14/776,390, U.S. application Ser. No. 14/776,412, U.S. application Ser. No. 14/405,724, U.S. application Ser. No.

14/050,262, U.S. application Ser. No. 14/435,128, U.S. application Ser. No. 15/027,946 U.S. application Ser. No. 15/014,916, and U.S. application Ser. No. 14/776,453, each of which is incorporated herein by reference in its entirety, the levels of c-MAF can be used to diagnosis metastasis, relapse or recurrence, or to predict the tendency of a tumor to undergo metastasis, relapse or recurrence. Therefore, as described in the present invention, given that the c-MAF gene overexpression in breast cancer cells is related to the presence of metastasis, relapse or recurrence, the c-MAF gene expression levels allow making decisions in terms of the most suitable therapy for the subject suffering said cancer. In an embodiment, the invention comprises quantifying only the c-MAF gene expression level as a single marker, i.e., the method does not involve determining the expression level of any additional marker.

Thus, in one embodiment the invention relates to an in vitro method for designing a customized therapy for a subject with breast cancer, which comprises a) quantifying the c-MAF gene expression level, copy number, amplification, or gain in a tumor sample of said subject and b) comparing the expression level, copy number, amplification or gain obtained with the expression level, copy number, amplification or gain of said gene in a control sample, wherein the therapy is determined based on the c-MAF gene expression level, copy number, amplification or gain in the subject. In some embodiments, the subject has a high c-MAF gene expression level. In other embodiments, the subject has a low c-MAF gene expression level. In certain embodiments, the subject is administered an agent that avoids and/or prevents bone remodelling, including agents that avoid or prevent bone degradation. In embodiments, the subject is administered an agent that treats the cancer. In further embodiments, the subject is administered a c-MAF inhibitory agent. In particular embodiments, the agent that avoids and/or prevents bone remodelling or the c-MAF inhibitory agent is any agent disclosed in U.S. Publ. Nos. 2014/0057796 and 2015/0293100 and U.S. application Ser. No. 15/027,946, which are incorporated herein by reference in their entireties.

In one embodiment, the invention relates to an in vitro method for designing a customized therapy for a subject having breast cancer which comprises i) quantifying the c-MAF gene expression level, copy number, amplification, or gain in a sample of said subject and ii) comparing the expression level, copy number, amplification, or gain obtained in i) with a reference value, wherein if the expression level, copy number, amplification, or gain is not increased with respect to said reference value, then said subject is susceptible to receive a therapy aiming to prevent and/or treat bone remodeling or improves disease free survival or overall survival. In some embodiments, the subject is non-postmenopausal. In other embodiments, the subject is postmenopausal. In an embodiment, the subject is administered the agent aiming to prevent and/or treat bone remodelling. In embodiments, the subject is administered an agent that improves disease free survival or overall survival. In further embodiments, the subject is administered a c-MAF inhibitory agent.

In another embodiment, the invention relates to an in vitro method for designing a customized therapy for a non-postmenopausal subject having breast cancer which comprises i) quantifying the c-MAF gene expression level, copy number, amplification, or gain in a sample of said subject and ii) comparing the expression level, copy number, amplification, or gain obtained in i) with a reference value, wherein if the expression level, copy number, amplification, or gain is increased with respect to said reference value, then said subject is not susceptible to receive a therapy aiming to prevent and/or treat bone remodeling and/or improves disease free survival or overall survival. In some embodiments, the subject is not administered the agent aiming to prevent and/or treat bone remodeling and/or improves disease free survival or overall survival.

In another embodiment, the invention relates to an in vitro method for designing a customized therapy for a postmenopausal subject having breast cancer which comprises i) quantifying the c-MAF gene expression level, copy number, amplification, or gain in a sample of said subject and ii) comparing the expression level, copy number, amplification, or gain obtained in i) with a reference value, wherein if the expression level, copy number, amplification, or gain is increased with respect to said reference value, then said subject is susceptible to receive a therapy aiming to prevent and/or treat bone remodeling and/or improves disease free survival or overall survival. In some embodiments, the subject is administered the agent aiming to prevent and/or treat bone remodeling and/or the therapy to improve disease free survival or overall survival.

In another embodiment, the invention relates to an in vitro method for designing a customized therapy for a postmenopausal subject having breast cancer which comprises i) quantifying the c-MAF gene expression level, copy number, amplification, or gain in a sample of said subject and ii) comparing the expression level, copy number, amplification, or gain obtained in i) with a reference value, wherein if the expression level, copy number, amplification, or gain is not increased with respect to said reference value, then said subject is not susceptible to receive a therapy aiming to prevent and/or treat bone remodeling and/or improves disease free survival or overall survival. In some embodiments, the subject is not administered the agent aiming to prevent and/or treat bone remodeling and/or improves disease free survival or overall survival.

In an embodiment, the invention relates to a method for the treatment of bone metastasis in a subject having breast cancer and having decreased c-MAF levels in a metastatic tumor sample with respect to a control sample comprising administering an agent capable of preventing or inhibiting bone remodeling and or improve disease free survival or overall survival, wherein the agent capable of avoiding or preventing bone remodeling or improving disease free survival or overall survival is selected from the group consisting of: a bisphosphonate, a RANKL inhibitor, PTH, PTHLH inhibitor (including neutralizing antibodies and peptides), a PRG analog, strontium ranelate, a DKK-1 inhibitor, a dual MET and VEGFR2 inhibitor, an estrogen receptor modulator, an EGFR inhibitor, calcitonin, Radium-223, a CCR5 antagonist, a Src kinase inhibitor, a COX-2 inhibitor, an mTor inhibitor, and a cathepsin K inhibitor. In some embodiments, the subject is non-postmenopausal. In other embodiments, the subject is postmenopausal.

In another embodiment, the invention relates to a method for the treatment of bone metastasis in a postmenopausal subject having breast cancer and having increased c-MAF levels in a metastatic tumor sample with respect to a control sample comprising administering an agent capable of preventing or inhibiting bone remodeling and/or an agent that improves disease free survival or overall survival, wherein the agent capable of avoiding or preventing bone remodeling and/or improving disease free survival or overall survival is selected from the group consisting of: a bisphosphonate, a RANKL inhibitor, PTH, PTHLH inhibitor (including neutralizing antibodies and peptides), a PRG analog, strontium ranelate, a DKK-1 inhibitor, a dual MET and VEGFR2 inhibitor, an estrogen receptor modulator, an EGFR inhibitor, calcitonin, Radium-223, a CCR5 antagonist, a Src kinase inhibitor, a COX-2 inhibitor, an mTor inhibitor, and a cathepsin K inhibitor.

In certain embodiments, the subject is administered an agent that avoids and/or prevents bone remodelling, including agents that avoid or prevent bone degradation. In embodiments, the subject is administered an agent that avoids or prevents bone degradation.

Once the c-MAF gene expression level, copy number, amplification or gain in the sample have been measured and compared with the control sample, the expression level, copy number, amplification or gain of said gene, in combination with the menopausal status of the subject indicates whether the subject is susceptible to receiving therapy aiming to prevent (if the subject has yet to undergo metastasis) and/or treat metastasis (if the subject has already experienced metastasis), relapse or recurrence and or a therapy or agent intended to avoid or prevent bone remodelling.

In some embodiments, a copy number of MAF or average copy number of MAF per cell as measured using FISH≥2.1, 2.2, 2.3, 2.4, 2.5, 2.6, 2.7, 2.8, 2.9 or 3.0 is considered a high value. In embodiments, the MAF FISH value is ≥2.2. In certain embodiments, the MAF FISH value is ≥2.3. In other embodiments, the MAF FISH value is ≥2.4. In further embodiments, the MAF FISH value is ≥2.5. In other embodiments, the copy number of c-MAF as measured using FISH is <2.1, 2.2, 2.3, 2.4, 2.5, 2.6, 2.7, 2.8, 2.9 copies of the c-MAF gene.

In a particular embodiment, the subject has metastasis or a prognosis to undergo metastasis. In some embodiments, the metastasis is a bone metastasis. In a further embodiment, the bone metastasis is osteolytic metastasis.

In some embodiments, the method comprises in a first step quantifying the c-MAF gene expression level, copy number, gain or amplification in a tumor sample in a subject suffering from breast cancer.

In some embodiments, the sample is a primary tumor tissue sample of the subject. In a second step, the c-MAF gene expression level, copy number, amplification or gain obtained in the tumor sample of the subject is compared with the expression level, copy number, amplification or gain of said gene in a control sample. The determination of the c-MAF gene expression levels, copy number, amplification or gain must be related to values of a control sample or reference sample. Depending on the type of tumor to be analyzed, the exact nature of the control sample may vary. Thus, in some embodiments, the reference sample is a tumor tissue sample of a subject with breast cancer that has not metastasized, relapsed or reoccurred or that corresponds to the median value of the c-MAF gene expression levels, copy number, amplification or gain measured in a tumor tissue collection in biopsy samples of subjects with breast cancer which has not metastasized, relapsed or reoccurred.

In one embodiment, the methods of the invention comprise in a second step comparing the c-MAF gene expression level, copy number, amplification or gain obtained in the tumor sample (including but not limited to a primary tumor biopsy, circulating tumor cells and circulating tumor DNA) from the subject with the expression level of said gene in a control sample.

The determination of the c-MAF gene expression level, copy number, amplification or gain must be correlated with values of a control sample or reference sample. Depending on the type of tumor to be analyzed, the exact nature of the control sample may vary. Thus, in the event that a diagnosis is to be evaluated, then the reference sample is a tumor tissue sample from a subject with breast cancer that has not metastasized or that corresponds to the median value of the c-MAF gene expression levels measured in a tumor tissue collection in biopsy samples from subjects with breast cancer which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (c-MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least about 2, at least about 10, at least about 20, at least about 25, at least about 50, at least about 75, at least about 100, at least about 250, at least about 500, to more than 1000 subjects, classified according to the foregoing considerations, for example according to various age categories, are taken as the reference group. The sample collection from which the reference level is derived will preferably be formed by subjects suffering from the same type of cancer as the patient object of the study (e.g., breast cancer). Similarly, the reference value within a cohort of patients can be established using a receiving operating curve (ROC) and measuring the area under the curve for all de sensitivity and specificity pairs to determine which pair provides the best values and what the corresponding reference value is. ROC is a standard statistical concept. A description can be found in Stuart G. Baker "The Central Role of Receiver Operating Characteristic (ROC) curves in Evaluating Tests for the Early Detection of Cancer" *Journal of The National Cancer Institute* (2003) Vol 95, No. 7, 511-515.

Once this median or reference value has been established, the level of this marker expressed in tumor tissues from patients with this median value can be compared and thus be assigned, for example, to the "increased" expression level. Due to the variability among subjects (for example, aspects referring to age, race, etc.) it is very difficult (if not virtually impossible) to establish absolute reference values of c-MAF expression. Thus, in particular embodiments the reference values for "increased" or "reduced" expression of the c-MAF expression are determined by calculating the percentiles by conventional means which involves performing assays in one or several samples isolated from subjects whose disease is well documented by any of the methods mentioned above the c-MAF expression levels. The "reduced" levels of c-MAF can then preferably be assigned to samples wherein the c-MAF expression levels are equal to or lower than $50^{th}$ percentile in the normal population including, for example, expression levels equal to or lower than the $60^{th}$ percentile in the normal population, equal to or lower than the $70^{th}$ percentile in the normal population, equal to or lower than the $80^{th}$ percentile in the normal population, equal to or lower than the $90^{th}$ percentile in the normal population, and equal to or lower than the $95^{th}$ percentile in the normal population. The "increased" c-MAF gene expression levels can then preferably be assigned to samples wherein the c-MAF gene expression levels are equal to or greater than the $50^{th}$ percentile in the normal population including, for example, expression levels equal to or greater than the 60th percentile in the normal population, equal to or greater than the 70th percentile in the normal population, equal to or greater than the 80th percentile in the normal population, equal to or greater than the 90th percentile in the normal population, and equal to or greater than the 95th percentile in the normal population.

In a particular embodiment, the degree of amplification or gain of the c-MAF gene can be determined by means of determining the amplification or gain of a chromosome region containing said gene. Preferably, the chromosome region the amplification or gain of which is indicative of the existence of amplification or gain of the c-MAF gene is the locus 16q22-q24 which includes the c-MAF gene. The locus 16q22-q24 is located in chromosome 16, in the long arm of said chromosome and in a range between band 22 and band 24. This region corresponds in the NCBI database with the contigs NT_010498.15 and NT_010542.15. In another preferred embodiment, the degree of amplification or gain of the c-MAF gene can be determined by means of using a probe specific for said gene.

In some embodiments, the amplification or gain is in region at the 16q23 locus. In some embodiments, the amplification or gain is in any part of the chromosomal region between Chr. 16—79,392,959 bp to 79,663,806 bp (from centromere to telomere). In some embodiments, the amplification or gain is in the genomic region between Chr. 16—79,392,959 bp to 79,663,806 bp, but excluding DNA repeating elements. In some embodiments, amplification or gain is measured using a probe specific for that region.

In an embodiment, the c-MAF gene is amplified with respect to a reference gene copy number when the c-MAF gene copy number is higher than the copy number that a reference sample or control sample has. In one example, the c-MAF gene is said to be "amplified" if the genomic copy number or the average genomic copy number of the c-MAF gene is increased by at least about 2- (i.e., 6 copies), 3- (i.e., 8 copies), 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number or the average genomic copy number of the c-MAF gene per cell is at least about 2.1, 2.2, 2.3, 2.4, 2.5, 2.6, 2.7, 2.8, 2.9, 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In some embodiments, when copy number is measured, the control sample refers to a tumor sample of a subject with breast cancer who has not suffered metastasis or that correspond to the median value of the c-MAF gene copy number measured in a tumor tissue collection in biopsy samples of subjects with breast cancer who have not suffered metastasis. Said reference sample is typically obtained by combining equal amounts of samples from a subject population. If the c-MAF gene copy number is increased with respect to the copy number of said gene in the control sample, then subject has a positive diagnosis for metastasis or a greater tendency to develop metastasis. In another embodiment, the reference gene copy number is the gene copy number in a sample of breast cancer from a subject who has not suffered bone metastasis.

In another embodiment, the amplification or gain is determined by means of in situ hybridization or PCR.

In another embodiment and as described in the present invention, given that the chr16q22-24, including the c-MAF gene, is amplified in breast cancer cells is related to the presence of metastasis, relapse or recurrence the chr16q22-24, including the c-MAF gene, amplification or gain allow making decisions in terms of the most suitable therapy for the subject suffering said cancer.

The determination of the amplification of the c-MAF gene needs to be correlated with values of a control sample or reference sample that correspond to the level of amplification of the c-MAF gene measured in a tumor tissue sample of a subject with breast cancer who has not suffered metastasis or that correspond to the median value of the amplification of the c-MAF gene measured in a tumor tissue collection in biopsy samples of subjects with breast cancer who have not suffered metastasis. Said reference sample is typically obtained by combining equal amounts of samples from a subject population.

In general, the typical reference samples will be obtained from subjects who are clinically well documented and in whom the absence of metastasis is well characterized. The sample collection from which the reference level is derived will preferably be made up of subjects suffering the same type of cancer as the patient object of the study. Once this median value has been established, the level of amplification of c-MAF in tumor tissues of patients can be compared with this median value, and thus, if there is amplification, the subject has a positive diagnosis of metastasis or a greater tendency to develop metastasis.

In another aspect, the invention relates to an in vitro method for designing a customized therapy for a patient suffering from breast cancer, which comprises determining if the c-MAF gene is translocated in a sample of said subject.

In some embodiments, the translocated gene is from the region at the 16q23 locus. In some embodiments, the translocated gene is from any part of the chromosomal region between Chr. 16—79,392,959 bp to 79,663,806 bp (from centromere to telomere). In some embodiments, the translocated gene is from the genomic region between Chr. 16—79,392,959 bp to 79,663,806 bp, but excluding DNA repeating elements. In some embodiments, the translocation is measured using a probe specific for that region.

In a particular embodiment, the translocation of the c-MAF gene can be determined by means of determining the translocation of a chromosome region containing said gene. In one embodiment, the translocation is the t(14,16) translocation. In another embodiment, the chromosome region that is translocated is from locus 16q22-q24. The locus 16q22-q24 is located in chromosome 16, in the long arm of said chromosome and in a range between band 22 and band 24. This region corresponds in the NCBI database with the contigs NT_010498.15 and NT_010542.15. In an, the c-MAF gene translocates to chromosome 14 at the locus 14q32, resulting in the translocation t(14,16)(q32,q23). This translocation places the MAF gene next to the strong enhancers in the IgH locus, which, in some cases, leads to overexpression of MAF. (Eychène, A., Rocques, N., and Puoponnot, C., A new MAFia in cancer. 2008. *Nature Reviews: Cancer.* 8: 683-693.)

In an embodiment, the translocation of the c-MAF gene can be determined by means of using a probe specific for said translocation.

One embodiment of the invention comprises a method in which in a first step it is determined if the c-MAF gene is translocated in a sample of a subject. In an embodiment, the sample is a tumor tissue sample.

In a particular embodiment, a method of the invention for the prognosis of the tendency to develop bone metastasis in a subject with breast cancer comprises determining the c-MAF gene copy number in a sample of said subject wherein the c-MAF gene is translocated and comparing said copy number with the copy number of a control or reference sample, wherein if the c-MAF copy number is greater with respect to the c-MAF copy number of a control sample, then the subject has a greater tendency to develop bone metastasis.

In some embodiments, the amplification, gain and copy number of the c-MAF gene are determined after translocation of the c-MAF gene is determined. In some embodiments, a probe is used to determine if the cell is polyploid for the c-MAF gene. In some embodiments, a determination of polyploidy is made by determining if there are more than 2 signals from the gene of interest. In some embodiments, polyploidy is determined by measuring the signal from the probe specific for the gene of interest and comparing it with a centromeric probe or other probe.

Method of Predicting Survival, Including IDFS, Using c-MAF

The present invention is directed to predicting the IDFS of a subject suffering from breast cancer. In certain embodiments, the subjects have a high expression level, copy number, amplification, or gain of c-MAF. In other embodiments, the subjects have a low expression level, copy number, amplification, or gain of c-MAF. In some embodiments, the cancer is triple-negative breast cancer. In other embodiments, the cancer is ER+ breast cancer. In further embodiments, the cancer is ER− breast cancer. In certain embodiments, the cancer is basal-like breast cancer. In still further embodiments, the cancer is HER2+ breast cancer. In some embodiments, the subjects are post-menopausal. In other embodiments, the subjects are non-post menopausal.

In some embodiments, the invention is directed to an in vitro method for predicting the IDFS of a patient with breast cancer which comprises i) quantifying the expression level, copy number, amplification, or gain of the c-MAF gene in a sample of said subject and ii) comparing the expression level, copy number, amplification, or gain obtained in step i) with a reference value, wherein increased expression level, copy number, amplification, or gain of said gene with respect to said reference value is indicative of a poor IDFS prognosis.

In an embodiment, the invention is directed to an in vitro method for predicting the IDFS of a patient with breast cancer which comprises determining the c-MAF gene expression level, copy number, amplification, or gain in a sample of said subject relative to a reference wherein an increase of the c-MAF gene expression level, copy number, amplification, or gain with respect to said reference is indicative of a poor IDFS prognosis.

In a further embodiment, the invention is directed to an in vitro method for predicting the IDFS, excluding bone recurrence, of a patient with breast cancer which comprises determining the c-MAF gene expression level, copy number, amplification, or gain in a sample of said subject relative to a reference wherein an increase of the c-MAF gene expression level, copy number, amplification, or gain with respect to said reference is indicative of a poor IDFS prognosis, excluding bone recurrence.

In some embodiments, the copy number of MAF or average copy number of MAF per cell as measured using FISH≥2.1, 2.2, 2.3, 2.4, 2.5, 2.6, 2.7, 2.8, 2.9 or 3.0 is considered a high value. In certain embodiments, the MAF FISH value is ≥2.2. In other embodiments, the MAF FISH value is ≥2.3. In further embodiments, the MAF FISH value is ≥2.4. In still further embodiments, the MAF FISH value is ≥2.5.

In some embodiments, the c-MAF status of the subject predicts the overall survival or the duration of the disease-free survival of the subject. In certain embodiments, the c-MAF status in any of the embodiments herein includes 16q23 or 16q22-24 chromosomal locus amplification, copy gain or translocation or lack thereof, or 16q23 or 16q22-24 chromosomal locus deletions. In particular embodiments, a subject with an increase in their c-MAF gene expression level, copy number, amplification, or gain with respect to a reference has a shorter disease free survival than a subject without an increase of the c-MAF gene expression level, copy number, amplification, or gain with respect to a reference. In embodiments, the disease free survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less than the disease free survival of a subject without an increase of the c-MAF gene expression level, copy number, amplification, or gain with respect to a reference. In certain embodiments, a subject with an increase in their c-MAF gene expression level, copy number, amplification, or gain with respect to a reference has a shorter overall survival than a subject without an increase of the c-MAF gene expression level, copy number, amplification, or gain with respect to a reference. In embodiments, the overall survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less than the disease free survival of a subject without an increase of the c-MAF gene expression level, copy number, amplification, or gain with respect to a reference. In embodiments, the subject is post menopausal. In other embodiments, the subject is non-post-menopausal. In some embodiments, the subject is premenopausal.

In embodiments, the disease free survival of a subject without an increase of the c-MAF gene expression level, copy number, amplification, or gain with respect to a reference is longer after treatment with a bone modifying agent and/or an agent that avoids or prevents bone degradation, i.e. zoledronic acid, than the disease free survival of a subject with an increase in their c-MAF gene expression level, copy number, amplification, or gain with respect to a reference. In embodiments, the disease free survival of a subject without an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more after treatment with zoledronic acid than the disease free survival of a subject with an increase of the c-MAF gene expression level, copy number, amplification, or gain with respect to a reference after treatment with a bone modifying agent and/or an agent that avoids or prevents bone degradation, i.e. zoledronic acid. In embodiments, the overall survival of a subject without an increase of the c-MAF gene expression level, copy number, amplification, or gain with respect to a reference is longer after treatment a bone modifying agent and/or an agent that avoids or prevents bone degradation, i.e. zoledronic acid, than the overall survival of a subject with an increase in their c-MAF gene expression level, copy number, amplification, or gain with respect to a reference. In embodiments, the overall survival of a subject without an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more after treatment with zoledronic acid than the overall survival of a subject with an increase of the c-MAF gene expression level, copy number, amplification, or gain with respect to a reference after treatment with zoledronic acid. In embodiments, the subject is post menopausal. In other embodiments, the subject is non-post-menopausal. In some embodiments, the subject is premenopausal.

In embodiments, the disease free survival of a subject with an increase of the c-MAF gene expression level, copy number, amplification, or gain with respect to a reference is shorter after treatment a bone modifying agent and/or an agent that avoids or prevents bone degradation, i.e. zoledronic acid, than the disease free survival of a subject without an increase in their c-MAF gene expression level, copy number, amplification, or gain with respect to a reference. In embodiments, the disease free survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less after treatment a bone modifying agent and/or an agent that avoids or prevents bone degradation, i.e. zoledronic acid, than the disease free survival of a subject without an increase of the c-MAF gene expression level, copy number, amplification, or gain with respect to a reference after treatment a bone modifying agent and/or an agent that avoids or prevents bone degradation, i.e. zoledronic acid. In embodiments, the overall survival of a subject with an increase of the c-MAF gene expression level, copy number, amplification, or gain with respect to a reference is shorter after treatment a bone modifying agent and/or an agent that avoids or prevents bone degradation, i.e. zoledronic acid, than the overall survival of a subject without an increase in their c-MAF gene expression level, copy number, amplification, or gain with respect to a reference. In embodiments, the overall survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less after treatment a bone modifying agent and/or an agent that avoids or prevents bone degradation, i.e. zoledronic acid, than the overall survival of a subject without an increase of the c-MAF gene expression level, copy number, amplification, or gain with respect to a reference after treatment a bone modifying agent and/or an agent that avoids or prevents bone degradation, i.e. zoledronic acid. In embodiments, the subject is post menopausal. In other embodiments, the subject is non-post-menopausal. In some embodiments, the subject is premenopausal.

In embodiments, the disease free survival of non-post menopausal subject with an increase of the c-MAF gene expression level, copy number, amplification, or gain with respect to a reference is shorter after treatment a bone modifying agent and/or an agent that avoids or prevents bone degradation, i.e. zoledronic acid, than the disease free survival of a subject without an increase in their c-MAF gene expression level, copy number, amplification, or gain with respect to a reference. In embodiments, the disease free survival of a non-post menopausal subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less after treatment a bone modifying agent and/or an agent that avoids or prevents bone degradation, i.e. zoledronic acid, than the disease free survival of a subject without an increase of the c-MAF gene expression level, copy number, amplification, or gain with respect to a reference after treatment a bone modifying agent and/or an agent that avoids or prevents bone degradation, i.e. zoledronic acid.

In embodiments, the overall survival of a subject with an increase of the c-MAF gene expression level, copy number, amplification, or gain with respect to a reference is shorter after treatment a bone modifying agent and/or an agent that avoids or prevents bone degradation, i.e. zoledronic acid, than the disease free survival of a subject without an increase in their c-MAF gene expression level, copy number, amplification, or gain with respect to a reference. In embodiments, the overall survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more less after treatment a bone modifying agent and/or an agent that avoids or prevents bone degradation, i.e. zoledronic acid, than the overall survival of a subject without an increase of the c-MAF gene expression level, copy number, amplification, or gain with respect to a reference after treatment a bone modifying agent and/or an agent that avoids or prevents bone degradation, i.e. zoledronic acid. In embodiments, the subject is post menopausal. In other embodiments, the subject is non-post-menopausal. In some embodiments, the subject is premenopausal.

In embodiments, the predictive power of MAF for the OS or DFS of a subject is based on the menopausal status of the subject. In some embodiments, MAF is predictive in postmenopausal, unknown and perimenopausal subjects at risk of a shorter DFS or worst OS. In other embodiments, in premenopausal subjects, MAF positive subjects are those at less risk and are more likely to have a longer DFS and better OS.

In embodiments, the MAF status of the subject is predictive of the treatments that should be received by the subject. In embodiments, the c-MAF status in any of the embodiments herein includes 16q23 or 16q22-24 chromosomal locus amplification, copy gain or translocation or lack thereof, or 16q23 or 16q22-24 chromosomal locus deletions. In embodiments, post-menopausal patients with an increase of the c-MAF gene expression level, copy number, amplification, or gain with respect to a reference (and are therefore at a high risk of a bad DFS or OS outcome) may be administered any treatment disclosed herein. In some embodiments, post menopausal patients with an increase of the c-MAF gene expression level, copy number, amplification, or gain with respect to a reference (and are therefore at a high risk of a bad DFS or OS outcome) may be treated by extending their hormonal treatment beyond the five year time prescribed by the use of hormonal treatments as the standard of care. In certain embodiments, the hormonal treatment is Tamoxifen and/or aromatase inhibitors. Patients without an increase of the c-MAF gene expression level, copy number, amplification, or gain with respect to a reference should not be administered a treatment disclosed herein.

In a particular embodiment, the subject has metastasis or a prognosis to undergo metastasis. In some embodiments, the metastasis is a bone metastasis. In a further embodiment, the bone metastasis is osteolytic metastasis.

In some embodiments, the sample is a primary tumor tissue sample of the subject. In a second step, the c-MAF gene expression level, copy number, amplification or gain obtained in the tumor sample of the subject is compared with the expression level, copy number, amplification or gain of said gene in a control sample. The determination of the c-MAF gene expression levels, copy number, amplification or gain must be related to values of a control sample or reference sample. Depending on the type of tumor to be analyzed, the exact nature of the control sample may vary. Thus, in some embodiments, the reference sample is a tumor tissue sample of a subject with breast cancer that has not metastasized, relapsed or reoccurred or that corresponds to the median value of the c-MAF gene expression levels, copy number, amplification or gain measured in a tumor tissue collection in biopsy samples of subjects with breast cancer which has not metastasized, relapsed or reoccurred.

In one embodiment, the methods of the invention comprise in a second step comparing the c-MAF gene expression level, copy number, amplification or gain obtained in the tumor sample (including but not limited to a primary tumor biopsy, circulating tumor cells and circulating tumor DNA) from the subject with the expression level of said gene in a control sample.

Once the c-MAF gene expression level, copy number, amplification or gain in a tumor tissue sample, a circulating tumor cell or circulating tumor DNA from a subject with breast cancer has been measured and compared with the control sample, if the expression level of said gene is increased with respect to its expression level in the control sample, then it can be concluded that said subject has a positive diagnosis for metastasis or a greater tendency to develop metastasis.

The determination of the c-MAF gene expression level, copy number, amplification or gain must be correlated with values of a control sample or reference sample. Depending on the type of tumor to be analyzed, the exact nature of the control sample may vary. Thus, in the event that a diagnosis is to be evaluated, then the reference sample is a tumor tissue sample from a subject with breast cancer that has not metastasized or that corresponds to the median value of the c-MAF gene expression levels measured in a tumor tissue collection in biopsy samples from subjects with breast cancer which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (c-MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least about 2, at least about 10, at least about 20, at least about 25, at least about 50, at least about 75, at least about 100, at least about 250, at least about 500, to more than 1000 subjects, classified according to the foregoing considerations, for example according to various age categories, are taken as the reference group. The sample collection from which the reference level is derived will preferably be formed by subjects suffering from the same type of cancer as the patient object of the study (e.g., breast cancer). Similarly, the reference value within a cohort of patients can be established using a receiving operating curve (ROC) and measuring the area under the curve for all de sensitivity and specificity pairs to determine which pair provides the best values and what the corresponding reference value is. ROC is a standard statistical concept. A description can be found in Stuart G. Baker "The Central Role of Receiver Operating Characteristic (ROC) curves in Evaluating Tests for the Early Detection of Cancer" *Journal of The National Cancer Institute* (2003) Vol 95, No. 7, 511-515.

Once this median or reference value has been established, the level of this marker expressed in tumor tissues from patients with this median value can be compared and thus be assigned, for example, to the "increased" expression level. Due to the variability among subjects (for example, aspects referring to age, race, etc.) it is very difficult (if not virtually impossible) to establish absolute reference values of c-MAF expression. Thus, in particular embodiments the reference values for "increased" or "reduced" expression of the c-MAF expression are determined by calculating the percentiles by conventional means which involves performing assays in one or several samples isolated from subjects whose disease is well documented by any of the methods mentioned above the c-MAF expression levels. The "reduced" levels of c-MAF can then preferably be assigned to samples wherein the c-MAF expression levels are equal to or lower than $50^{th}$ percentile in the normal population including, for example, expression levels equal to or lower than the $60^{th}$ percentile in the normal population, equal to or lower than the $70^{th}$ percentile in the normal population, equal to or lower than the $80^{th}$ percentile in the normal population, equal to or lower than the $90^{th}$ percentile in the normal population, and equal to or lower than the $95^{th}$ percentile in the normal population. The "increased" c-MAF gene expression levels can then preferably be assigned to samples wherein the c-MAF gene expression levels are equal to or greater than the $50^{th}$ percentile in the normal population including, for example, expression levels equal to or greater than the $60^{th}$ percentile in the normal population, equal to or greater than the $70^{th}$ percentile in the normal population, equal to or greater than the $80^{th}$ percentile in the normal population, equal to or greater than the $90^{th}$ percentile in the normal population, and equal to or greater than the $95^{th}$ percentile in the normal population.

In a particular embodiment, the degree of amplification or gain of the c-MAF gene can be determined by means of determining the amplification or gain of a chromosome region containing said gene. Preferably, the chromosome region the amplification or gain of which is indicative of the existence of amplification or gain of the c-MAF gene is the locus 16q22-q24 which includes the c-MAF gene. The locus 16q22-q24 is located in chromosome 16, in the long arm of said chromosome and in a range between band 22 and band 24. This region corresponds in the NCBI database with the contigs NT_010498.15 and NT_010542.15. In an embodiment, the degree of amplification or gain of the c-MAF gene can be determined by means of using a probe specific for said gene.

When copy number is measured, the control sample refers to a tumor sample of a subject with breast cancer who has not suffered metastasis or that correspond to the median value of the c-MAF gene copy number measured in a tumor tissue collection in biopsy samples of subjects with breast cancer who have not suffered metastasis. Said reference sample is typically obtained by combining equal amounts of samples from a subject population. If the c-MAF gene copy number is increased with respect to the copy number of said gene in the control sample, then subject has a positive diagnosis for metastasis or a greater tendency to develop metastasis. In embodiments, the copy number is determined as the average copy number per cell.

In some embodiments, the amplification or gain is in region at the 16q23 locus. In some embodiments, the amplification or gain is in any part of the chromosomal region between Chr. 16—79,392,959 bp to 79,663,806 bp (from centromere to telomere). In some embodiments, the amplification or gain is in the genomic region between Chr. 16—79,392,959 bp to 79,663,806 bp, but excluding DNA repeating elements. In some embodiments, amplification or gain is measured using a probe specific for that region.

In an embodiment, the c-MAF gene is amplified with respect to a reference gene copy number when the c-MAF gene copy number is higher than the copy number that a reference sample or control sample has. In one example, the c-MAF gene is said to be "amplified" if the genomic copy number or the average genomic copy number of the c-MAF gene is increased by at least about 2-, 3-, 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number or the average genomic copy number of the c-MAF gene per cell is at least about 2.1, 2.2, 2.3, 2.4, 2.5, 2.6, 2.7, 2.8, 2.9, 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In another embodiment, the reference gene copy number is the gene copy number in a sample of breast cancer from a subject who has not suffered bone metastasis.

In another embodiment, the amplification or gain is determined by means of in situ hybridization or PCR.

In another embodiment and as described in the present invention, given that the chr16q22-24, including the c-MAF gene, is amplified in breast cancer cells is related to the presence of metastasis, relapse or recurrence the chr16q22-24, including the c-MAF gene, amplification or gain allow making decisions in terms of the most suitable therapy for the subject suffering said cancer.

The determination of the amplification of the c-MAF gene needs to be correlated with values of a control sample or reference sample that correspond to the level of amplification of the c-MAF gene measured in a tumor tissue sample of a subject with breast cancer who has not suffered metastasis or that correspond to the median value of the amplification of the c-MAF gene measured in a tumor tissue collection in biopsy samples of subjects with breast cancer who have not suffered metastasis. Said reference sample is typically obtained by combining equal amounts of samples from a subject population.

In general, the typical reference samples will be obtained from subjects who are clinically well documented and in whom the absence of metastasis is well characterized. The sample collection from which the reference level is derived will preferably be made up of subjects suffering the same type of cancer as the patient object of the study. Once this median value has been established, the level of amplification of c-MAF in tumor tissues of patients can be compared with this median value, and thus, if there is amplification, the subject has a positive diagnosis of metastasis or a greater tendency to develop metastasis.

In another aspect, the invention relates to determining if the c-MAF gene is translocated in a sample of said subject.

In some embodiments, the translocated gene is from the region at the 16q23 locus. In some embodiments, the translocated gene is from any part of the chromosomal region between Chr. 16—79,392,959 bp to 79,663,806 bp (from centromere to telomere). In some embodiments, the translocated gene is from the genomic region between Chr. 16—79,392,959 bp to 79,663,806 bp, but excluding DNA repeating elements. In some embodiments, the translocation is measured using a probe specific for that region.

In a particular embodiment, the translocation of the c-MAF gene can be determined by means of determining the translocation of a chromosome region containing said gene. In one embodiment, the translocation is the t(14,16) translocation. In another embodiment, the chromosome region that is translocated is from locus 16q22-q24. The locus 16q22-q24 is located in chromosome 16, in the long arm of said chromosome and in a range between band 22 and band 24. This region corresponds in the NCBI database with the contigs NT_010498.15 and NT_010542.15. In an embodiment, the c-MAF gene translocates to chromosome 14 at the locus 14q32, resulting in the translocation t(14,16)(q32, q23). This translocation places the MAF gene next to the strong enhancers in the IgH locus, which, in some cases, leads to overexpression of MAF. (Eychène, A., Rocques, N., and Puoponnot, C., A new MAFia in cancer. 2008. *Nature Reviews: Cancer.* 8: 683-693.)

In an embodiment, the translocation of the c-MAF gene can be determined by means of using a probe specific for said translocation.

One embodiment of the invention comprises a method in which in a first step it is determined if the c-MAF gene is translocated in a sample of a subject. In an embodiment, the sample is a tumor tissue sample.

In a particular embodiment, a method of the invention for the prognosis of the tendency to develop bone metastasis in a subject with breast cancer comprises determining the c-MAF gene copy number in a sample of said subject wherein the c-MAF gene is translocated and comparing said copy number with the copy number of a control or reference sample, wherein if the c-MAF copy number is greater with respect to the c-MAF copy number of a control sample, then the subject has a greater tendency to develop bone metastasis.

Methods for determining whether the c-MAF gene or the chromosome region 16q22-q24 is translocated are widely known in the state of the art and include those described previously for the amplification of c-MAF. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, the gain, the copy number, or the translocation can be determined by counting the number of fluorescent points, colored points or points with silver in the chromosomes or in the nucleus. In other embodiments, the detection of copy number alterations and translocations can be detected through the use of whole genome sequencing, exome sequencing or by the use of any PCR derived technology. For instance, PCR can be performed on samples of genomic DNA to detect translocation. In one embodiment, quantitative PCR is used. In one embodiment, PCR is performed with a primer specific to the c-MAF gene and a primer specific to the IGH promoter region; if a product is produced, translocation has occurred.

In some embodiments, the amplification, gain and copy number of the c-MAF gene are determined after translocation of the c-MAF gene is determined. In some embodiments, a probe is used to determine if the cell is polyploid for the c-MAF gene. In some embodiments, a determination of polyploidy is made by determining if there are more than 2 signals from the gene of interest. In some embodiments, polyploidy is determined by measuring the signal from the probe specific for the gene of interest and comparing it with a centromeric probe or other probe.

Methods of Measuring c-MAF Expression, Copy Number, Amplification, Gain and Translocation In some embodiments, the c-MAF gene expression level, copy number, amplification, gain or translocation is measured using any method known in the art or described herein.

The c-MAF protein expression level can be quantified by any conventional method that allows detecting and quantifying said protein in a sample from a subject. By way of non-limiting illustration, said protein levels can be quantified, for example, by using antibodies with c-MAF binding capacity (or a fragment thereof containing an antigenic determinant) and the subsequent quantification of the complexes formed. The antibodies used in these assays may or may not be labeled. Illustrative examples of markers that can be used include radioactive isotopes, enzymes, fluorophores, chemiluminescence reagents, enzyme substrates or cofactors, enzyme inhibitors, particles, dyes, etc. There is a wide range of known assays that can be used in the present invention which use unlabeled antibodies (primary antibody) and labeled antibodies (secondary antibody); these techniques include Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies or assays based on colloidal precipitation in formats such as dipsticks. Other ways for detecting and quantifying said c-MAF protein include affinity chromatography techniques, ligand binding assays, etc. When an immunological method is used, any antibody or reagent that is known to bind to the c-MAF protein with a high affinity can be used for detecting the amount thereof. This would include, but is not limited to, the use of an antibody, for example, polyclonal sera, supernatants of hybridomas or monoclonal antibodies, antibody fragments, Fv, Fab, Fab' and F(ab')2, scFv, humanized diabodies, triabodies, tetrabodies, antibodies, nanobodies, alphabodies, stapled peptides, and cyclopeptides. There are commercial anti-c-MAF protein antibodies on the market which can be used in the context of the present invention, such as for example antibodies ab427, ab55502, ab55502, ab72584, ab76817, ab77071 (Abcam plc, 330 Science Park, Cambridge CB4 0FL, United Kingdom), the 075444 monoclonal antibody (Mouse Anti-Human MAF Azide free Monoclonal antibody, Unconjugated, Clone 6b8) of AbD Serotec, etc. There are many commercial companies offering anti-c-MAF antibodies, such as Abnova Corporation, Bethyl Laboratories, Bioworld Technology, GeneTex, etc.

In some embodiments, the c-MAF protein levels are detected by an antigen binding member or fragment thereof.

In some embodiments, the binding member is an antigen binding molecule or fragment thereof that binds to human c-MAF, wherein the antibody binding molecule or fragment thereof comprises a heavy chain CDR1 at least about 70%, about 75%, about 80%, about 85%, about 90%, about 95%, about 99% or about 100% identical to the amino acid sequence of SEQ ID NO: 21, and/or a heavy chain CDR2 at least about 70%, about 75%, about 80%, about 85%, about 90%, about 95%, about 99% or about 100% identical to the amino acid sequence of SEQ ID NO: 22, and/or a heavy chain CDR3 at least about 70%, about 75%, about 80%, about 85%, about 90%, about 95%, about 99% or about 100% identical to the amino acid sequence of SEQ ID NO: 23; and/or comprising a light chain CDR1 at least about 70%, about 75%, about 80%, about 85%, about 90%, about 95%, about 99% or about 100% identical to the amino acid sequence of SEQ ID NO: 18, and/or a light chain CDR2 at least about 70%, about 75%, about 80%, about 85%, about 90%, about 95%, about 99% or about 100% identical to the amino acid sequence of SEQ ID NO: 19 and/or a light chain CDR3 at least about 70%, about 75%, about 80%, about 85%, about 90%, about 95%, about 99% or about 100% identical to the amino acid sequence of SEQ ID NO: 20.

In some embodiments, the antibody or fragment thereof comprises a VH domain with a sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 15.

In some embodiments, the antigen binding molecule or fragment thereof comprises a VL domain with a sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 17.

In some embodiments, the antibody or fragment thereof comprises a heavy chain sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 14.

In some embodiments, the antibody or fragment thereof comprises a light chain sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 16.

In some embodiments, the antigen binding molecule or fragment thereof is an antibody. In some embodiments, the antibody is a rabbit antibody, a mouse antibody, a chimeric antibody or a humanized antibody. In one aspect, the present invention is directed to a binding member, functional fragment, antibody or variant thereof that specifically binds to the epitope encoded by SEQ ID NO: 24. In some embodiments, the antibody is any antibody described in Int'l. Appl. No. PCT/IB2015/059562, which is incorporated herein by reference in its entirety.

In a particular embodiment, the c-MAF protein levels are quantified means of western blot, immunohistochemistry, ELISA or a protein array.

As understood by the person skilled in the art, the gene expression levels can be quantified by measuring the messenger RNA levels of said gene or of the protein encoded by said gene. In some embodiment, the gene expression level can be quantified by any means known in the art.

For this purpose, the biological sample can be treated to physically or mechanically break up the tissue or cell structure, releasing the intracellular components into an aqueous or organic solution for preparing nucleic acids. The nucleic acids are extracted by means of commercially available methods known by the person skilled in the art (Sambroock, J., et al., "Molecular cloning: a Laboratory Manual", 3rd ed., Cold Spring Harbor Laboratory Press, N.Y., Vol. 1-3.)

Thus, the c-MAF gene expression level can be quantified from the RNA resulting from the transcription of said gene (messenger RNA or mRNA) or, alternatively, from the complementary DNA (cDNA) of said gene. Therefore, in a particular embodiment of the invention, the quantification of the c-MAF gene expression levels comprises the quantification of the messenger RNA of the c-MAF gene or a fragment of said mRNA, complementary DNA of the c-MAF gene or a fragment of said cDNA or the mixture thereof.

Virtually any conventional method can be used within the scope of the invention for detecting and quantifying the mRNA levels encoded by the c-MAF gene or of the corresponding cDNA thereof. By way of non-limiting illustration, the mRNA levels encoded by said gene can be quantified using conventional methods, for example, methods comprising mRNA amplification and the quantification of said mRNA amplification product, such as electrophoresis and staining, or alternatively, by Southern blot and using suitable probes, Northern blot and using specific probes of the mRNA of the gene of interest (c-MAF) or of the corresponding cDNA thereof, mapping with 51 nuclease, RT-PCR, hybridization, microarrays, etc., preferably by means of real time quantitative PCR using a suitable marker. Likewise, the cDNA levels corresponding to the mRNA encoded by the c-MAF gene can also be quantified by means of using conventional techniques; in this case, the method of the invention includes a step for synthesizing the corresponding cDNA by means of reverse transcription (RT) of the corresponding mRNA followed by the amplification and quantification of said cDNA amplification product. Conventional methods for quantifying expression levels can be found, for example, in Sambrook et al., 2001. (cited ad supra). These methods are known in the art and a person skilled in the art would be familiar with the normalizations necessary for each technique. For example, the expression measurements generated using multiplex PCR should be normalized by comparing the expression of the genes being measured to so called "housekeeping" genes, the expression of which should be constant over all samples, thus providing a baseline expression to compare against or other control genes whose expression are known to be modulated with cancer.

In a particular embodiment, the c-MAF gene expression levels are quantified by means of quantitative polymerase chain reaction (PCR) or a DNA, RNA array, or nucleotide hybridization technique.

In addition, the c-MAF gene expression level can also be quantified by means of quantifying the expression levels of the protein encoded by said gene, i.e., the c-MAF protein (c-MAF) [NCBI, accession number O75444], or any functionally equivalent variant of the c-MAF protein. There are two c-MAF protein isoforms, the α isoform (NCBI, NP_005351.2) made up of 403 amino acids (SEQ ID NO: 4) and the β isoform (NP_001026974.1) made up of 373 amino acids (SEQ ID NO: 5). The c-MAF gene expression level can be quantified by means of quantifying the expression levels of any of the c-MAF protein isoforms. Thus, in a particular embodiment, the quantification of the levels of the protein encoded by the c-MAF gene comprises the quantification of the c-MAF protein.

Methods for determining whether the c-MAF gene or the chromosome region 16q22-q24 is amplified are widely known in the state of the art. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, gain or the copy number can be determined by counting the number of fluorescent points, colored points or points with silver in the chromosomes or in the nucleus.

The fluorescence in situ hybridization (FISH) is a cytogenetic technique which is used for detecting and locating the presence or absence of specific DNA sequences in chromosomes. FISH uses fluorescence probes which only bind to some parts of the chromosome with which they show a high degree of sequence similarity. In a typical FISH method, the DNA probe is labeled with a fluorescent molecule or a hapten, typically in the form of fluor-dUTP, digoxigenin-dUTP, biotin-dUTP or hapten-dUTP which is incorporated in the DNA using enzymatic reactions, such as nick translation or PCR. The sample containing the genetic material (the chromosomes) is placed on glass slides and is denatured by a formamide treatment. The labeled probe is then hybridized with the sample containing the genetic material under suitable conditions which will be determined by the person skilled in the art. After the hybridization, the sample is viewed either directly (in the case of a probe labeled with fluorine) or indirectly (using fluorescently labeled antibodies to detect the hapten).

In the case of CISH, the probe is labeled with digoxigenin, biotin or fluorescein and is hybridized with the sample containing the genetic material in suitable conditions.

Methods for determining whether the c-MAF gene or the chromosome region 16q22-q24 is translocated are widely known in the state of the art and include those described previously for the amplification of c-MAF. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, the gain, the copy number, or the translocation can be determined by counting the number of fluorescent points, colored points or points with silver in the chromosomes or in the nucleus. In other embodiments, the detection of copy number alterations and translocations can be detected through the use of whole genome sequencing, exome sequencing or by the use of any PCR derived technology. For instance, PCR can be performed on samples of genomic DNA to detect translocation. In one embodiment, quantitative PCR is used. In one embodiment, PCR is performed with a primer specific to the c-MAF gene and a primer specific to the IGH promoter region; if a product is produced, translocation has occurred.

Any marking or labeling molecule which can bind to a DNA can be used to label the probes used in the methods of the invention, thus allowing the detection of nucleic acid molecules. Examples of labels for the labeling include, although not limited to, radioactive isotopes, enzyme substrates, cofactors, ligands, chemiluminescence agents, fluorophores, haptens, enzymes and combinations thereof. Methods for labeling and guideline for selecting suitable labels for different purposes can be found, for example, in Sambrook et al. (Molecular Cloning: A Laboratory Manual, Cold Spring Harbor, N.Y., 1989) and Ausubel et al. (In Current Protocols in Molecular Biology, John Wiley and Sons, New York, 1998).

In some embodiments, a probe of the invention is a dual color probe. In some embodiments, a probe of the invention is a dual fusion probe. In some embodiments, a probe of the invention is a dual color, dual fusion probe. In some embodiments, two separate probes are used.

In another embodiment, one of the following probes is used to measure the c-MAF gene (including translation of the c-MAF gene): the Vysis LSI IGH/MAF Dual Color dual fusion probe, which comprises a probe against 14q32 and 16q23; a Kreatech diagnostics MAF/IGH gt(14;16) Fusion probe, an Abnova MAF FISH probe, a Cancer Genetics Italia IGH/MAF Two Color, Two Fusion translocation probe, a Creative Bioarray IGH/MAF-t(14;16)(q32;q23) FISH probe, a Amp Laboratories multiple myeloma panel by FISH, an Agilent probe specific to 16q23 or 14q32, a Dako probe specific to 16q23 or 14q32, a Cytocell IGH/MAF Translocation, Dual Fusion Probe, a Metasystems XL IGH/MAF Translocation—Dual Fusion Probe, a Zeiss FISH Probes XL, 100 µl, IGH/MAFB or a Genycell Biotech IGH/MAF Dual Fusion Probe.

In some embodiments, the label on the probe is a fluorophore. In some embodiments, the fluorophore on the probe is orange. In some embodiments, the fluorophore on the probe is green. In some embodiments, the fluorophore on the probe is red. In some cases, the fluorophore on the probe is yellow. In some embodiments, one probe is labeled with a red fluorophore, and one with a green fluorophore. In some embodiments, one probe is labeled with a green fluorophore and one with an orange fluorophore. In some cases, the fluorophore on the probe is yellow. For instance, if the MAF-specific probe is labeled with a red fluorophore, and the IGH-specific probe is labeled with a green fluorophore, if white is seen it indicates that the signals overlap and translocation has occurred.

In some embodiments, the fluorophore is SpectrumOrange. In some embodiments, the fluorophore is SpectrumGreen. In some embodiments, the fluorophore is DAPI. In some embodiments, the fluorophore is PlatinumBright405 In some embodiments, the fluorophore is PlatinumBright415. In some embodiments, the fluorophore is PlatinumBright495. In some embodiments, the fluorophore is PlatinumBright505. In some embodiments, the fluorophore is PlatinumBright550. In some embodiments, the fluorophore is PlatinumBright547. In some embodiments, the fluorophore is PlatinumBright570. In some embodiments, the fluorophore is PlatinumBright590. In some embodiments, the fluorophore is PlatinumBright647. In some embodiments, the fluorophore is PlatinumBright495/550. In some embodiments, the fluorophore is PlatinumBright415/495/550. In some embodiments, the fluorophore is DAPI/PlatinumBright495/550. In some embodiments, the fluorophore is FITC. In some embodiments, the fluorophore is Texas Red. In some embodiments, the fluorophore is DEAC. In some embodiments, the fluorophore is R6G. In some embodiments, the fluorophore is Cy5. In some embodiments, the fluorophore is FITC, Texas Red and DAPI. In some embodiments, a DAPI counterstain is used to visualize the translocation, amplification, gain or copy number alteration.

Agents and Therapies for Use in Methods for Treatment or Prevention of Breast Cancer In some embodiments, the methods of the invention herein include treating subjects with agents for avoiding or preventing bone remodelling. As used herein, an "agent for avoiding or preventing bone remodelling" refers to any molecule capable of treating or stopping bone degradation either by stimulating the osteoblast proliferation or inhibiting the osteoclast proliferation, including agents for avoiding or preventing bone degradation. In embodiments, the agent for avoiding or preventing bone remodeling is a bone modifying agent and/or an agent that avoids or prevents bone degradation. Illustrative examples of agents used for avoiding and/or preventing bone degradation include, although not limited to:

Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts and increasing their activity.

Strontium ranelate: is an alternative oral treatment, and forms part of the group of drugs called "dual action bone agents" (DABAs) because they stimulate the osteoblast proliferation and inhibit the osteoclast proliferation.

"Estrogen receptor modulators" (SERM) refers to compounds which interfere or inhibit the binding of estrogens to the receptor, regardless of the mechanism. Examples of estrogen receptor modulators include, among others, estrogens progestagen, estradiol, droloxifene, raloxifene, lasofoxifene, TSE-424, tamoxifen, idoxifene, LY353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4' dihydroxybenzophenone-2,4-dinitrophenyl-hydrazone and SH646.

Calcitonin: directly inhibits the osteoclast activity through the calcitonin receptor. The calcitonin receptors have been identified on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia, associated to breast cancer. Examples of bisphosphonates which can be used in the therapy designed by means of the fifth method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals.

"DKK-1 (Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., American Association for Cancer Research Annual Meeting. Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (i.e., blastic lesions) or destruction (i.e., lytic lesion. Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl)piperidin-1-yl]carbonylaminopyridin-4-yl}oxy)phenyl]-N'-(4-fluorophenyl)cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refer to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al. (Nature, 1975, 256: 495). Antibodies suitable in the context of the present invention include intact antibodies which comprise a variable antigen binding region and a constant region, fragments "Fab", "F(ab')2" and "Fab'", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harboring the full antigen-binding capacity of the original heavy-chain antibody. These newly discovered VHH domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor an antibody, antibody fragment, or fusion construct that binds the same epitope as Denosumab.

In an embodiment, the anti-RANKL nanobody is any of the nanobodies as described in WO2008142164, (the contents of which are incorporated in the present application by reference). In an embodiment, the anti-RANKL antibody is the ALX-0141 (Ablynx). ALX-0141 has been designed to inhibit bone loss associated with post-menopausal osteoporosis, rheumatoid arthritis, cancer and certain medications, and to restore the balance of healthy bone metabolism.

In an embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223, calcitonin, and a cathepsin K inhibitor. In an embodiment the agent preventing the bone degradation is a bisphosphonate. In an embodiment, the bisphosphonate is zoledronic acid.

In one embodiment, a CCR5 antagonist is administered to prevent or inhibit metastasis of the primary breast cancer tumor to bone or relapse or recurrence. In one embodiment, the CCR5 antagonist is a large molecule. In another embodiment, the CCR5 antagonist is a small molecule. In some embodiments, the CCR5 antagonist is Maraviroc. In some embodiments, the CCR5 antagonist is Vicriviroc. In some aspects, the CCR5 antagonist is Aplaviroc. In some aspects, the CCR5 antagonist is a spiropiperidine CCR5 antagonist. (Rotstein D. M. et al. 2009. Spiropiperidine CCR5 antagonists. Bioorganic & Medicinal Chemistry Letters. 19 (18): 5401-5406. In some embodiments, the CCR5 antagonist is INCB009471 (Kuritzkes, D. R. 2009. HIV-1 entry inhibitors: an overview. Curr. Opin. HIV AIDS. 4(2): 82-7).

In an embodiment the dual MET and VEGFR2 inhibitor is selected from the group consisting of Cabozantinib, Foretinib and E7050.

In embodiments, the MAF status is predictive of the treatments that should be received by the subject. In embodiments, the c-MAF status in any of the embodiments herein includes 16q23 or 16q22-24 chromosomal locus amplification, copy gain or translocation or lack thereof, or 16q23 or 16q22-24 chromosomal locus deletions. In embodiments, post-menopausal patients with an increase of the c-MAF gene expression level, copy number, amplification, or gain with respect to a reference (and are therefore at a high risk of a bad DFS or OS outcome) may be administered any treatment disclosed herein. In some embodiments, post menopausal patients with an increase of the c-MAF gene expression level, copy number, amplification, or gain with respect to a reference (and are therefore at a high risk of a bad DFS or OS outcome) may be treated by extending their hormonal treatment beyond the five year time prescribed by the use of hormonal treatments as the standard of care. In certain embodiments, the hormonal treatment is Tamoxifen and/or aromatase inhibitors. Patients without an increase of the c-MAF gene expression level, copy number, amplification, or gain with respect to a reference should not be administered a treatment disclosed herein.

In another aspect, the treatment is an mTor inhibitor. In some aspects, the mTor inhibitor is a dual mTor/PI3kinase inhibitor. In some aspects, the mTor inhibitor is used to prevent or inhibit metastasis, relapse or recurrence. In some aspects the mTor inhibitor is selected from the group consisting of: ABI009 (sirolimus), rapamycin (sirolimus), Abraxane (paclitaxel), Absorb (everolimus), Afinitor (everolimus), Afinitor with Gleevec, AS703026 (pimasertib), Axxess (umirolimus), AZD2014, BEZ235, Biofreedom (umirolimus), BioMatrix (umirolimus), BioMatrix flex (umirolimus), CC115, CC223, Combo Bio-engineered Sirolimus Eluting Stent ORBUSNEICH (sirolimus), Curaxin CBLC102 (mepacrine), DE109 (sirolimus), DS3078, Endeavor DES (zotarolimus), Endeavor Resolute (zotarolimus), Femara (letrozole), Hocena (antroquinonol), INK128, Inspiron (sirolimus), IPI504 (retaspimycin hydrochloride), KRN951 (tivozanib), ME344, MGA031 (teplizumab), MiStent SES (sirolimus), MKC1, Nobori (umirolimus), OSI027, OVI123 (cordycepin), Palomid 529, PF04691502, Promus Element (everolimus), PWT33597, Rapamune (sirolimus), Resolute DES (zotarolimus), RG7422, SAR245409, SF1126, SGN75 (vorsetuzumab mafodotin), Synergy (everolimus), Taltorvic (ridaforolimus), Tarceva (erlotinib), Torisel (temsirolimus), Xience Prime (everolimus), Xience V (everolimus), Zomaxx (zotarolimus), Zortress (everolimus), Zotarolimus Eluting Peripheral Stent MEDTRONIC (zotarolimus), AP23841, AP24170, ARmTOR26, BN107, BN108, Canstatin GENZYME (canstatin), CU906, EC0371, EC0565, KI1004, LOR220, NV128, Rapamycin ONCOIMMUNE (sirolimus), SB2602, Sirolimus PNP SAMYANG BIOPHARMACEUTICALS (sirolimus), TOP216, VLI27, VS5584, WYE125132, XL388, Advacan (everolimus), AZD8055, Cypher Select Plus Sirolimus eluting Coronary Stent (sirolimus), Cypher Sirolimus eluting coronary stent (sirolimus), Drug Coated Balloon (sirolimus), E-Magic Plus (sirolimus), Emtor (sirolimus), Esprit (everolimus), Evertor (everolimus), HBF0079, LCP-Siro (sirolimus), Limus CLARIS (sirolimus), mTOR Inhibitor CELLZOME, Nevo Sirolimus eluting Coronary Stent (sirolimus), nPT-mTOR, Rapacan (sirolimus), Renacept (sirolimus), ReZolve (sirolimus), Rocas (sirolimus), SF1126, Sirolim (sirolimus), Sirolimus NORTH CHINA (sirolimus), Sirolimus RANBAXY (sirolimus), Sirolimus WATSON (sirolimus) Siropan (sirolimus), Sirova (sirolimus), Supralimus (sirolimus), Supralimus-Core (sirolimus), Tacrolimus WATSON (tacrolimus), TAFA93, Temsirolimus ACCORD (temsirolimus), Temsirolimus SANDOZ (temsirolimus), TOP216, Xience Prime (everolimus), Xience V (everolimus). In a specific aspect the mTor inhibitor is Afinitor (everolimus). In another aspect, mTor inhibitors can be identified through methods known in the art. (See, e.g., Zhou, H. et al. Updates of mTor inhibitors. 2010. *Anticancer Agents Med. Chem.* 10(7): 571-81, which is herein incorporated by reference). In some aspects, the mTor inhibitor is used to treat or prevent or inhibit metastasis in a patient that is positive for a hormone receptor. (See. e.g., Baselga, J., el al., Everolimus in Postmenopausal Hormone-Receptor Positive Advanced Breast Cancer. 2012. *N. Engl. J. Med.* 366(6): 520-529). In some aspects, the mTor inhibitor is used to treat or prevent or inhibit metastasis in a patient with advanced breast cancer. In some aspects, the mTor inhibitor is used in combination with a second treatment. In some aspects, the second treatment is any treatment described herein.

In another aspect, the treatment is a Src kinase inhibitor. In some aspects, the Src inhibitor is used to prevent or inhibit metastasis, relapse or recurrence. In some aspects, the Src kinase inhibitor is selected from the group: AZD0530 (saracatinib), Bosulif (bosutinib), ENMD981693, KDO20, KX01, Sprycel (dasatinib), Yervoy (ipilimumab), AP23464, AP23485, AP23588, AZD0424, c-Src Kinase Inhibitor KISSEI, CU201, KX2361, SKS927, SRN004, SUNK706, TG100435, TG100948, AP23451, Dasatinib HETERO (dasatinib), Dasatinib VALEANT (dasatinib), Fontrax (dasatinib), Src Kinase Inhibitor KINEX, VX680, (tozasertib lactate), XL228, and SUNK706. In some embodiments, the Src kinase inhibitor is dasatinib. In another aspect, Src kinase inhibitors can be identified through methods known in the art (See, e.g., Sen, B. and Johnson, F. M. Regulation of Src Family Kinases in Human Cancers. 2011. *J. Signal Transduction.* 2011: 14 pages, which is herein incorporated by reference). In some aspects, the Src kinase inhibitor is used to treat or prevent or inhibit metastasis, relapse or recurrence in a patient that is positive for the SRC-responsive signature (SRS). In some aspects, the patient is SRS+ and ER-. (See. e.g., Zhang, CH.-F, et al. Latent Bone Metastasis in Breast Cancer Tied to Src-Dependent survival signals. 2009. *Cancer Cell.* 16: 67-78, which is herein incorporated by reference.) In some aspects, the Src kinase inhibitor is used to treat or prevent or inhibit metastasis in a patient with advanced breast cancer. In some aspects, the Src kinase inhibitor is used in combination with a second treatment. In some aspects, the second treatment is any treatment described herein.

In another aspect, the treatment is a COX-2 inhibitor. In some aspects, the COX-2 inhibitor is used to prevent or inhibit metastasis, relapse or recurrence. In some aspects, the COX-2 inhibitor is selected from the group: ABT963, Acetaminophen ER JOHNSON (acetaminophen), Acular X (ketorolac tromethamine), BAY1019036 (aspirin), BAY987111 (diphenhydramine, naproxen sodium), BAY11902 (piroxicam), BCIBUCH001 (ibuprofen), Capoxigem (apricoxib), C S502, C S670 (pelubiprofen), Diclofenac HPBCD (diclofenac), Diractin (ketoprofen), GW406381, HCT1026 (nitroflurbiprofen), Hyanalgese-D (diclofenac), HydrocoDex (acetaminophen, dextromethorphan, hydrocodone), Ibuprofen Sodium PFIZER (ibuprofen sodium), Ibuprofen with Acetaminophen PFIZER (acetaminophen, ibuprofen), Impracor (ketoprofen), IP880 (diclofenac), IP940 (indomethacin), ISV205 (diclofenac sodium), JNS013 (acetaminophen, tramadol hydrochloride), Ketoprofen TDS (ketoprofen), LTNS001 (naproxen etemesil), Mesalamine SALIX (mesalamine), Mesalamine SOFAR (mesalamine), Mesalazine (mesalamine), ML3000 (licofelone), MRX7EAT (etodolac), Naproxen IROKO (naproxen), NCX4016 (nitroaspirin), NCX701 (nitroacetaminophen), Nuprin SCOLR (ibuprofen), OMS103HP (amitriptyline hydrochloride, ketoprofen, oxymetazoline hydrochloride), Oralease (diclofenac), OxycoDex (dextromethorphan, oxycodone), P54, PercoDex (acetaminophen, dextromethorphan, oxycodone), PL3100 (naproxen, phosphatidyl choline), PSD508, R-Ketoprofen (ketoprofen), Remura (bromfenac sodium), ROX828 (ketorolac tromethamine), RP19583 (ketoprofen lysine), RQ00317076, SDX101 (R-etodolac), TDS943 (diclofenac sodium), TDT070 (ketoprofen), TPR100, TQ1011 (ketoprofen), TT063 (S-flurbiprofen), UR8880 (cimicoxib), V0498TA01A (ibuprofen), VT122 (etodolac, propranolol), XP20B (acetaminophen, dextropropoxyphene), XP21B (diclofenac potassium), XP21L (diclofenac potassium), Zoenasa (acetylcysteine, mesalamine), Acephen, Actifed Plus, Actifed-P, Acular, Acular LS, Acular PF, Acular X, Acuvail, Advil, Advil Allergy Sinus, Advil Cold and Sinus, Advil Congestion Relief, Advil PM, Advil PM Capsule, Air Salonpas, Airtal, Alcohol-Free NyQuil Cold & Flu Relief, Aleve, Aleve ABDI IBRAHIM, Aleve-D, Alka-Seltzer, Alka-Seltzer BAYER, Alka-Seltzer Extra Strength, Alka-Seltzer Lemon-Lime, Alka-Seltzer Original, Alka-Seltzer Plus, Alka-Seltzer plus Cold and Cough, Alka-Seltzer plus Cold and Cough Formula, Alka-Seltzer Plus Day and Night Cold Formula, Alka-Seltzer Plus Day Non-Drowsy Cold Formula, Alka-Seltzer Plus Flu Formula, Alka-Seltzer Plus Night Cold Formula, Alka-Seltzer Plus Sinus Formula, Alka-Seltzer Plus Sparkling Original Cold Formula, Alka-Seltzer PM, Alka-Seltzer Wake-Up Call, Anacin, Anaprox, Anaprox MINERVA, Ansaid, Apitoxin, Apranax, Apranax abdi, Arcoxia, Arthritis Formula Bengay, Arthrotec, Asacol, Asacol HD, Asacol MEDUNA ARZNEIMITTEL, Asacol ORIFARM, Aspirin BAYER, Aspirin Complex, Aspirin Migran, AZD3582, Azulfidine, Baralgan M, BAY1019036, BAY987111, BAY11902, BCIBUCH001, Benadryl Allergy, Benadryl Day and Night, Benylin 4 Flu, Benylin Cold and Flu, Benylin Cold and Flu Day and Night, Benylin Cold and Sinus Day and Night, Benylin Cold and Sinus Plus, Benylin Day and Night Cold and Flu Relief, Benylinl All-In-One, Brexin, Brexin ANGELINI, Bromday, Bufferin, Buscopan Plus, Caldolor, Calmatel, Cambia, Canasa, Capoxigem, Cataflam, Celebrex, Celebrex ORIFARM, Children's Advil Allergy Sinus, Children's Tylenol, Children's Tylenol Cough and Runny Nose, Children's Tylenol plus cold, Children's Tylenol plus Cold and Cough, Children's Tylenol plus cold and stuffy nose, Children's Tylenol plus Flu, Children's Tylenol plus cold & allergy, Children's Tylenol plus Cough & Runny Nose, Children's Tylenol plus Cough & Sore Throat, Children's Tylenol plus multi symptom cold, Clinoril, Codral Cold and Flu, Codral Day and Night Day Tablets, Codral Day and Night Night Tablets, Codral Nighttime, Colazal, Combunox, Contac Cold plus Flu, Contac Cold plus Flu Non-Drowsy, Coricidin D, Coricidin HBP Cold and Flu, Coricidin HBP Day and Night Multi-Symptom Cold, Coricidin HBP Maximum Strength Flu, Coricidin HBP Nighttime Multi-Symptom Cold, Coricidin II Extra Strength Cold and Flu, CS502, CS670, Daypro, Daypro Alta, DDSO6C, Demazin Cold and Flu, Demazin Cough, Cold and Flu, Demazin day/night Cold and Flu, Demazin PE Cold and Flu, Demazin PE day/night Cold and Flu, Diclofenac HPBCD, Dimetapp Day Relief, Dimetapp Multi-Symptom Cold and Flu, Dimetapp Night Relief, Dimetapp Pain and Fever Relief, Dimetapp PE Sinus Pain, Dimetapp PE Sinus Pain plus Allergy, Dipentum, Diractin, Disprin Cold 'n' Fever, Disprin Extra, Disprin Forte. Disprin Plus, Dristan Cold, Dristan Junior, Drixoral Plus, Duexis, Dynastat, Efferalgan, Efferalgan Plus Vitamin C, Efferalgan Vitamin C, Elixsure IB, Excedrin Back and Body, Excedrin Migraine, Excedrin PM, Excedrin Sinus Headache, Excedrin Tension Headache, Falcol, Fansamac, Feldene, Fever-All, Fiorinal, Fiorinal with Codeine, Flanax, Flector Patch, Flucam, Fortagesic, Gerbin, Giazo, Gladio, Goody's Back and Body Pain, Goody's Cool Orange, Goody's Extra Strength, Goody's PM, Greaseless Bengay, GW406381, HCT1026, He Xing Yi, Hyanalgese-D, HydrocoDex, Ibuprofen Sodium PFIZER, Ibuprofen with, Acetaminophen PFIZER, Icy Hot SANOFI AVENTIS, Impracor, Indocin, Indomethacin APP PHARMA, Indomethacin MYLAN, Infants' Tylenol, IP880, IP940, Iremod, ISV205, JNS013, Jr. Tylenol, Junifen, Junior Strength Advil, Junior Strength Motrin, Ketoprofen TDS, Lemsip Max, Lemsip Max All in One, Lemsip Max All Night, Lemsip Max Cold and Flu, Lialda, Listerine Mouth Wash, Lloyds Cream, Lodine, Lorfit P, Loxonin, LTNS001, Mersyndol, Mesalamine SALIX, Mesalamine SOFAR, Mesalazine, Mesasal GLAXO, Mesasal SANOFI, Mesulid, Metsal Heat Rub, Midol Complete, Midol Extended Relief, Midol Liquid Gels, Midol PM, Midol Teen Formula, Migranin COATED TABLETS, ML3000, Mobic, Mohrus, Motrin, Motrin Cold and Sinus Pain, Motrin PM, Movalis ASPEN, MRX7EAT, Nalfon, Nalfon PEDINOL, Naprelan, Naprosyn, Naprosyn RPG LIFE SCIENCE, Naproxen IROKO, NCX4016, NCX701, NeoProfen LUNDBECK, Nevanac, Nexcede, Niflan, Norgesic MEDICIS, Novalgin, Nuprin SCOLR, Nurofen, Nurofen Cold and Flu, Nurofen Max Strength Migraine, Nurofen Plus, Nuromol, NyQuil with Vitamin C, Ocufen, OMS103HP, Oralease, Orudis ABBOTT JAPAN, Oruvail, Osteluc, OxycoDex, P54, Panadol, Panadol Actifast, Paradine, Paramax, Parfenac, Pedea, Pennsaid, Pentasa, Pentasa ORIFARM, Peon, Percodan, Percodan-Demi, PercoDex, Percogesic, Perfalgan, PL2200, PL3100, Ponstel, Prexige, Prolensa, PSD508, R-Ketoprofen, Rantudil, Relafen, Remura, Robaxisal, Rotec, Rowasa, ROX828, RP19583, RQ00317076, Rubor, Salofalk, Salonpas, Saridon, SDX101, Seltouch, sfRowasa, Shinbaro, Sinumax, Sinutab, Sinutab, sinus, Spalt, Sprix, Strefen, Sudafed Cold and Cough, Sudafed Head Cold and Sinus, Sudafed PE Cold plus Cough, Sudafed PE Pressure plus Pain, Sudafed PE, Severe Cold, Sudafed PE Sinus Day plus Night Relief Day Tablets, Sudafed PE Sinus Day plus Night Relief Night Tablets, Sudafed PE Sinus plus Anti-inflammatory Pain Relief, Sudafed Sinus Advance, Surgam, Synalgos-DC, Synflex, Tavist allergy/sinus/headache, TDS943, TDT070, Theraflu Cold and Sore Throat, Theraflu Daytime Severe Cold and Cough, Theraflu Daytime Warming Relief, Theraflu Warming Relief Caplets Daytime Multi-Symptom Cold, Theraflu Warming Relief Cold and Chest Congestion, Thomapyrin, Thomapyrin C, Thomapyrin Effervescent, Thomapyrin Medium, Tilcotil, Tispol, Tolectin, Toradol, TPR100, TQ1011, Trauma-Salbe, Trauma-Salbe Kwizda, Treo, Treximet, Trovex, TT063, Tylenol, Tylenol Allergy Multi-Symptom, Tylenol Back Pain, Tylenol Cold & Cough Daytime, Tylenol Cold & Cough Nighttime, Tylenol Cold and Sinus Daytime, Tylenol Cold and Sinus Nighttime, Tylenol Cold Head Congestion Severe, Tylenol Cold Multi Symptom Daytime, Tylenol Cold Multi Symptom Nighttime Liquid, Tylenol Cold Multi Symptom Severe, Tylenol Cold Non-Drowsiness Formula, Tylenol Cold Severe Congestion Daytime, Tylenol Complete Cold, Cough and Flu Night time, Tylenol Flu Nighttime, Tylenol Menstrual, Tylenol PM, Tylenol Sinus Congestion & Pain Daytime, Tylenol Sinus Congestion & Pain Nighttime, Tylenol Sinus Congestion & Pain Severe, Tylenol Sinus Severe Congestion Daytime, Tylenol Ultra Relief, Tylenol with Caffeine and Codeine phosphate, Tylenol with Codeine phosphate, Ultra Strength Bengay Cream, Ultracet, UR8880, V0498TA01A, Vicks NyQuil Cold and Flu Relief, Vicoprofen, Vimovo, Voltaren Emulgel, Voltaren GEL, Voltaren NOVARTIS CONSUMER HEALTH GMBH, Voltaren XR, VT122, Xefo, Xefo Rapid, Xefocam, Xibrom, XL3, Xodol, XP20B, XP21B, XP21L, Zipsor, and Zoenasa. In another aspect, COX-2 inhibitors can be identified through methods known in the art (See, e.g., Dannhardt, G. and Kiefer, W. Cyclooxygenase inhibitors—current status and future prospects. 2001. *Eur. J. Med. Chem.* 36: 109-126, which is herein incorporated by reference). In some aspects, the COX-2 inhibitor is used to treat or prevent or inhibit metastasis in a patient with advanced breast cancer. In some aspects, the COX-2 inhibitor is used in combination with a second treatment. In some aspects, the second treatment is any treatment described herein. In some aspects, the COX-2 inhibitor is used in combination with a second treatment selected from the group consisting of: Denosumab, Zometa, Carbozantinib or Cabozantinib, Antibody or peptide blocking PTHLH (parathyroid hormone like hormone) or PTHrP (parathyroid hormone related protein).

In one embodiment, the treatment is Radium 223. In an embodiment the Radium 223 therapy is Alpharadin (aka, Xofigo) (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth. Radium-223, after injection, is carried in the bloodstream to sites of abnormal bone growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer or a metastasis. The aim with radium-223 is to selectively target this secondary cancer. Any radium-223 not taken-up in the bones is quickly routed to the gut and excreted.

In some embodiments, the treatment is a CDK4/6 inhibitor. In particular embodiments, the CDK4/6 inhibitor is selected from any known CDK4/6 inhibitors. In still further embodiments, the CDK4/6 inhibitor is Palbociclib (PD-0332991), Ribociclib (LEE011), or Abemaciclib (LY2835219). The use of CDK4/6 inhibitors is described in Finn et al. *Breast Cancer Research* 18:17 (2016).

Alternatively a combined treatment can be carried out in which more than one agent from those mentioned above are combined to treat and/or prevent the metastasis, relapse or recurrence or said agents can be combined with other supplements, such as calcium or vitamin D or with a hormone treatment.

In embodiments, MAF positive postmenopausal patients at high risk of DFS or bad OS outcome are treated in the adjuvant setting with any therapy to improve the outcome of the patients. These therapies include any therapy disclosed herein, including agents for avoiding or preventing bone remodeling, agents to improve disease free survival or overall survival, c-MAF inhibitory agents, chemotherapy, hormone therapy, m-Tor inhibitors, CDK4/6 inhibitors, Radium-223, a CCR5 antagonist, a Src kinase inhibitor, or a COX-2 inhibitor and combinations thereof. Patients who are not MAF positive should not be administered such agents or therapies.

When the cancer has metastasized, systemic treatments including but not limited to chemotherapy, hormone treatment, immunotherapy, or a combination thereof are used. Additionally, radiotherapy and/or surgery can be used. The choice of treatment generally depends on the type of primary cancer, the size, the location of the metastasis, the age, the general health of the patient and the types of treatments used previously.

The systemic treatments are those that reach the entire body:
  Chemotherapy is the use of medicaments to destroy cancer cells. The medicaments are generally administered through oral or intravenous route. In other embodiments, the treatment is chemotherapy. In some embodiments, the chemotherapy is any chemotherapy that is known in the art. In particular embodiments, the chemotherapy is adjuvant chemotherapy. In certain embodiments, the chemotherapy is a taxane. In further embodiments, the taxane is Paclitaxel (Taxol), docetaxel (Taxotere) or Cabazitaxel. The medicaments are generally administered through oral or intravenous route. Sometimes, chemotherapy is used together with radiation treatment. Hormone therapy is based on the fact that some hormones promote cancer growth. For example, estrogen in women produced by the ovaries sometimes promotes the breast cancer growth. There are several ways for stopping the production of these hormones. A way is to remove the organs producing them: the ovaries in the case of women, the testicles in the case of the men. More frequently, medicaments to prevent these organs from producing the hormones or to prevent the hormones from acting on the cancer cells can be used. In embodiments, the treatment is hormone therapy. In certain embodiments, the hormone therapy is Tamoxifen and/or an aromatase inhibitor.

Immunotherapy is a treatment that aids the immune system itself of the patient to combat cancer. There are several types of immunotherapy which are used to treat metastasis patients. These include but are not limited to cytokines, monoclonal antibodies and antitumor vaccines.

The agents for avoiding or preventing bone remodelling are typically administered in combination with a pharmaceutically acceptable carrier.

The term "carrier" refers to a diluent or an excipient whereby the active ingredient is administered. Such pharmaceutical carriers can be sterile liquids such as water and oil, including those of a petroleum, animal, plant or synthetic origin such peanut oil, soy oil, mineral oil, sesame oil and the like. Water or aqueous saline solutions and aqueous dextrose and glycerol solutions, particularly for injectable solutions, are preferably used as carriers. Suitable pharmaceutical carriers are described in "Remington's Pharmaceutical Sciences" by E. W. Martin, 1995. Preferably, the carriers of the invention are approved by the state or federal government regulatory agency or are listed in the United States Pharmacopeia or other pharmacopeia generally recognized for use thereof in animals and more particularly in human beings.

The carriers and auxiliary substances necessary for manufacturing the desired pharmaceutical dosage form of the pharmaceutical composition of the invention will depend, among other factors, on the pharmaceutical dosage form chosen. Said pharmaceutical dosage forms of the pharmaceutical composition will be manufactured according to the conventional methods known by the person skilled in the art. A review of the different methods for administering active ingredients, excipients to be used and processes for producing them can be found in "Tratado de Farmacia Galénica", C. Fauli i Trillo, Luzán 5, S.A. 1993 Edition. Examples of pharmaceutical compositions include any solid composition (tablets, pills, capsules, granules, etc.) or liquid composition (solutions, suspensions or emulsions) for oral, topical or parenteral administration. Furthermore, the pharmaceutical composition may contain, as deemed necessary, stabilizers, suspensions, preservatives, surfactants and the like.

For use in medicine, the bone remodelling agents can be found in the form of a prodrug, salt, solvate or clathrate, either isolated or in combination with additional active agents and can be formulated together with a pharmaceutically acceptable excipient. Excipients preferred for use thereof in the present invention include sugars, starches, celluloses, rubbers and proteins. In a particular embodiment, the pharmaceutical composition of the invention will be formulated in a solid pharmaceutical dosage form (for example tablets, capsules, pills, granules, suppositories, sterile crystal or amorphous solids that can be reconstituted to provide liquid forms etc.), liquid pharmaceutical dosage form (for example solutions, suspensions, emulsions, elixirs, lotions, ointments etc.) or semisolid pharmaceutical dosage form (gels, ointments, creams and the like). The pharmaceutical compositions of the invention can be administered by any route, including but not limited to the oral route, intravenous route, intramuscular route, intraarterial route, intramedularry route, intrathecal route, intraventricular router, transdermal route, subcutaneous route, intraperitoneal route, intranasal route, enteric route, topical route, sublingual route or rectal route. A review of the different ways for administering active ingredients, of the excipients to be used and of the manufacturing processes thereof can be found in Tratado de Farmacia Galénica, C. Fauli i Trillo, Luzán 5, S.A., 1993 Edition and in Remington's Pharmaceutical Sciences (A. R. Gennaro, Ed.), 20$^{th}$ edition, Williams & Wilkins Pa., USA (2000). Examples of pharmaceutically acceptable carriers are known in the state of art and include phosphate buffered saline solutions, water, emulsions such as oil/water emulsions, different types of wetting agents, sterile solutions, etc. The compositions comprising said carriers can be formulated by conventional processes known in the state of the art.

The bone remodelling-avoiding and preventing agents or the pharmaceutical compositions containing them can be administered at a dose of less than 10 mg per kilogram of body weight, preferably less than at least about 50, 40, 30, 20, 10, 5, 2, 1, 0.5, 0.1, 0.05, 0.01, 0.005, 0.001, 0.0005, 0.0001, 0.00005 or 0.00001 mg per kg of body weight. The unit dose can be administered by injection, inhalation or topical administration. In particular embodiments, the agent is administered at its approved dose.

The dose depends on the severity and the response of the condition to be treated and it may vary between several days and months or until the condition subsides. The optimal dosage can be determined by periodically measuring the concentrations of the agent in the body of the patient. The optimal dose can be determined from the EC50 values obtained by means of previous in vitro or in vivo assays in animal models. The unit dose can be administered once a day or less than once a day, preferably less than once every 2, 4, 8 or 30 days. Alternatively, it is possible to administer a starting dose followed by one or several maintenance doses, generally of a lesser amount than the starting dose. The maintenance regimen may involve treating the patient with a dose ranging between 0.01 μg and 1.4 mg/kg of body weight per day, for example 10, 1, 0.1, 0.01, 0.001, or 0.00001 mg per kg of body weight per day. The maintenance doses are preferably administered at the most once every 5, 10 or 30 days. The treatment must be continued for a time that will vary according to the type of disorder the patient suffers, the severity thereof and the condition of the patient. After treatment, the progress of the patient must be monitored to determine if the dose should be increased in the event that the disease does not respond to the treatment or the dose is reduced if an improvement of the disease is observed or if unwanted side effects are observed.

Kits of the Invention

In another aspect the invention relates to a kit for determining a therapy for a subject suffering from breast cancer, the kit comprising: a) means for quantifying the expression level, copy number, amplification, gain or translocation of c-MAF in a sample of said subject; b) means for comparing the quantified expression level, copy number, amplification, gain or translocation of c-MAF in said sample to a reference c-MAF expression level; and c) means for determining a therapy or excluding a therapy from consideration for said subject based on the comparison of the quantified expression level to the reference expression level.

Means for quantifying the expression level of c-MAF in a sample of said subject have been previously described in detail including 16q23 and 16q22-24 locus amplification, gain and/or translocation. In some embodiments, the means for quantifying the c-MAF expression is any antibody, antigen binding molecule or fragment described herein. In some embodiments, the antibody is any antibody described in Int'l Appl. No. PCT/IB2015/059562, which is incorporated herein by reference in its entirety.

In a preferred embodiment, means for quantifying expression comprise a set of probes and/or primers that specifically bind and/or amplify the c-MAF gene.

All the particular embodiments of the methods of the present invention are applicable to the kits of the invention and to their uses.

Method for Classifying a Subject Suffering from Breast Cancer.

In another aspect, the invention relates to a method for classifying a subject suffering from breast cancer into a cohort, comprising: a) determining the expression level, copy number, amplification, gain or translocation of c-MAF in a sample of said subject; b) comparing the expression level, copy number, amplification, gain or translocation 1 of c-MAF in said sample to a predetermined reference level of c-MAF expression; and c) classifying said subject into a cohort based on said expression level, copy number, amplification, gain or translocation of c-MAF in the sample.

In some embodiments, the c-MAF gene expression level is used to stratify patients into groups for treatment based on their c-MAF expression level. In embodiments, patients with a high c-MAF expression level receive a different treatment than patients with a low c-MAF expression level. In embodiments, the patients are further stratified based on their menopausal status. In embodiments, the patients are stratified based on whether they are post-menopausal or non-post-menopausal. In certain embodiments, the subjects are administered different treatments based on their c-MAF expression levels and/or their post-menopausal or non-post-menopausal status. In some embodiments, the stratified patients are administered an agent that avoids or prevents bone remodelling. In embodiments, the agent that avoids or prevents bone remodeling is an agent that avoids or prevents bone degradation. In further embodiments, the agent that avoids or prevents bone degradation is zoledronic acid. In other embodiments, the c-MAF gene expression level is used to select patients for treatment. In some embodiments, the patients are stratified into groups for clinical trials.

Means for quantifying the expression level of c-MAF in a sample of said subject have been previously described in detail including 16q23 and 16q22-24 locus amplification, gain and/or translocation.

In another preferred embodiment said cohort is for conducting a clinical trial.

In a preferred embodiment, the sample is a tumor tissue sample.

The following examples illustrate the invention and do not limit the scope thereof.

EXAMPLES

Example 1: Validation of c-MAF as a Metastasis Marker

The IHC and FISH assays used to test c-MAF in the AZURE samples were analytically validated. An overview of the assay validation parameters can be seen in FIG. 1.

The MAF FISH assay was produced by Kreatech for Inbiomotion based on KREATECH proprietary FISH technology. The probe set contains two probes: a MAF 16q23 probe plus a D16Z3 probe as control of chromosome 16 centromeric region. The assay was validated using a 16q23/D16Z3 probe (Inbiomotion) and Poseidon Tissue Digestion Kit from Kreatech. The scoring criteria were defined in a fact sheet and as follows: two FISH evaluable results per patient, and the highest value was selected. The scoring algorithm was as follows: 20 cells counted for target and centromere amplification, if the gene count is >2 and ≤3, then 50 cells were counted.

The MAF IHC assay was based on a recombinant monoclonal antibody (described in Int'l Appl. No. PCT/IB2015/059562, which is incorporated herein by reference in its entirety). The antibody was selected based on IHC. The assay was validated using MAF RecMab (Inbiomotion) with DAKO AS LINK platform and protocol on control specimens provided by Inbiomotion. The scoring criterion was defined upfront in a fact sheet, and there was one single IHC Hscore per patient. The scoring algorithm was the H-score.

Figure 2:
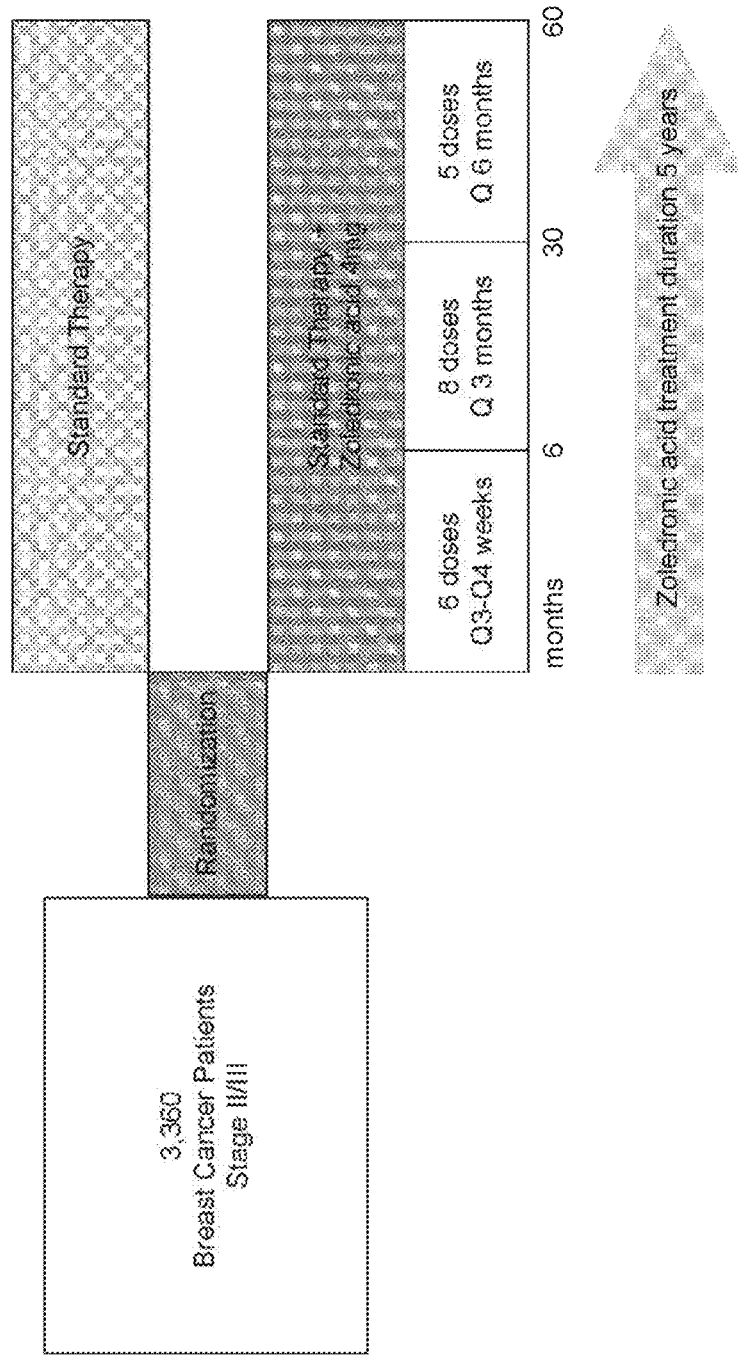
FIG. 2. AZURE study design.
Figure 3:
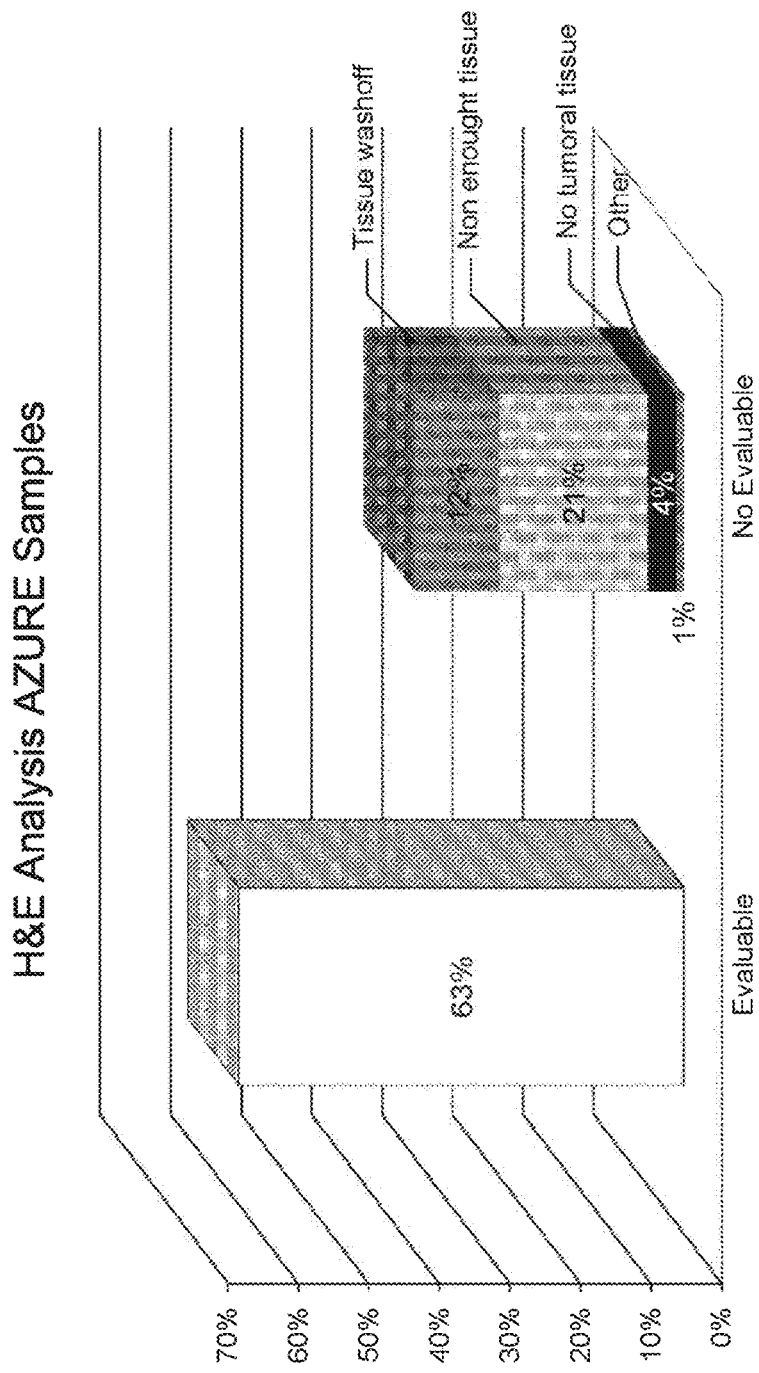
FIG. 3. H&E analysis of AZURE samples. Evaluable and non-evaluable samples are indicated.

An overview of the AZURE clinical trial (Coleman et al N Eng J Med 2011; 365: 1396-1405 and AZURE Current Controlled Trials number, ISRCTN79831382 and ClinicalTrials.gov identifier NCT00072020) study design, whose patients were used to validate MAF, is provided in FIG. 2. MAF was validated in a retrospective analysis of the AZURE trial using patient tumor sample prospectively collected under regulatory compliant conditions. Out of the 3360 patients recruited, 1,769 donated tumor tissue (52.4%). There were 13 TMAs (tissue micro array) (150 patient samples each) (1,769 patients). There were 4 replicas of each TMA using different tissue cores (6,326 (4×patient)). One TMA had only 1 replica and two TMAs had three replicas. Based on the H&E analysis (hematoxilyin and eosin) (FIG. 3) (6,326): 3978 cores were evaluable (63%) and 2348 were nonevaluable.

For the FISH assay, there were 2,067 FISH evaluable cores (56%). There were 865 patients (49%) with two FISH evaluable cores (26% of the AZURE patients) and 1,202 patients had a single FISH score (68%). 567 patients were nonevaluable by FISH in any of the 4 replicas (32%).

Figure 4A:
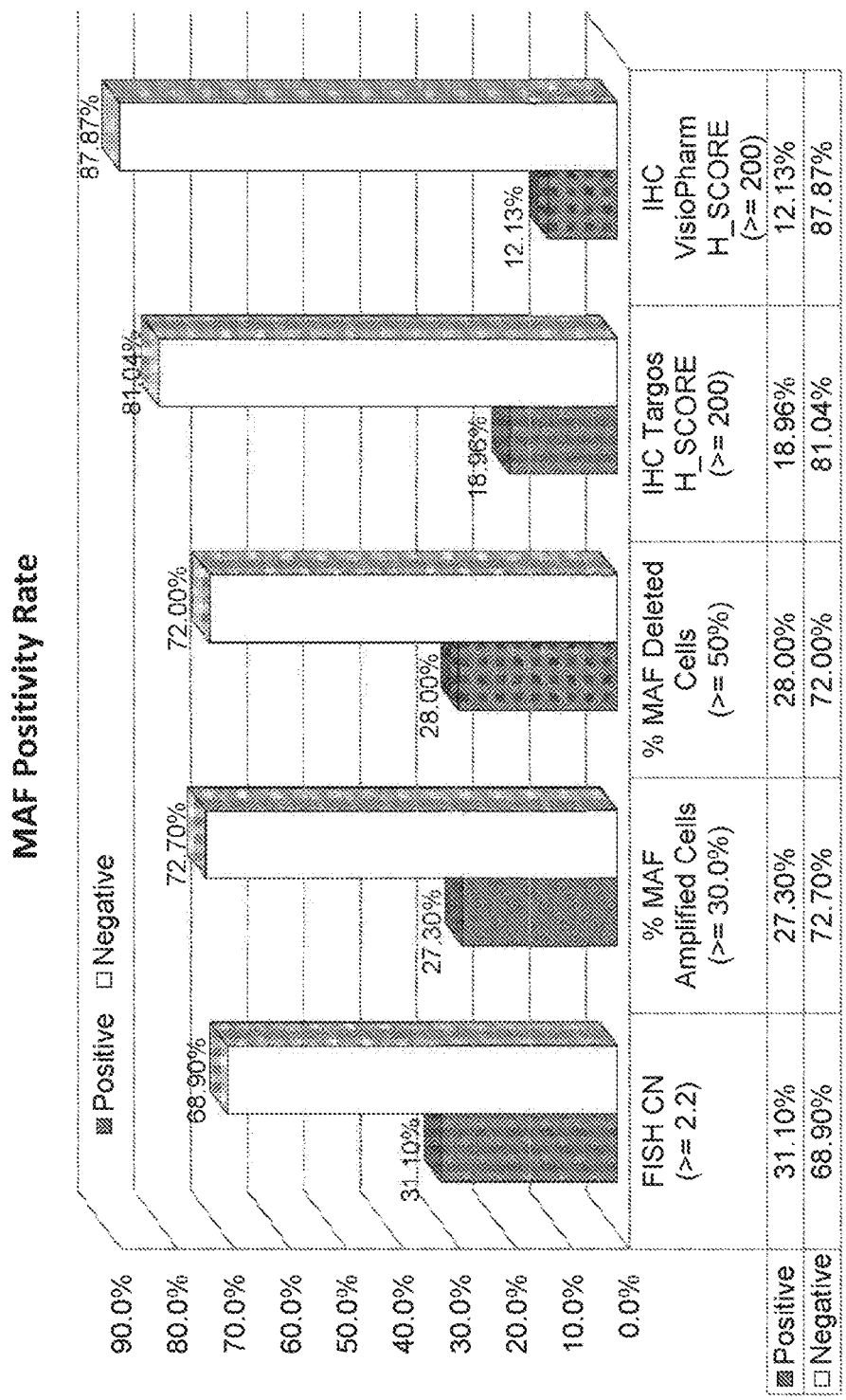
FIG. 4A and FIG. 4B. MAF positivity rate.
Figure 4B:
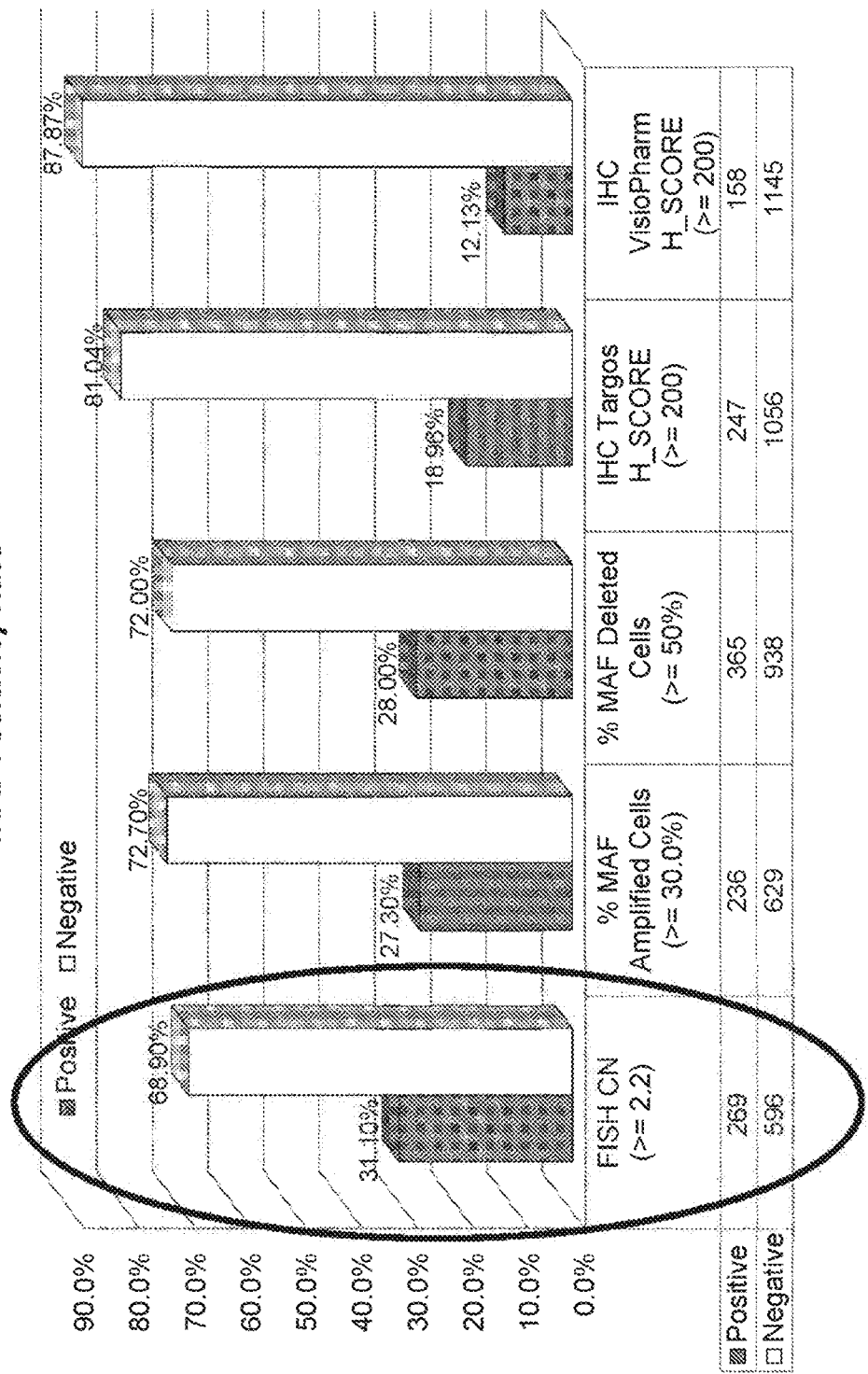

For the IHC assay, a pathologist evaluation and a VisoPharm computer assisted evaluation were performed. For the pathologist evaluation, 2,232 cores were evaluated (59% evaluable for HScore). There were 1390 patients with an IHC HScore (74%), representing 39% of the total AZURE patients. There were 460 patients that were nonevaluable by IHC in any of the four replicas. In the VisioPharm computer assisted IHC staining evaluation, 1299 IHC patients were evaluated out of 1309 scored by pathologists for HScore and mean staining per nuclei. The MAF positivity rate can be seen in FIGS. 4A and 4B.

Figure 5:
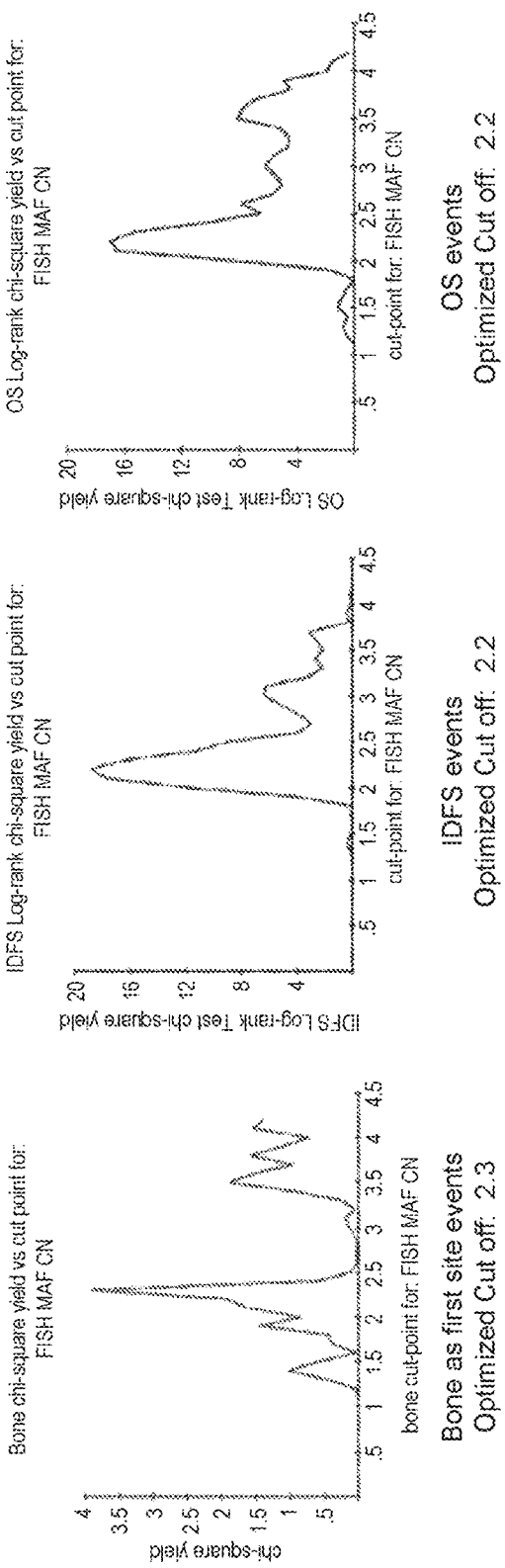
FIG. 5. MAF cut-off optimized FISH data. A sharp spike on the cutpoint graph indicates that the MAF FISH value truly is a threshold event. Additionally, the predefined cut-off is close to the optimized cut-off.

The cut-off optimized FISH data can be seen in FIG. 5 and were calculated as described in Vipery et al KO 2014 DOI: 10.1200/JCO.2013.53.3604.

With regard to molecular variables, for FISH analysis: MAF copy number:

numerical and categorical (+/− cut-off>=2.5) variable; % of nucleic MAF amplified (MAF CN>2):numberical+categorical (cut-off TBD). For the IHC analysis: IHC H-Score: numerical+categorical (cut-off=200), IHC OD: numerical+categorical (cut-off tBD). The following clinical variables were analyzed: disease-free survival (DFS), invasive disease-free survival (IDFS), overall survival (OS), first recurrence in bone, bone recurrence at any time, time to first DFS event in bone, time to first DFS event not in bone, response to zoledronic acid treatment.

In analyzing the MAF FISH prognostic value, the patients from the control and treatment arms were pooled for the initial analysis. Optimized cut-offs for each variable to be analyzed were used when indicated. Death as a competing event was used in time to bone metastasis, anytime. The following clinical variables were analyzed: time to bone metastasis (anytime), time to bone metastasis (as first event), IDFS (including ipsilateral invasive breast tumor recurrence, regional invasive breast cancer recurrence, metastatic disease-breast cancer, death attributable to any cause, including breast cancer, contralateral invasive breast cancer, second primary non-breast invasive cancer), and overall survival.

Figure 6:
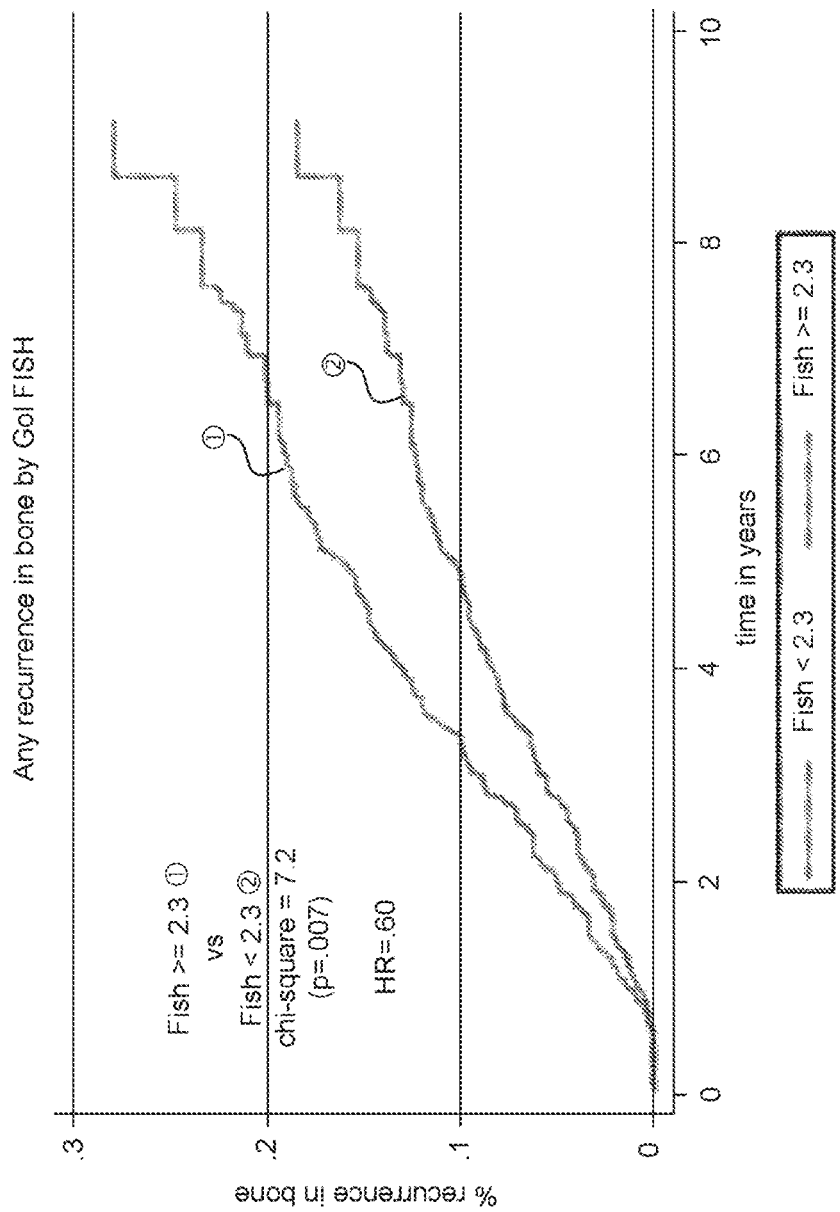
FIG. 6. Risk of bone recurrence based on MAF FISH value.
Figure 7:
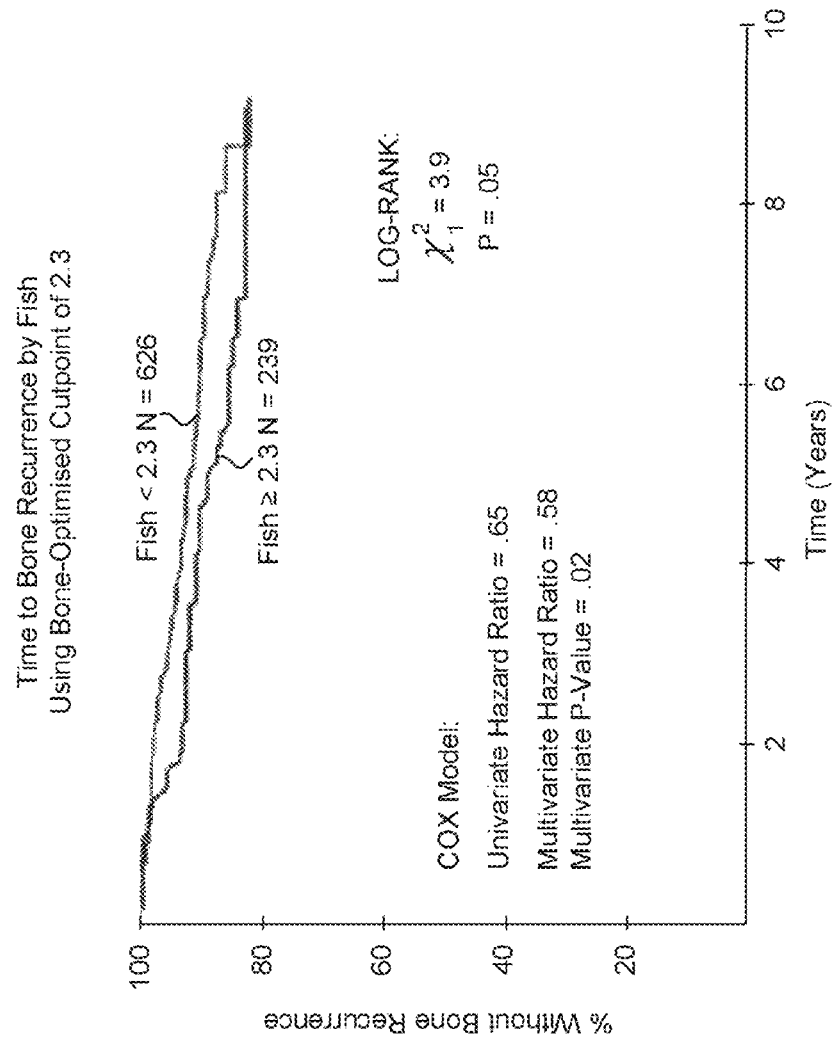
FIG. 7. Time to bone recurrence by MAF FISH value using a bone-optimized cutoff of 2.3.
Figure 8:
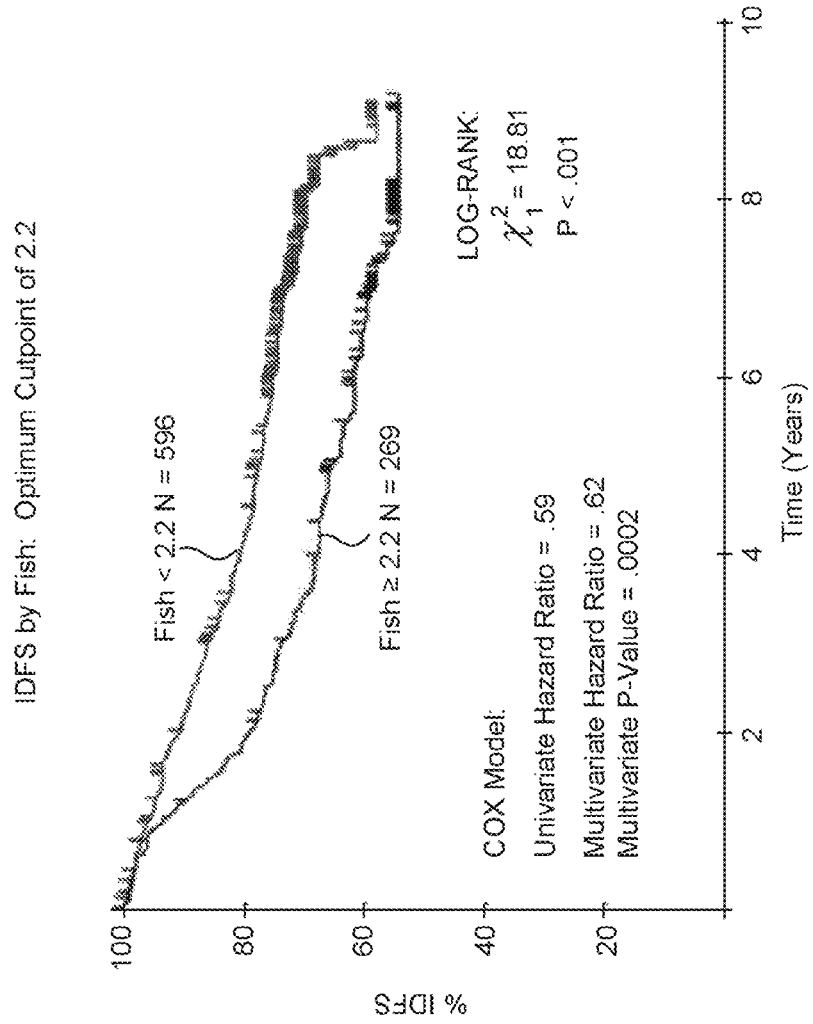
FIG. 8. Percent IDFS by FISH. An optimum cutoff of 2.2 was used.
Figure 9:
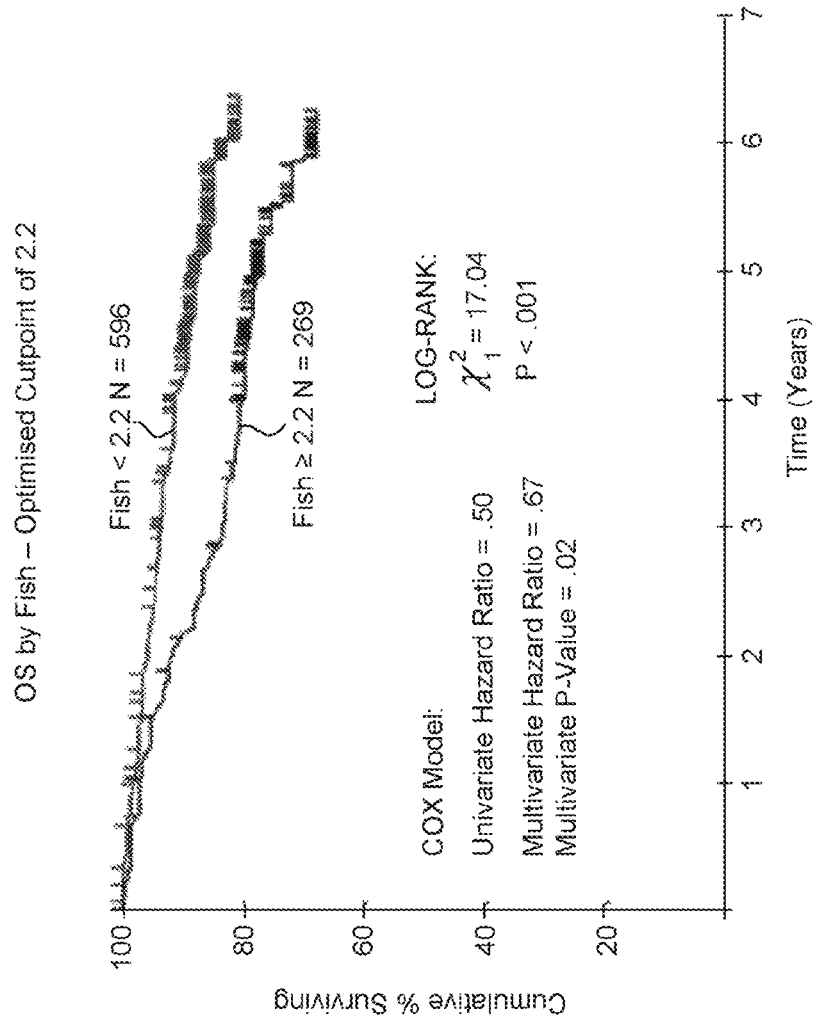
FIG. 9. Overall survival by FISH. An optimum cutoff of 2.2 was used.

FIG. 6 shows that the risk for of bone metastasis was 40% higher in MAF FISH positive patients (>=2.3)(p=0.007) when all patients are analyzed (death as a competing event is used in time to bone metastasis (anytime)). FIG. 7 shows that there was a 42% higher risk for bone as the first metastasis site in MAF FISH positive patients (>=2.3) (p=0.02, multivariate analysis). As seen in FIG. 8, the risk for IDFS was 38% higher in MAF FISH positive patients (>=2.2) (p=0.0002, multivariate analysis) (there is a very early separation by two years then the curves parallel). FIG. 9 shows that overall survival was 33% lower in MAF FISH positive patients (>=2.2) (p=0.02, multivariate analysis) (there is an early separation by three years for the overall survival).

Figure 10:
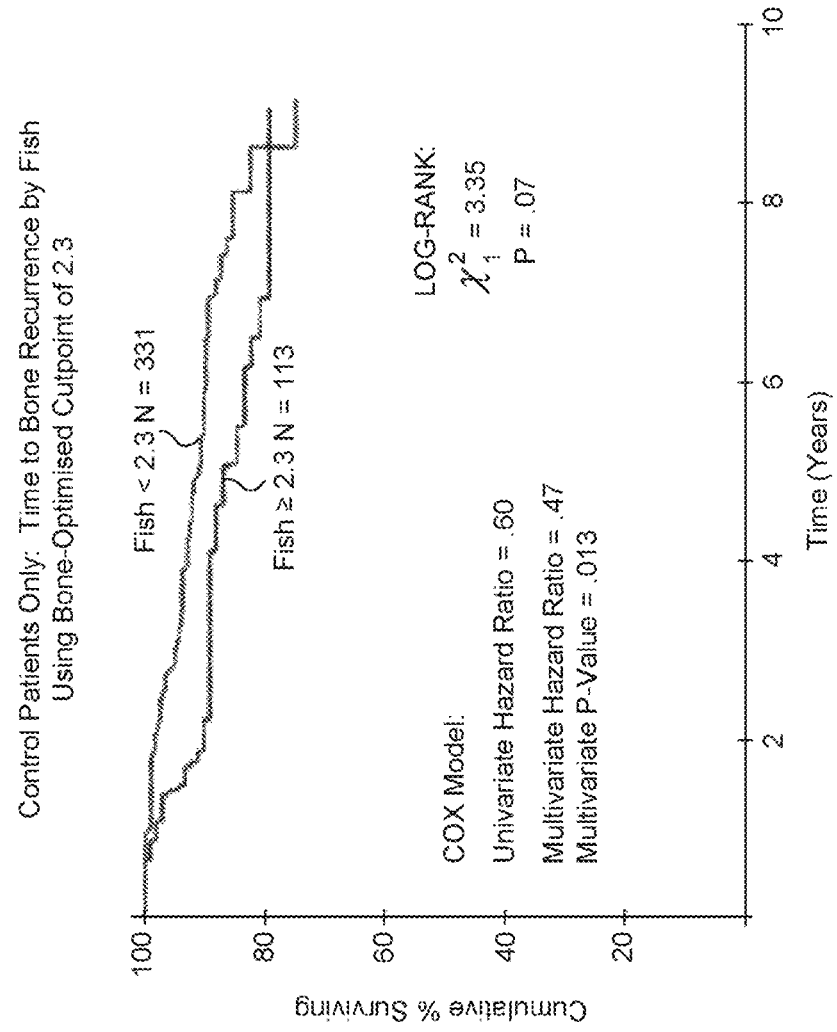
FIG. 10. Time to bone recurrence by FISH in AZURE control patients only. A bone-optimized cutoff of 2.3 was used.

As seen in FIG. 10, there was a shorter time to bone as the first recurrence in MAF FISH positive patients (>=2.3) of the control arm, with a significant difference in the multivariate analysis (HR=0.47, p=0.013).

Figure 11:
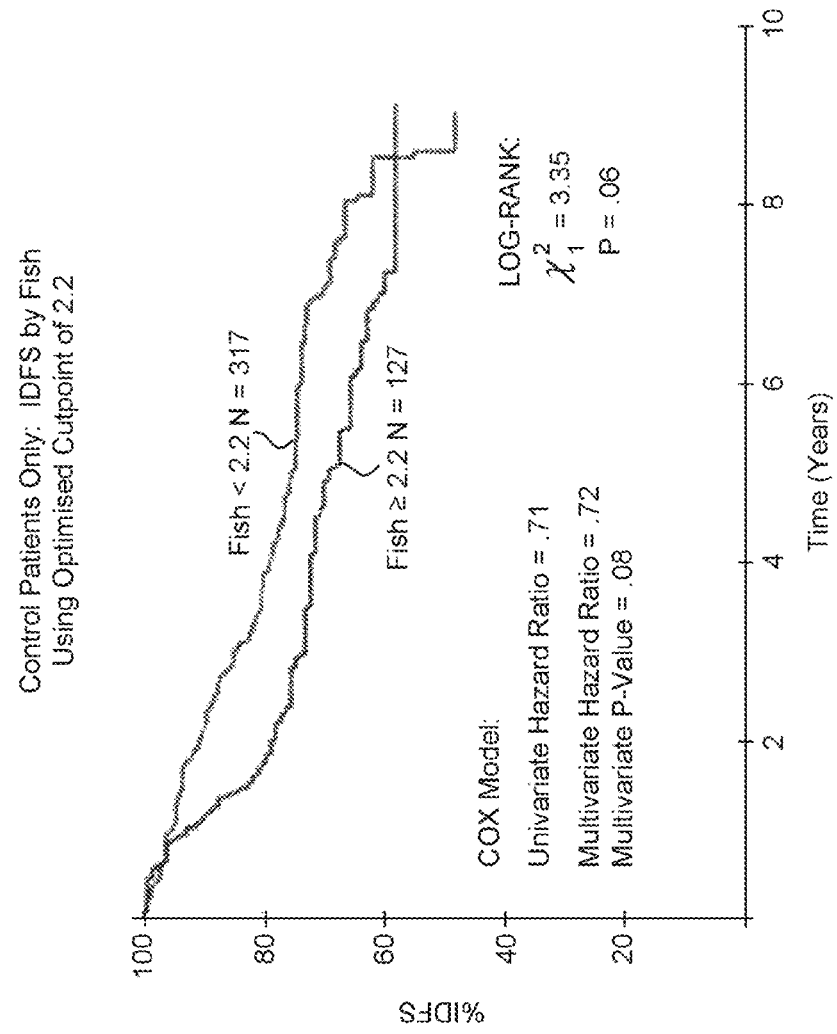
FIG. 11. IDFS by FISH in AZURE control patients only. An optimized cutoff of 2.2 was used.
Figure 12:
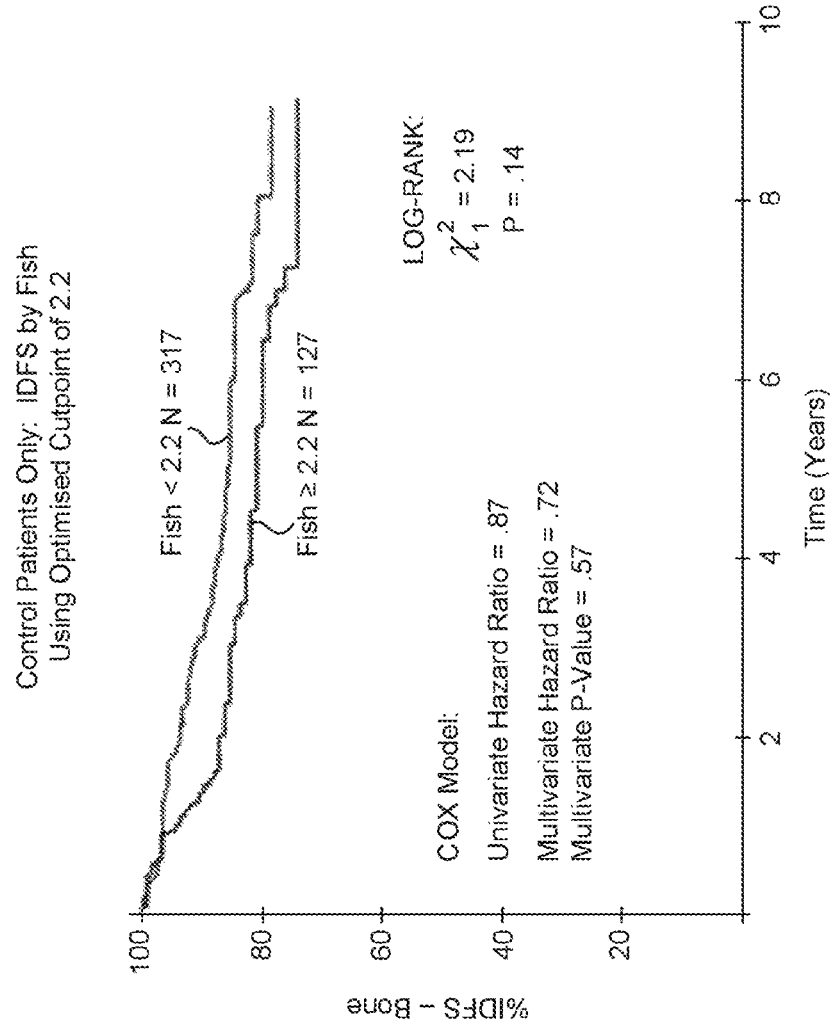
FIG. 12. Time to IDFS (excluding bone recurrence) by FISH in AZURE control patients only. An optimized cutoff of 2.2 was used.

As seen in FIG. 11, there was a trend to a shorter time to recurrence in untreated MAF positive patients (>=2.2) (HR=0.72, p=0.08, multivariate analysis) compared with untreated MAF not positive patients. FIG. 12 shows the time to IDFS (excluding bone recurrence) by FISH in AZURE control patients only. An optimized cutoff of 2.2 was used.

In summary, the predefined cut off to stratify patients according to their MAF FISH level was very close to the optimized computer based defined cutoffs. The threshold effect allows for the delineation of clear groups for appropriate (related) treatment (or avoidance of treatment). Based on the prognosis of the MAF FISH positive patients of the control arm, we saw a shorter time to bone as the first metastasis (HR=0.53, multivariate p=0.03) and a trend to a shorter time to recurrence (invasive disease) (HR=0.72, p=0.08).

Example 2: Evaluation of the Zoledronic Acid Treatment Effect According to MAF FISH Stratification The control and zoledronic acid treatment arms from the AZURE study described in Example 1 were evaluated to determine the effect of zoledronic acid treatment on MAF-stratified patients.

Figure 13:
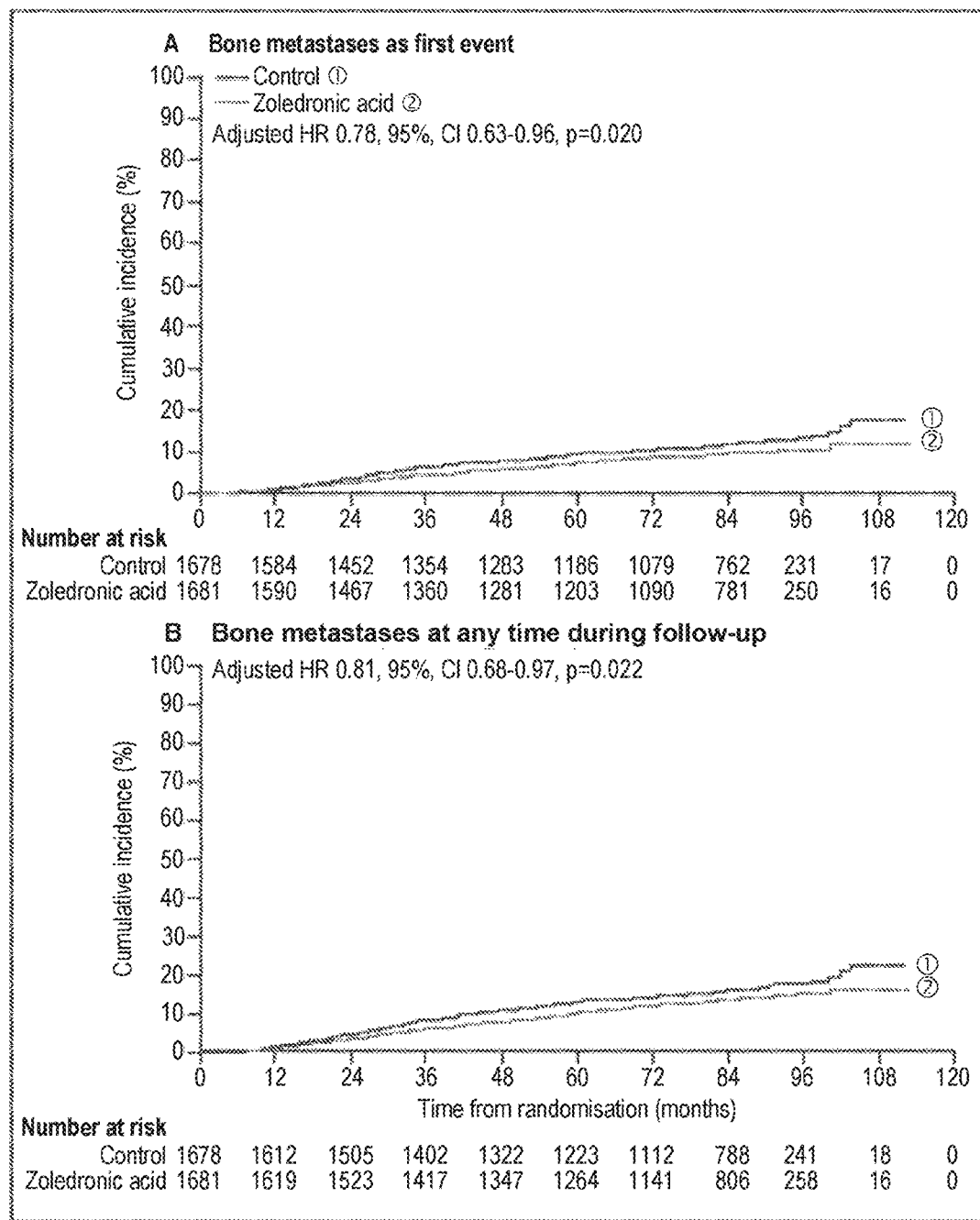
FIGS. 13A and B. Time to bone metastasis in patients in the control arm and in the zoledronic acid treatment arm.

FIG. 13 (Coleman et al *Lancet Oncol* 2014; 15: 997-1006, FIG. 3) shows the time to bone metastasis in patients in the control arm and in the zoledronic acid treatment arm of the Azure trial. FIG. 14 shows an evaluation of the time to bone metastasis as a first event. As can be seen in FIG. 14, there was a shorter time to bone as first recurrence in MAF FISH positive (>=2.3) patients of the control arm, with a significant difference in the multivariate analysis (HR=0.47, p=0.013, multivariate analysis). Zoledronic acid treatment reduced the differences in incidence of bone as first site of recurrence between MAF positive and non-positive patients, and there was no significant difference in the risk of bone metastasis at any time in MAF positive compared to MAF non-positive patients treated with zoledronic acid.

Figure 15:
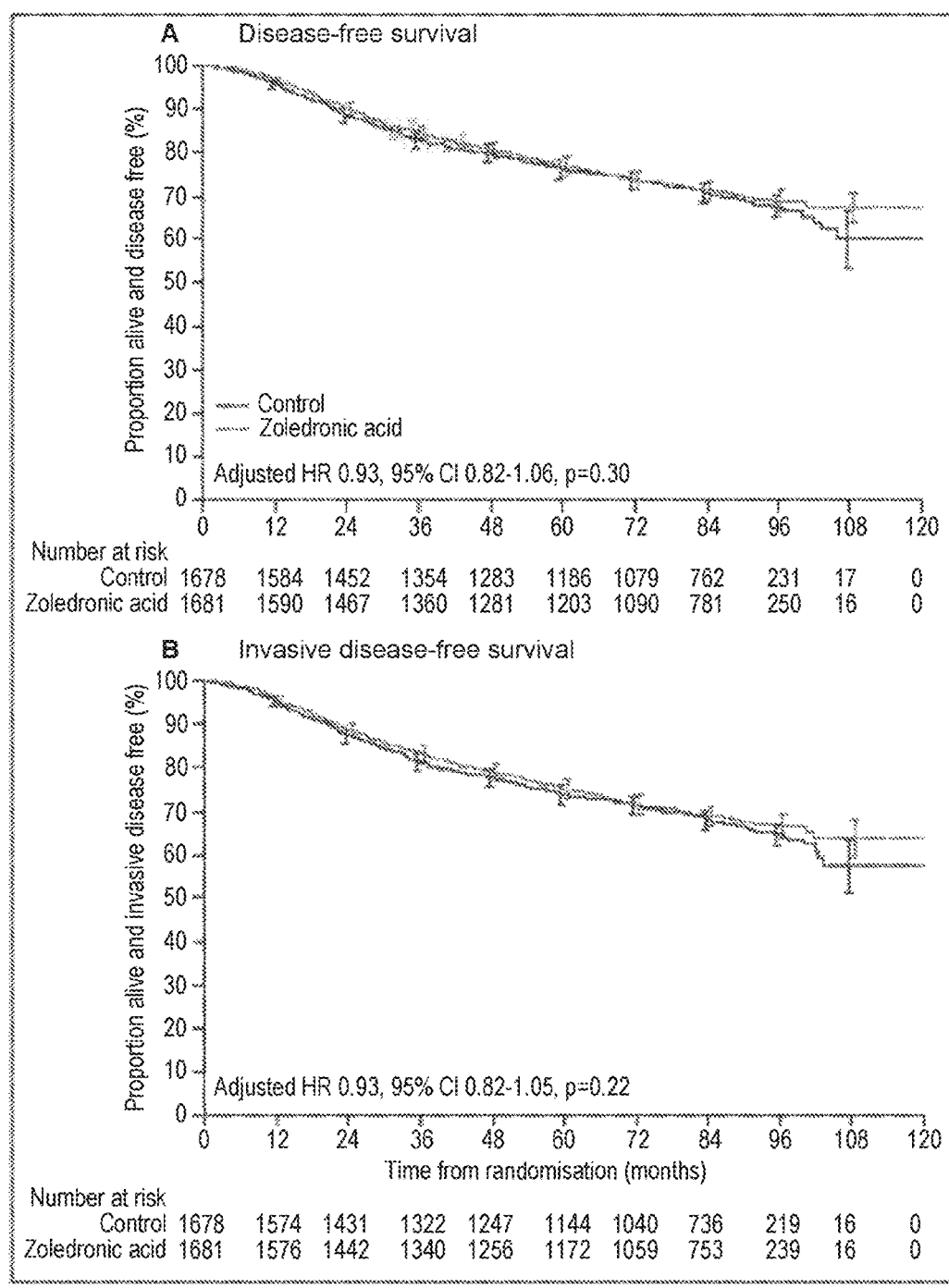

FIG. 15 (Coleman et al *Lancet Oncol* 2014; 15: 997-1006, FIG. 2) shows an analysis of disease (DFS) and invasive disease (IDFS) free survival between the control arm and the zoledronic acid treated patients in the AZURE trial.

FIG. 16 shows the time to distant recurrence between the control arm and the zoledronic acid treated patients. There was a trend to a shorter time to distant recurrence in untreated MAF positive patients (>=2.2) (HR=0.72, p=0.08, multivariate analysis). There was a significantly shorter time to recurrence (invasive disease) in MAF positive patients in the zoledronic acid treatment arm (HR=0.52, p<0.001, multivariate analysis). Treatment with zoledronic acid worsened IDFS compared to untreated MAF positive patients.

FIG. 17 shows the time to a bone metastatic event (anytime) according to treatment. Death as a competing event is used in time to bone metastasis (anytime). There was a non-significant increased risk of bone metastasis in MAF FISH positive patients (>=2.3) of the control arm (HR=0.72, p=0.18). Zoledronic acid treatment significantly reduced the risk of bone metastasis at any time in MAF FISH not positive patients (<2.3) (HR=0.52, p=0.01) compared to MAF FISH positive patients.

FIG. 18 shows the time to a bone metastatic event (anytime) according to MAF copy number (according to pre-specified MAF cut off of 2.5). Death as a competing event is used in time to bone metastasis (anytime). Zoledronic acid treatment significantly reduced the risk of bone metastasis in MAF FISH not positive patients (HR=0.65, p=0.03). Zoledronic acid treatment showed a trend to an increased risk of bone metastasis in MAF positive patients. The difference was non-significant (HR=1.54, p=0.22).

Figure 19:
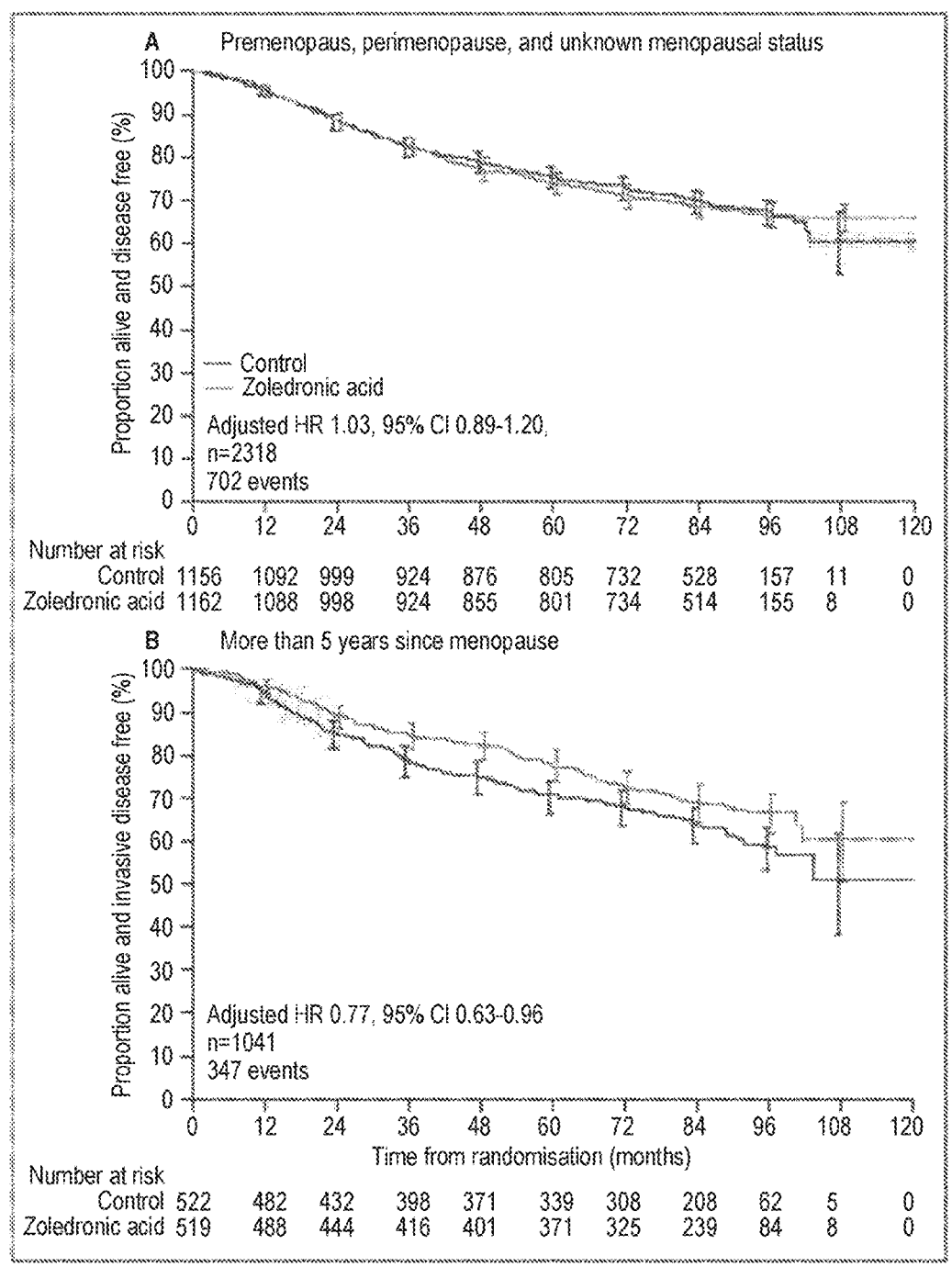

FIG. 19 shows the IDFS by menopausal status of the AZURE trial when patients are not stratified according to MAF (Coleman et al *Lancet Oncol* 2014; 15: 997-1006, FIG. 5).

FIG. 20 shows the time to a bone metastatic event (anytime) using death as a competing event according to MAF copy number (data according to a pre-specified cut off of 2.5) in postmenopausal patients. The treatment outcome in MAF positive postmenopausal patients (>2.5) showed a trend to reduce the number of bone metastasis events (HR=0.46, p=0.26, with a limited number of events). The treatment outcome in MAF non-positive postmenopausal patients treated with zoledronic acid was less effective than in MAF positive postmenopausal patients (HR=0.63 vs HR=0.46, with a limited number of events) suggesting a clear benefit of Zoledronic treatment to prevent bone metastasis in the MAF positive postmenopausal patients.

FIG. 21 shows the time to a bone metastatic event (anytime) according to MAF copy number (data according to a pre-specified cut off of 2.5) in non-post menopausal patients. There was a significantly worse zoledronic acid treatment outcome in MAF positive non-post-menopausal patients causing an increase in bone metastatic events (HR=2.44, p=0.045). There was a trend to a better outcome with zoledronic acid treatment in MAF non-positive non-post-menopausal patients (HR=0.66, p=0.08).

FIG. 22 shows the IDFS of the zoledronic acid treatment arm and the control arm, excluding bone metastasis of post-menopausal women. As seen in FIG. 22, the treatment of post-menopausal patients with zoledronic acid significantly improved the IDFS (excluding bone) of MAF FISH positive patients (>=2.2) reducing the number of invasive disease events, and there was no difference in the IDFS (excluding bone) of MAF non-positive patients.

FIG. 23 shows the IDFS of the zoledronic acid treatment arm and the control arm, excluding bone metastasis of non-post-menopausal women. As seen in FIG. 23, the treatment of non-post-menopausal women with zoledronic acid significantly worsens the IDFS (excluding bone) of MAF FISH positive patients (>=2.2), and no difference was seen in the IDFS (excluding bone) of the MAF FISH non-positive patients.

FIG. 24 shows the overall survival (OS) by treatment arm. Treatment of MAF FISH positive patients with zoledronic acid significantly impacted the OS.

FIG. 25 shows the prognosis of disease free survival (DFS) in the AZURE control arm. As can be seen in FIG. 25, there is a significantly lower disease free survival in untreated MAF positive post-menopausal patients. With regard to disease free survival: the significance of FISH status and menopausal status interaction covariate in multivariate analysis (in control patients); $Chi^2=6.23$, p-value=0.013. FIG. 26 shows the prognosis of overall survival in AZURE control arm patients. There is a trend to a shorter OS in untreated MAF positive post-menopausal patients. With regard to OS: the significance of FISH status and menopausal status interaction covariate in multivariate analysis (in control patients); $Chi^2=3.62$, p-value=0.057. FIG. 27 shows the impact of zoledronic acid treatment on DFS according to the MAF FISH value. As can be seen in FIG. 27, zoledronic acid treatment produces a differential DFS outcome between MAF FISH positive and negative patients, and these differences take place in post and non-post menopausal women.

FIG. 28 shows the impact of zoledronic acid treatment on DFS according to the MAF FISH value on postmenopausal patients. As can be seen in FIG. 28, zoledronic acid treatment produces a better DFS outcome in MAF negative post menopausal patients (HR=0.56, (95% CI, 0.33-0.95). FIG. 29 shows the impact of zoledronic acid treatment on the DFS of non-post-menopoausal women. As can be seen in FIG. 29, zoledronic acid treatment produces the worst DFS outcome in MAF positive non-post-menopausal patients. FIG. 30 shows the impact of zoledronic acid treatment on overall survival according to the MAF FISH value. As can be seen in FIG. 30, zoledronic acid treatment produces a significantly shorter overall survival in MAF positive patients. These differences take place in post and non-post menopausal women. FIG. 31 shows the impact of zoledronic acid treatment on overall survival according to MAF FISH levels in post menopausal patients. As can be seen in FIG. 31, zoledronic acid treatment shows a trend to a better overall survival outcome in MAF negative post menopausal patients. HR=0.56, (95% CI, 0.31-1.01), but a larger effect in zoledronic FISH positive patients. FIG. 32 shows the impact of zoledronic acid treatment on the overall survival of non-postmenopausal women according to MAF FISH value. As can be seen in FIG. 32, zoledronic acid treatment produces the worst overall survival outcome in MAF positive non-post menopausal patients.

A summary of the predictive value of the gene of interest (GOI) MAF on the risk of the patients for DFS and OS broken according to menopausal status is seen in Table 1.

TABLE 1

Hazard ratio for predictive power of MAF based on menopausal status

| | Hazard ratio (HR) | Lower limit of 95% CI for HR | Upper limit of 95% CI for HR |
|---|---|---|---|
| GOI status: negative v. positive for pre-menopausal patients | 3.134 | 0.913 | 10.760 |
| GOI status: negative v. positive for less than or equal to 5 years since menopause patients | 0.667 | 0.202 | 2.200 |
| GOI status: negative v. positive for more than 5 years since menopause patients | 0.552 | 0.280 | 1.089 |

TABLE 1-continued

Hazard ratio for predictive power of MAF based on menopausal status

| | Hazard ratio (HR) | Lower limit of 95% CI for HR | Upper limit of 95% CI for HR |
|---|---|---|---|
| GO status: negative v. positive for menstrual status unknown patients | 0.656 | 0.121 | 3.559 |

As can be seen, MAF is predictive in postmenopausal, unknown and perimenopausl patients at risk of a shorter DFS or worst OS. However in premenopausal women, MAF positive patients are those at less risk and are more likely to have a longer DFS and better OS.

In summary, there is a significant increased risk of bone metastasis as first site of recurrence in MAF FISH positive v. non positive patients of the control arm. (HR=0.47, p=0.013 with a cutoff=2.3) and this difference is reduced upon treatment with Zoledronic acid. In addition, Zoledronic acid treatment significantly reduced the risk of bone metastasis at any time on MAF FISH non positive patients (HR=0.65, p=0.03, cutoff=2.5). Zoledronic acid treatment shows an increased risk of bone metastasis at any time on MAF positive patients. The difference is non-significant (HR=1.54, p=0.22, cutoff=2.5). This effect is driven by menopausal status and shows the largest effect in the non-postmenopausal group. Zoledronic improves the outcome of MAF FISH positive postmenopausal patients significantly. However, Zoledronic acid worsens the outcome of MAF FISH positive non-postmenopausal patients. The effect is dependent on an increase in invasive disease (reduced IDFS) upon treatment with Zoledronic acid (suggesting that prevention of metastasis to the bone may facilitate metastasis elsewhere in non postmenopausal patients and eventually lead to metastasis to the bone as a secondary event).

MAF FISH positive patients who are not treated with zoledronic acid have a higher risk of bone metastasis and Invasive Disease (reduced IDFS including and excluding bone events). In patients treated with zoledronic acid, MAF positive patients have a worse outcome compared to untreated patients in terms of bone metastasis at any time, IDFS (including an excluding bone events) and overall survival. MAF negative patients treated with zoledronic acid have a better outcome compared to untreated patients with regard to bone metastasis at any time risk. With regard to post-menopausal women, there is a better outcome with regard to IDFS (excluding bone) in MAF positive patients treated with zoledronic acid. In non-postmenopausal women there is a worse outcome with regard to IDFS (excluding bone) in MAF positive patients treated with zoledronic acid.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

The invention claimed is:

1. A method for the treatment of a subject having breast cancer which comprises:
   i) quantifying the c-MAF gene copy number, amplification, or gain in a tumor sample of said subject and
   ii) comparing the copy number, amplification, or gain obtained in i) with a reference value, wherein the reference value is less than 2.5 copies of the c-MAF gene as measured using FISH,
   wherein said subject has not increased copy number, amplification, or gain with respect to said reference value, and administering to said subject a therapy selected from the group consisting of: clodronate, ibandronate, and zoledronic acid.

2. The method of claim 1, wherein the subject is non-postmenopausal or postmenopausal.

3. The method of claim 1, wherein the subject is further administered a therapy aiming to prevent and/or treat bone remodeling, improve disease free survival or overall survival.

4. The method according to claim 1, wherein the therapy is clodronate.

5. The method according to claim 1, wherein the therapy is zoledronic acid.

6. The method of claim 1, wherein the breast cancer is selected from the group consisting of: ER+ breast cancer, ER− breast cancer, triple negative breast cancer, of the basal-like subtype, and HER2+ breast cancer.

7. A method for the treatment of bone metastasis in a subject having breast cancer comprising determining that said subject has non increased c-MAF amplification, copy number or gain in a tumor sample with respect to a control sample and administering to said subject an agent capable of preventing or inhibiting bone remodeling or improving disease free survival or overall survival, wherein the agent capable of preventing or inhibiting bone remodeling or improving disease free survival or overall survival is selected from the group consisting of: clodronate, ibandronate, and zoledronic acid, and wherein the control sample has less than 2.5 copies of the c-MAF gene as measured using FISH.

8. The method of claim 7, wherein the subject is postmenopausal.

9. The method of claim 7, wherein the agent is clodronate.

10. The method according to claim 7, wherein the agent is zoledronic acid.

11. The method of claim 7, wherein the breast cancer is selected from the group consisting of: ER+ breast cancer, ER− breast cancer, triple negative breast cancer, of the basal-like subtype, and HER2+ breast cancer.

12. A method for the treatment of a subject having breast cancer comprising determining that said subject has non increased c-MAF amplification, copy number, or gain in a tumor sample with respect to a control sample, and administering to said subject an agent selected from the group consisting of: clodronate, ibandronate, and zoledronic acid, and wherein the control sample has less than 2.5 copies of the c-MAF gene as measured using FISH.

13. The method of claim 12, wherein the subject is non-postmenopausal, premenopausal or postmenopausal.

14. The method of claim 12, wherein the breast cancer is selected from the group consisting of: ER+ breast cancer, ER− breast cancer, triple negative breast cancer, of the basal-like subtype, and HER2+ breast cancer.

15. The method according to claim 12, wherein the agent is clodronate.

16. The method according to claim 12, wherein the agent is zoledronic acid.

17. A method for the identification of a subject having breast cancer who will benefit from treatment with an agent selected from the group consisting of clodronate, ibandronate, and zoledronic acid comprising:
   i) quantifying the c-MAF gene copy number, amplification, or gain in a tumor sample of said subject and
   ii) comparing the copy number, amplification, or gain obtained in i) with a reference value, wherein the reference value is less than 2.5 copies of the c-MAF gene as measured using FISH,
   wherein said subject has not increased copy number, amplification, or gain with respect to said reference value, and administering to said subject a therapy selected from the group consisting of clodronate, ibandronate, and zoledronic acid.

18. The method of claim 17, wherein the breast cancer is selected from the group consisting of: ER+ breast cancer, ER− breast cancer, triple negative breast cancer, of the basal-like subtype, and HER2+ breast cancer.

19. The method according to claim 17, wherein the agent is zoledronic acid.

* * * * *